(12) United States Patent
Devasagayaraj et al.

(10) Patent No.: US 7,709,493 B2
(45) Date of Patent: *May 4, 2010

(54) 4-PHENYL-6-(2,2,2-TRIFLUORO-1-PHENYLETHOXY)PYRIMIDINE-BASED COMPOUNDS AND METHODS OF THEIR USE

(75) Inventors: Arokiasamy Devasagayaraj, Plainsboro, NJ (US); Haihong Jin, Manalapan, NJ (US); Zhi-Cai Shi, Monmouth Junction, NJ (US); Ashok Tunoori, Princeton, NJ (US); Ying Wang, Plainsboro, NJ (US); Chengmin Zhang, Morristown, NJ (US)

(73) Assignee: Lexicon Pharmaceuticals, Inc., The Woodlands, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/468,974

(22) Filed: May 20, 2009

(65) Prior Publication Data

US 2009/0286817 A1 Nov. 19, 2009

Related U.S. Application Data

(63) Continuation of application No. 11/954,000, filed on Dec. 11, 2007, now Pat. No. 7,553,840.

(60) Provisional application No. 60/874,596, filed on Dec. 12, 2006.

(51) Int. Cl.
C07D 403/12 (2006.01)
A61K 31/506 (2006.01)
A61P 35/00 (2006.01)

(52) U.S. Cl. .................. 514/269; 544/309; 544/319; 544/320

(58) Field of Classification Search .......... 544/309, 544/319, 320; 514/269
See application file for complete search history.

(56) References Cited

U.S. PATENT DOCUMENTS 6,080,770 A 6/2000 Anderson

| | | | |
|---|---|---|---|
| 7,553,840 B2 * | 6/2009 | Devasagayaraj et al. ..... 514/269 |
| 2004/0082563 A1 | 4/2004 | Dorsch |
| 2005/0070538 A1 | 3/2005 | Cheng |
| 2005/0187266 A1 | 8/2005 | Su |
| 2005/0234066 A1 | 10/2005 | Bailey |
| 2007/0105959 A1 | 5/2007 | Kusuda |
| 2007/0191370 A1 | 8/2007 | Devasagayaraj |

FOREIGN PATENT DOCUMENTS

WO WO 02/00651 1/2002

OTHER PUBLICATIONS

Turner et al., Pharmacology & Therapeutics, 109, 325-338, 2006.*
Shishkina et al., Neuroscience, 150, 404-412, 2007.*
Bearcroft, C.P., et al., Gut 42:42-46 (1998).
Cote, F., et al., PNAS 100(23):13525-13530 (2003).
Cremata, V.Y., et al., Clin. Pharmacol. Ther. 7(6):768-76 (1966).
Engelman, K., et al., New England Journal of Medicine 277(21):1103-1108 (1967).
Feldman, K.S., et al., JOC 61(19):6656-6665 (1996).
Gershon, M.D., Rev. Gastroentero. Disorders, Sup.2:S25-34 (2003).
Gershon, M.D., Aliment Pharmacol Ther 20(Suppl. 7):3-14 (2004).
Shufflebotham, et al., Am. J. Gastroent. 101:2582-2587 (2006).
Search Report and Written Opinion for Corresponding International Application PCT/US2007/087068, dated Aug. 9, 2008.

* cited by examiner

Primary Examiner—Venkataraman Balasubramanian
(74) Attorney, Agent, or Firm—Max Bachrach

(57) ABSTRACT

Compounds of formula I are disclosed, as well as compositions comprising them and methods of their use to treat, prevent and/or manage diseases and disorders:

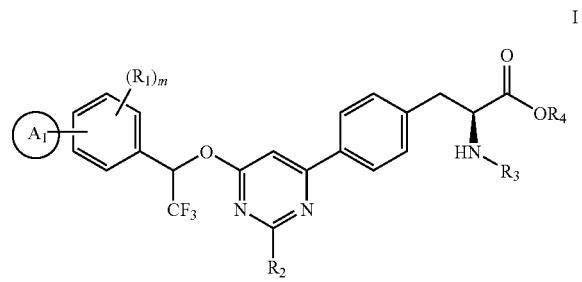

20 Claims, 1 Drawing Sheet

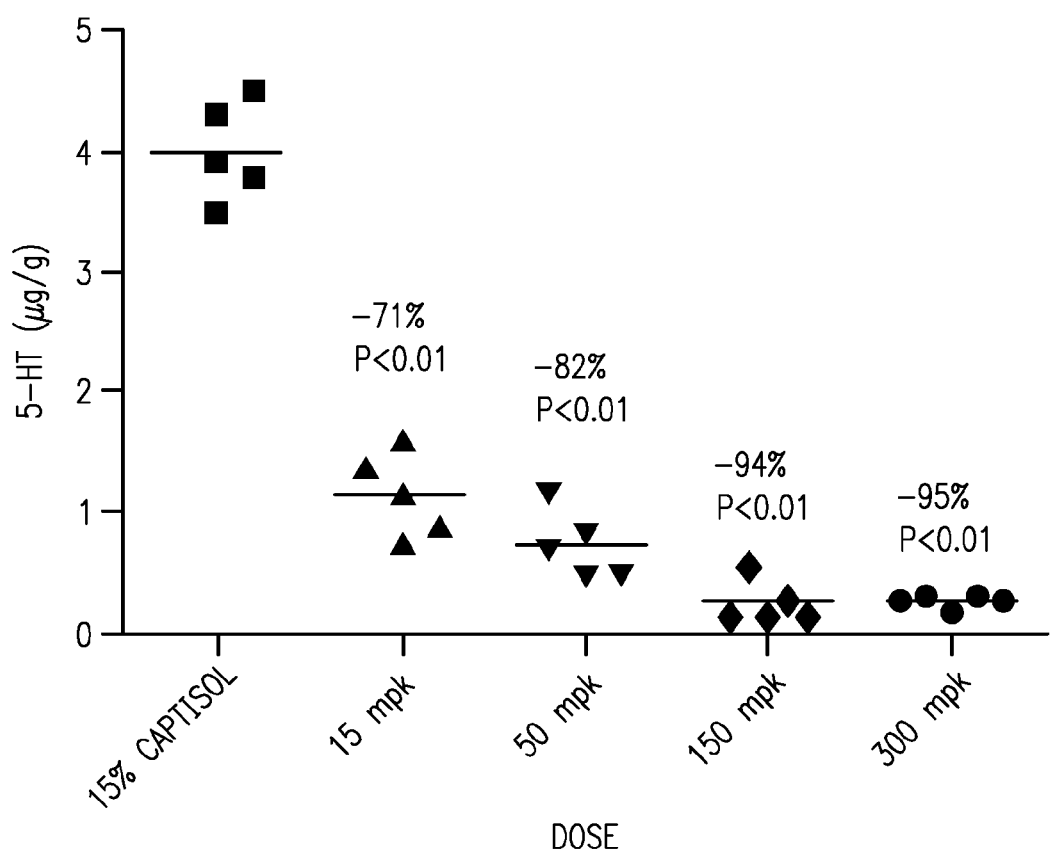

4-PHENYL-6-(2,2,2-TRIFLUORO-1-PHENYLETHOXY)PYRIMIDINE-BASED COMPOUNDS AND METHODS OF THEIR USE

This application is a continuation of U.S. application Ser. No. 11/954,000, filed Dec. 11, 2007, now U.S. Pat. No. 7,553, 840, which claims priority to U.S. provisional application No. 60/874,596, filed Dec. 12, 2006, the entireties of which are incorporated herein by reference.

1. FIELD OF THE INVENTION

This invention relates to 4-phenyl-6-(2,2,2-trifluoro-1-phenylethoxy)pyrimidine-based compounds, compositions comprising them, and their use in the treatment, prevention and management of diseases and disorders.

2. BACKGROUND

The neurotransmitter serotonin [5-hydroxytryptamine (5-HT)] is involved in multiple central nervous facets of mood control and in regulating sleep, anxiety, alcoholism, drug abuse, food intake, and sexual behavior. In peripheral tissues, serotonin is reportedly implicated in the regulation of vascular tone, gut motility, primary hemostasis, and cell-mediated immune responses. Walther, D. J., et al., *Science* 299:76 (2003).

The enzyme tryptophan hydroxylase (TPH) catalyzes the rate limiting step of the biosynthesis of serotonin. Two isoforms of TPH have been reported: TPH1, which is expressed in the periphery, primarily in the gastrointestinal (GI) tract; and TPH2, which is expressed in the serotonergic neurons. Id. The isoform TPH1 is encoded by the tph1 gene; TPH2 is encoded by the tph2 gene. Id.

Mice genetically deficient for the tph1 gene ("knockout mice") have been reported. In one case, the mice reportedly expressed normal amounts of serotonin in classical serotonergic brain regions, but largely lacked serotonin in the periphery. Id. In another, the knockout mice exhibited abnormal cardiac activity, which was attributed to a lack of peripheral serotonin. Côté, F., et al., *PNAS* 100(23):13525-13530 (2003).

Because serotonin is involved in so many biochemical processes, drugs that affect serotonin receptors are often attended by adverse effects. Thus, a need exists for new ways of treating diseases and disorders that are affected by, mediated by, or associated with serotonin.

3. SUMMARY OF THE INVENTION

This invention is directed, in part, to compounds of formula I:

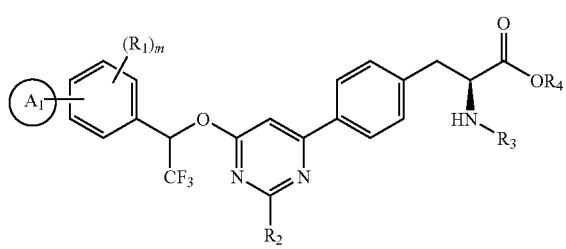

I and pharmaceutically acceptable salts and solvates thereof, wherein: $A_1$ is optionally substituted heterocycle; each $R_1$ is independently halogen, hydrogen, $C(O)R_A$, $OR_A$, $NR_BR_C$, $S(O_2)R_A$, or optionally substituted alkyl, alkyl-aryl or alkyl-heterocycle; $R_2$ is independently halogen, hydrogen, $C(O)R_A$, $OR_A$, $NR_BR_C$, $S(O_2)R_A$, or optionally substituted alkyl, alkyl-aryl or alkyl-heterocycle; $R_3$ is hydrogen, $C(O)R_A$, $C(O)OR_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; and m is 1-4.

Particular compounds inhibit TPH (e.g., TPH1) activity.

This invention is also directed to pharmaceutical compositions and to methods of treating, preventing and managing a variety of diseases and disorders.

4. BRIEF DESCRIPTION OF THE FIGURE

FIG. 1 shows the dose-dependent effect of a compound of the invention on the 5-HT levels in mouse jejunum. The compound was orally dosed in a solution of 15% Captisol® at 15, 50, 150 and 300 mpk.

5. DETAILED DESCRIPTION

This invention is based, in part, on the discovery that knocking out the tph1 gene in mice significantly reduces levels of GI serotonin, yet causes little, if any, measurable effect on the central nervous system (CNS).

This invention is also based on the discovery of compounds that inhibit TPH (e.g., TPH1). When administered to mammals, preferred compounds of the invention reduce serotonin levels, have pharmacokinetic and pharmacodynamic properties that enable their practical use for the treatment, prevention and management of diseases and disorders, and have a broad safety margin between pharmacological effect and toxicity or unfavorable side reactions.

5.1. DEFINITIONS

Unless otherwise indicated, the term "alkenyl" means a straight chain, branched and/or cyclic hydrocarbon having from 2 to 20 (e.g., 2 to 10 or 2 to 6) carbon atoms, and including at least one carbon-carbon double bond. Representative alkenyl moieties include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl and 3-decenyl.

Unless otherwise indicated, the term "alkyl" means a straight chain, branched and/or cyclic ("cycloalkyl") hydrocarbon having from 1 to 20 (e.g., 1 to 10 or 1 to 4) carbon atoms. Alkyl moieties having from 1 to 4 carbons are referred to as "lower alkyl." Examples of alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl and dodecyl. Cycloalkyl moieties may be monocyclic or multicyclic, and examples include cyclopropyl, cyclobutyl, cyclopentyl, cyclohexyl, and adamantyl. Additional examples of alkyl moieties have linear, branched and/or cyclic portions (e.g., 1-ethyl-4-methyl-cyclohexyl). The term "alkyl" includes saturated hydrocarbons as well as alkenyl and alkynyl moieties.

Unless otherwise indicated, the term "alkoxy" means an —O-alkyl group. Examples of alkoxy groups include —OCH$_3$, —OCH$_2$CH$_3$, —O(CH$_2$)$_2$CH$_3$, —O(CH$_2$)$_3$CH$_3$, —O(CH$_2$)$_4$CH$_3$, and —O(CH$_2$)$_5$CH$_3$.

Unless otherwise indicated, the term "alkylaryl" or "alkyl-aryl" means an alkyl moiety bound to an aryl moiety.

Unless otherwise indicated, the term "alkylheteroaryl" or "alkyl-heteroaryl" means an alkyl moiety bound to a heteroaryl moiety.

Unless otherwise indicated, the term "alkylheterocycle" or "alkyl-heterocycle" means an alkyl moiety bound to a heterocycle moiety.

Unless otherwise indicated, the term "alkynyl" means a straight chain, branched or cyclic hydrocarbon having from 2 to 20 (e.g., 2 to 20 or 2 to 6) carbon atoms, and including at least one carbon-carbon triple bond. Representative alkynyl moieties include acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl and 9-decynyl.

Unless otherwise indicated, the term "aryl" means an aromatic ring or an aromatic or partially aromatic ring system composed of carbon and hydrogen atoms. An aryl moiety may comprise multiple rings bound or fused together. Examples of aryl moieties include anthracenyl, azulenyl, biphenyl, fluorenyl, indan, indenyl, naphthyl, phenanthrenyl, phenyl, 1,2,3,4-tetrahydro-naphthalene, and tolyl.

Unless otherwise indicated, the term "arylalkyl" or "aryl-alkyl" means an aryl moiety bound to an alkyl moiety.

Unless otherwise indicated, the terms "biohydrolyzable amide," "biohydrolyzable ester," "biohydrolyzable carbamate," "biohydrolyzable carbonate," "biohydrolyzable ureido" and "biohydrolyzable phosphate" mean an amide, ester, carbamate, carbonate, ureido, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include lower alkyl esters, alkoxyacyloxy esters, alkyl acylamino alkyl esters, and choline esters. Examples of biohydrolyzable amides include lower alkyl amides, α-amino acid amides, alkoxyacyl amides, and alkylaminoalkyl-carbonyl amides. Examples of biohydrolyzable carbamates include lower alkylamines, substituted ethylenediamines, aminoacids, hydroxyalkylamines, heterocyclic and heteroaromatic amines, and polyether amines.

Unless otherwise indicated, the phrases "disease or disorder mediated by peripheral serotonin" and "disease and disorder mediated by peripheral serotonin" mean a disease and/or disorder having one or more symptoms, the severity of which are affected by peripheral serotonin levels.

Unless otherwise indicated, the terms "halogen" and "halo" encompass fluorine, chlorine, bromine, and iodine.

Unless otherwise indicated, the term "heteroalkyl" refers to an alkyl moiety (e.g., linear, branched or cyclic) in which at least one of its carbon atoms has been replaced with a heteroatom (e.g., N, O or S).

Unless otherwise indicated, the term "heteroaryl" means an aryl moiety wherein at least one of its carbon atoms has been replaced with a heteroatom (e.g., N, O or S). Examples include acridinyl, benzimidazolyl, benzofuranyl, benzoisothiazolyl, benzoisoxazolyl, benzoquinazolinyl, benzothiazolyl, benzoxazolyl, furyl, imidazolyl, indolyl, isothiazolyl, isoxazolyl, oxadiazolyl, oxazolyl, phthalazinyl, pyrazinyl, pyrazolyl, pyridazinyl, pyridyl, pyrimidinyl, pyrimidyl, pyrrolyl, quinazolinyl, quinolinyl, tetrazolyl, thiazolyl, and triazinyl.

Unless otherwise indicated, the term "heteroarylalkyl" or "heteroaryl-alkyl" means a heteroaryl moiety bound to an alkyl moiety.

Unless otherwise indicated, the term "heterocycle" refers to an aromatic, partially aromatic or non-aromatic monocyclic or polycyclic ring or ring system comprised of carbon, hydrogen and at least one heteroatom (e.g., N, O or S). A heterocycle may comprise multiple (i.e., two or more) rings fused or bound together. Heterocycles include heteroaryls. Examples include benzo[1,3]dioxolyl, 2,3-dihydro-benzo[1,4]dioxinyl, cinnolinyl, furanyl, hydantoinyl, morpholinyl, oxetanyl, oxiranyl, piperazinyl, piperidinyl, pyrrolidinonyl, pyrrolidinyl, tetrahydrofuranyl, tetrahydropyranyl, tetrahydropyridinyl, tetrahydropyrimidinyl, tetrahydrothiophenyl, tetrahydrothiopyranyl and valerolactamyl.

Unless otherwise indicated, the term "heterocyclealkyl" or "heterocycle-alkyl" refers to a heterocycle moiety bound to an alkyl moiety.

Unless otherwise indicated, the term "heterocycloalkyl" refers to a non-aromatic heterocycle.

Unless otherwise indicated, the term "heterocycloalkylalkyl" or "heterocycloalkyl-alkyl" refers to a heterocycloalkyl moiety bound to an alkyl moiety.

Unless otherwise indicated, the terms "manage," "managing" and "management" encompass preventing the recurrence of the specified disease or disorder, or of one or more of its symptoms, in a patient who has already suffered from the disease or disorder, and/or lengthening the time that a patient who has suffered from the disease or disorder remains in remission. The terms encompass modulating the threshold, development and/or duration of the disease or disorder, or changing the way that a patient responds to the disease or disorder.

Unless otherwise indicated, the term "pharmaceutically acceptable salts" refers to salts prepared from pharmaceutically acceptable non-toxic acids or bases including inorganic acids and bases and organic acids and bases. Suitable pharmaceutically acceptable base addition salts include metallic salts made from aluminum, calcium, lithium, magnesium, potassium, sodium and zinc or organic salts made from lysine, N,N'-dibenzylethylenediamine, chloroprocaine, choline, diethanolamine, ethylenediamine, meglumine (N-methylglucamine) and procaine. Suitable non-toxic acids include inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include hydrochloride and mesylate salts. Others are well-known in the art. See, e.g., *Remington's Pharmaceutical Sciences,* 18$^{th}$ ed. (Mack Publishing, Easton Pa.: 1990) and *Remington: The Science and Practice of Pharmacy,* 19$^{th}$ ed. (Mack Publishing, Easton Pa.: 1995).

Unless otherwise indicated, the term "potent TPH1 inhibitor" is a compound that has a TPH1_IC$_{50}$ of less than about 10 µM.

Unless otherwise indicated, the terms "prevent," "preventing" and "prevention" contemplate an action that occurs before a patient begins to suffer from the specified disease or disorder, which inhibits or reduces the severity of the disease or disorder, or of one or more of its symptoms. The terms encompass prophylaxis.

Unless otherwise indicated, the term "prodrug" encompasses pharmaceutically acceptable esters, carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of compounds disclosed herein. Examples of prodrugs include compounds that comprise a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Prodrugs of compounds disclosed herein are readily envisioned and prepared by those of ordinary skill in the art. See, e.g., *Design of Prodrugs*, Bundgaard, A. Ed., Elseview, 1985; Bundgaard, H., "Design and Application of Prodrugs," *A Textbook of Drug Design and Development*, Krosgaard-Larsen and H. Bundgaard, Ed., 1991, Chapter 5, p. 113-191; and Bundgaard, H., *Advanced Drug Delivery Review*, 1992, 8, 1-38.

Unless otherwise indicated, a "prophylactically effective amount" of a compound is an amount sufficient to prevent a disease or condition, or one or more symptoms associated with the disease or condition, or prevent its recurrence. A prophylactically effective amount of a compound is an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

Unless otherwise indicated, the term "protecting group" or "protective group," when used to refer to part of a molecule subjected to a chemical reaction, means a chemical moiety that is not reactive under the conditions of that chemical reaction, and which may be removed to provide a moiety that is reactive under those conditions. Protecting groups are well known in the art. See, e.g., Greene, T. W. and Wuts, P. G. M., *Protective Groups in Organic Synthesis* (3$^{rd}$ ed., John Wiley & Sons: 1999); Larock, R. C., *Comprehensive Organic Transformations* (2$^{nd}$ ed., John Wiley & Sons: 1999). Some examples include benzyl, diphenylmethyl, trityl, Cbz, Boc, Fmoc, methoxycarbonyl, ethoxycarbonyl, and pthalimido.

Unless otherwise indicated, the term "pseudohalogen" refers to a polyatomic anion that resembles a halide ion in its acid-base, substitution, and redox chemistry, generally has low basicity, and forms a free radical under atom transfer radical polymerization conditions. Examples of pseudohalogens include azide ions, cyanide, cyanate, thiocyanate, thiosulfate, sulfonates, and sulfonyl halides.

Unless otherwise indicated, the term "selective TPH1 inhibitor" is a compound that has a TPH2_IC$_{50}$ that is at least about 10 times greater than its TPH1_IC$_{50}$.

Unless otherwise indicated, the term "stereomerically enriched composition of" a compound refers to a mixture of the named compound and its stereoisomer(s) that contains more of the named compound than its stereoisomer(s). For example, a stereoisomerically enriched composition of (S)-butan-2-ol encompasses mixtures of (S)-butan-2-ol and (R)-butan-2-ol in ratios of, e.g., about 60/40, 70/30, 80/20, 90/10, 95/5, and 98/2.

Unless otherwise indicated, the term "stereoisomeric mixture" encompasses racemic mixtures as well as stereomerically enriched mixtures (e.g., R/S=30/70, 35/65, 40/60, 45/55, 55/45, 60/40, 65/35 and 70/30).

Unless otherwise indicated, the term "stereomerically pure" means a composition that comprises one stereoisomer of a compound and is substantially free of other stereoisomers of that compound. For example, a stereomerically pure composition of a compound having one stereocenter will be substantially free of the opposite stereoisomer of the compound. A stereomerically pure composition of a compound having two stereocenters will be substantially free of other diastereomers of the compound. A stereomerically pure composition of a compound that has multiple stereocenters, but which is drawn or named in such a way that the stereochemistries of less than all of its stereocenters are defined, is substantially free of the isomers of the compound that have different stereochemistries at the stereocenters for which stereochemistry is defined. For example, "stereomerically pure ((1R)-1,2-dichloropropyl)benzene" refers to ((1R)-1,2-dichloropropyl)benzene that is substantially free of ((1S)-1,2-dichloropropyl)benzene.

A typical stereomerically pure compound comprises greater than about 80% by weight of one stereoisomer of the compound and less than about 20% by weight of other stereoisomers of the compound, greater than about 90% by weight of one stereoisomer of the compound and less than about 10% by weight of the other stereoisomers of the compound, greater than about 95% by weight of one stereoisomer of the compound and less than about 5% by weight of the other stereoisomers of the compound, greater than about 97% by weight of one stereoisomer of the compound and less than about 3% by weight of the other stereoisomers of the compound, or greater than about 99% by weight of one stereoisomer of the compound and less than about 1% by weight of the other stereoisomers of the compound.

Unless otherwise indicated, the term "substituted," when used to describe a chemical structure or moiety, refers to a derivative of that structure or moiety wherein one or more of its hydrogen atoms is substituted with an atom, chemical moiety or functional group such as, but not limited to, alcohol, aldehylde, alkoxy, alkanoyloxy, alkoxycarbonyl, alkenyl, alkyl (e.g., methyl, ethyl, propyl, t-butyl), alkynyl, alkylcarbonyloxy (—OC(O)alkyl), amide (—C(O)NH-alkyl- or -alkylNHC(O)alkyl), amidinyl (—C(NH)NH-alkyl or —C(NR)NH$_2$), amine (primary, secondary and tertiary such as alkylamino, arylamino, arylalkylamino), aroyl, aryl, aryloxy, azo, carbamoyl (—NHC(O)O-alkyl- or —OC(O)NH-alkyl), carbamyl (e.g., CONH$_2$, as well as CONH-alkyl, CONH-aryl, and CONH-arylalkyl), carbonyl, carboxyl, carboxylic acid, carboxylic acid anhydride, carboxylic acid chloride, cyano, ester, epoxide, ether (e.g., methoxy, ethoxy), guanidino, halo, haloalkyl (e.g., —CCl$_3$, —CF$_3$, —C(CF$_3$)$_3$), heteroalkyl, hemiacetal, imine (primary and secondary), isocyanate, isothiocyanate, ketone, nitrile, nitro, oxygen (i.e., to provide an oxo group), phosphodiester, sulfide, sulfonamido (e.g., SO$_2$NH$_2$), sulfone, sulfonyl (including alkylsulfonyl, arylsulfonyl and arylalkylsulfonyl), sulfoxide, thiol (e.g., sulfhydryl, thioether) and urea (—NHCONH-alkyl-).

Unless otherwise indicated, a "therapeutically effective amount" of a compound is an amount sufficient to provide a therapeutic benefit in the treatment or management of a disease or condition, or to delay or minimize one or more symptoms associated with the disease or condition. A therapeutically effective amount of a compound is an amount of therapeutic agent, alone or in combination with other therapies, which provides a therapeutic benefit in the treatment or management of the disease or condition. The term "therapeutically effective amount" can encompass an amount that improves overall therapy, reduces or avoids symptoms or causes of a disease or condition, or enhances the therapeutic efficacy of another therapeutic agent.

Unless otherwise indicated, the term "TPH1_IC$_{50}$" is the IC$_{50}$ of a compound for TPH1 as determined using the in vitro inhibition assay described in the Examples, below.

Unless otherwise indicated, the term "TPH2_IC$_{50}$" is the IC$_{50}$ of a compound for TPH2 as determined using the in vitro inhibition assay described in the Examples, below.

Unless otherwise indicated, the terms "treat," "treating" and "treatment" contemplate an action that occurs while a patient is suffering from the specified disease or disorder, which reduces the severity of the disease or disorder, or one or more of its symptoms, or retards or slows the progression of the disease or disorder.

Unless otherwise indicated, the term "include" has the same meaning as "include" and the term "includes" has the same meaning as "includes, but is not limited to." Similarly, the term "such as" has the same meaning as the term "such as, but not limited to."

Unless otherwise indicated, one or more adjectives immediately preceding a series of nouns is to be construed as applying to each of the nouns. For example, the phrase "optionally substituted alky, aryl, or heteroaryl" has the same meaning as "optionally substituted alky, optionally substituted aryl, or optionally substituted heteroaryl."

It should be noted that a chemical moiety that forms part of a larger compound may be described herein using a name commonly accorded it when it exists as a single molecule or a name commonly accorded its radical. For example, the terms "pyridine" and "pyridyl" are accorded the same meaning when used to describe a moiety attached to other chemical moieties. Thus, the two phrases "XOH, wherein X is pyridyl" and "XOH, wherein X is pyridine" are accorded the same meaning, and encompass the compounds pyridin-2-ol, pyridin-3-ol and pyridin-4-ol.

It should also be noted that if the stereochemistry of a structure or a portion of a structure is not indicated with, for example, bold or dashed lines, the structure or the portion of the structure is to be interpreted as encompassing all stereoisomers of it. Similarly, names of compounds having one or more chiral centers that do not specify the stereochemistry of those centers encompass pure stereoisomers and mixtures thereof. Moreover, any atom shown in a drawing with unsatisfied valences is assumed to be attached to enough hydrogen atoms to satisfy the valences. In addition, chemical bonds depicted with one solid line parallel to one dashed line encompass both single and double (e.g., aromatic) bonds, if valences permit.

5.2. Compounds

This invention encompasses, inter alia, compounds of formula I:

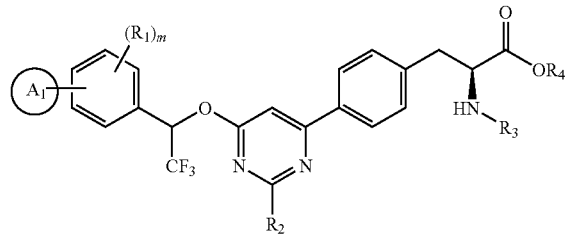

and pharmaceutically acceptable salts and solvates thereof, wherein: $A_1$ is optionally substituted heterocycle; each $R_1$ is independently halogen, hydrogen, C(O)$R_A$, O$R_A$, N$R_B R_C$, S(O$_2$)$R_A$, or optionally substituted alkyl, alkyl-aryl or alkyl-heterocycle; $R_2$ is independently halogen, hydrogen, C(O)$R_A$, O$R_A$, N$R_B R_C$, S(O$_2$)$R_A$, or optionally substituted alkyl, alkyl-aryl or alkyl-heterocycle; $R_3$ is hydrogen, C(O)$R_A$, C(O)O$R_A$, or optionally substituted alkyl, alkyl-aryl, alkyl-heterocycle, aryl, or heterocycle; $R_4$ is hydrogen or optionally substituted alkyl, alkyl-aryl, alkyl-heterocycle, aryl, or heterocycle; each $R_A$ is independently hydrogen or optionally substituted alkyl, alkyl-aryl or alkyl-heterocycle; each $R_B$ is independently hydrogen or optionally substituted alkyl, alkyl-aryl or alkyl-heterocycle; each $R_C$ is independently hydrogen or optionally substituted alkyl, alkyl-aryl or alkyl-heterocycle; and m is 1-4.

In one embodiment, the compound is of the formula:

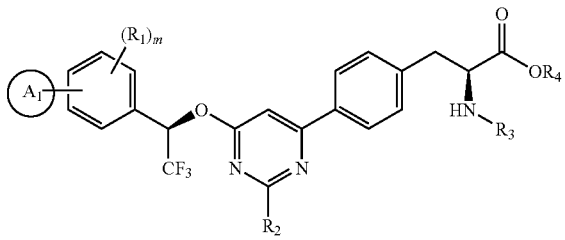

In another, it is of the formula:

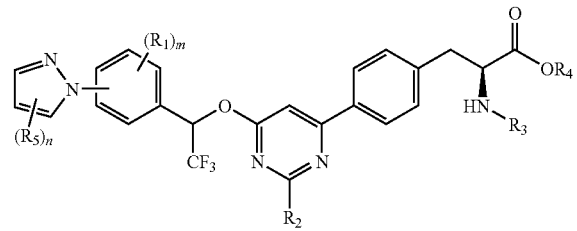

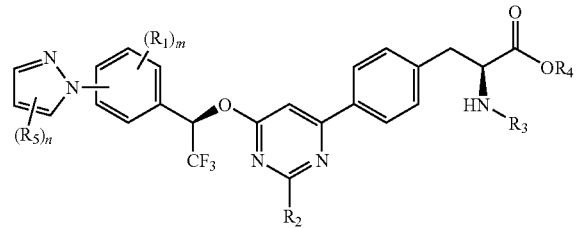

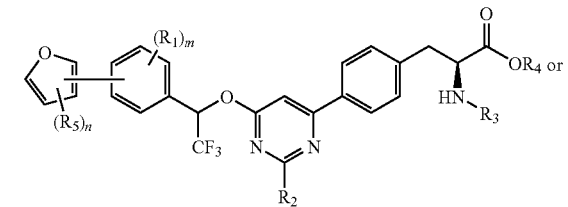

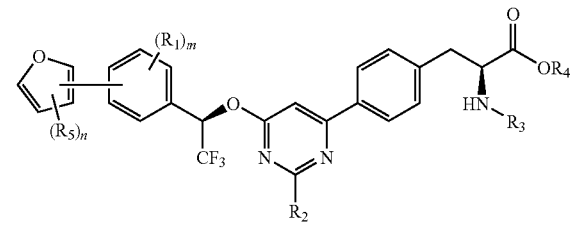

wherein: each $R_5$ is independently halogen, hydrogen, C(O)$R_A$, O$R_A$, N$R_B R_C$, S(O$_2$)$R_A$, or optionally substituted alkyl, alkyl-aryl or alkyl-heterocycle; and n is 1-3.

In another, it is of the formula:

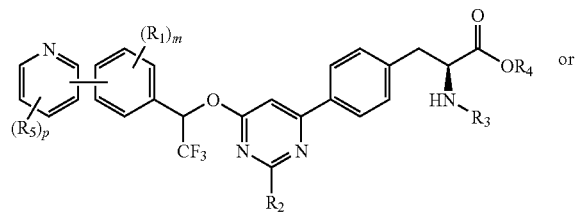

or

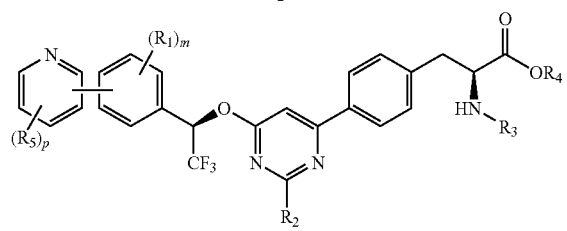

wherein: each $R_5$ is independently halogen, hydrogen, C(O)$R_A$, $OR_A$, $NR_BR_C$, $S(O_2)R_A$, or optionally substituted alkyl, alkyl-aryl or alkyl-heterocycle; and p is 1-4.

In another, it is of the formula:

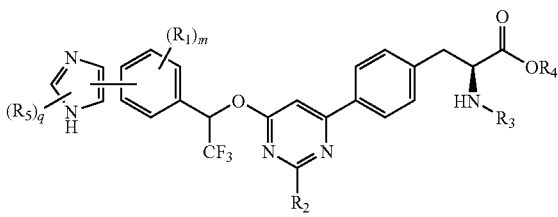

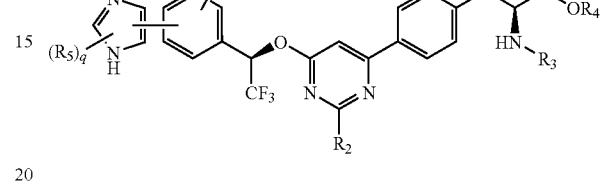

wherein: each $R_5$ is independently halogen, hydrogen, C(O)$R_A$, $OR_A$, $NR_BR_C$, $S(O_2)R_A$, or optionally substituted alkyl, alkyl-aryl or alkyl-heterocycle; and q is 1-2.

In another, it is of the formula:

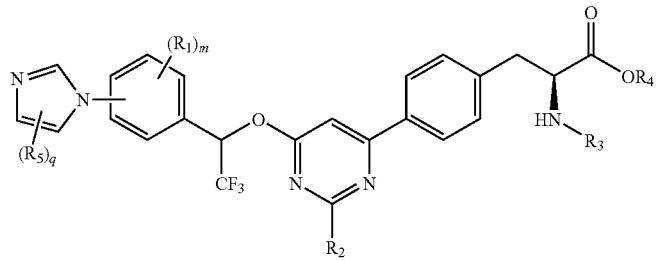

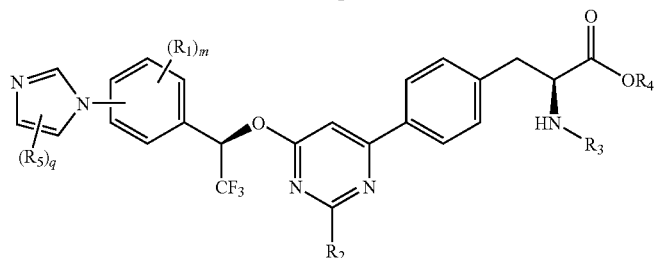

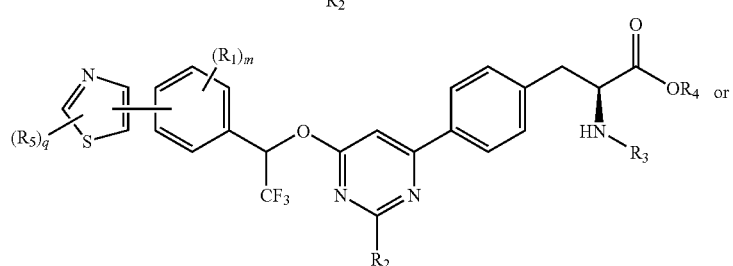

or

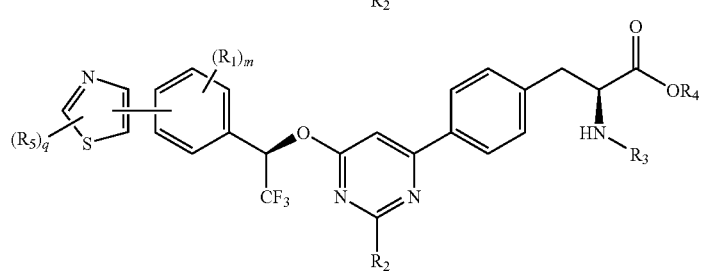

wherein: each $R_5$ is independently halogen, hydrogen, $C(O)R_4$, $OR_4$, $NR_BR_C$, $S(O_2)R_4$, or optionally substituted alkyl, alkyl-aryl or alkyl-heterocycle; and q is 1-2.

With regard to the various formulae disclosed herein, in particular compounds of the invention, $A_1$ is aromatic. In others, $A_1$ is not aromatic. In some, $A_1$ is optionally substituted with one or more of halogen or lower alkyl.

In some, $R_1$ is hydrogen or halogen.

In some, m is 1.

In some, $R_2$ is hydrogen or amino.

In some, $R_3$ is hydrogen or lower alkyl. In others, $R_3$ is $C(O)OR_4$ and $R_4$ is alkyl.

In some, $R_4$ is hydrogen or lower alkyl.

In some, $R_5$ is hydrogen or lower alkyl (e.g., methyl).

In some, n is 1.

In some, p is 1.

In some, q is 1.

This invention encompasses stereomerically pure compounds and stereomerically enriched compositions of them. Stereoisomers may be asymmetrically synthesized or resolved using standard techniques such as chiral columns, chiral resolving agents, or enzymatic resolution. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions*, p. 268 (E. L. Eliel, Ed., Univ. of Notre Dame Press, Notre Dame, Ind., 1972).

Particular compounds of the invention are potent TPH1 inhibitors. Specific compounds have a TPH1_$IC_{50}$ of less than about 10, 5, 2.5, 1, 0.75, 0.5, 0.4, 0.3, 0.2, 0.1, or 0.05 μM.

Particular compounds are selective TPH1 inhibitors. Specific compounds have a TPH1_$IC_{50}$ that is about 10, 25, 50, 100, 250, 500, or 1000 times less than their TPH2_$IC_{50}$.

Particular compounds do not significantly inhibit human tyrosine hydroxylase (TH). For example, specific compounds have an $IC_{50}$ for TH of greater than about 100, 250, 500 or 1000 μm.

Particular compounds do not significantly inhibit human phenylalanine hydroxylase (PAH). For example, specific compounds have an $IC_{50}$ for PAH of greater than about 100, 250, 500 or 1000 μM.

Particular compounds of the invention do not significantly bind (e.g., inhibit with an $IC_{50}$ of greater than about 10, 25, 50, 100, 250, 500, 750, or 1000 μM) to one or more of the following: angiotensin converting enzyme, erythropoietin (EPO) receptor, factor IX, factor XI, integrin (e.g., α4), isoxazoline or isoxazole fibrinogen receptor, metalloprotease, neutral endopeptidase (NEP), phosphatase (e.g., tyrosine phosphatase), phosphodiesterase (e.g., PDE-4), polymerase, PPARγ, TNF-α, vascular cell adhesion molecule-1 (VCAM-1), or the vitronectin receptor. The ability of a compound to bind to (e.g., inhibit) any of these targets can be readily determined using methods known in the art, as described in references cited above. Specific compounds of the invention do not inhibit cell adhesion.

When administered to mammals (e.g., mice, rats, dogs, monkeys or humans), certain compounds of the invention do not readily cross the blood/brain barrier (e.g., less than about 5, 2.5, 2, 1.5, 1, 0.5, or 0.01 percent of compound in the blood passes into the brain). The ability or inability of a compound to cross the blood/brain barrier can be determined by methods known in the art. See, e.g., Riant, P. et al., *Journal of Neurochemistry* 51:421-425 (1988); Kastin, A. J., Akerstrom, V., *J. Pharmacol. Exp. Therapeutics* 294:633-636 (2000); W. A. Banks, W. A., et al., *J. Pharmacol. Exp. Therapeutics* 302: 1062-1069 (2002).

5.3. Synthesis of Compounds

Compounds of the invention can be prepared by methods known in the art and by methods described herein.

For example, compounds of formula I can be prepared as shown in Scheme 1:

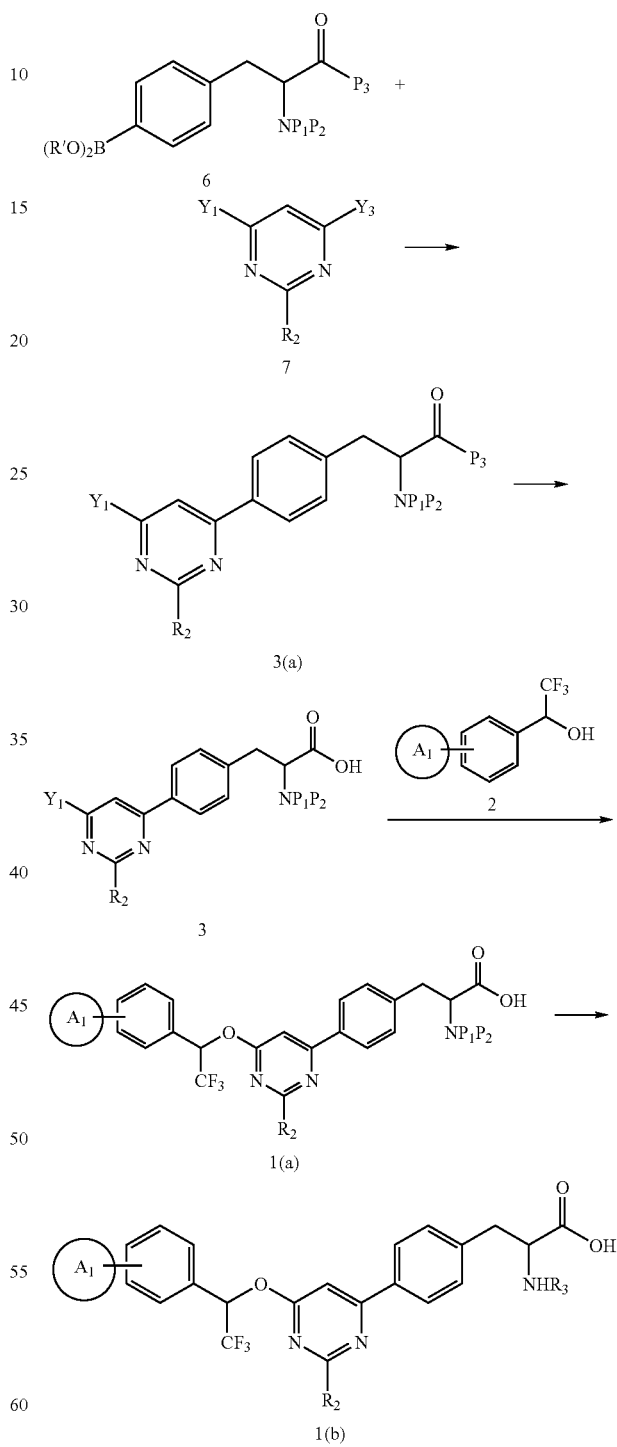

wherein $P_1$ is $R_1$ or a protecting group; $P_2$ is a protecting group; $P_3$ is $OR_2$ or a protecting group; $Y_1$ and $Y_3$ are halogen (e.g., Br, Cl) or an appropriate pseudohalide (e.g., triflate); and each the groups $A_1$, $R_1$, $R_2$, and $R_3$ are defined elsewhere herein.

Compounds of the invention can also be prepared by the approach represented below in Scheme 2:

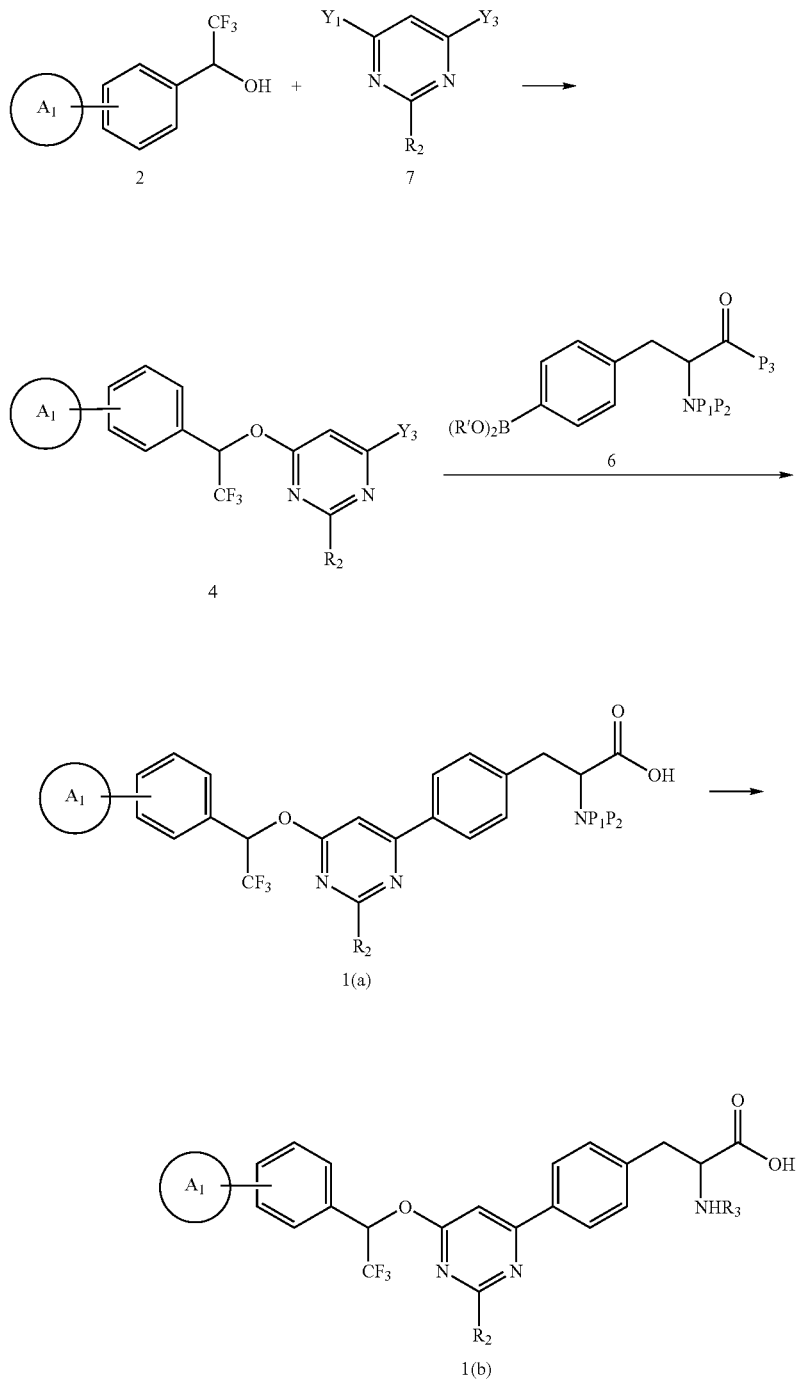

The individual reactions shown in the schemes above can be performed using conditions known in the art. For example, palladium catalysts and conditions suitable for the Suzuki coupling of the boron and halogen-containing moieties are well known, and examples are provided below. In addition, types and appropriate uses of protecting groups are well known, as are methods of their removal and replacement with moieties such as, but not limited to, hydrogen (e.g., hydrolysis under acidic or basic conditions).

Ester derivatives of compounds of the invention can be readily prepared using methods such as that shown below in Scheme 3:

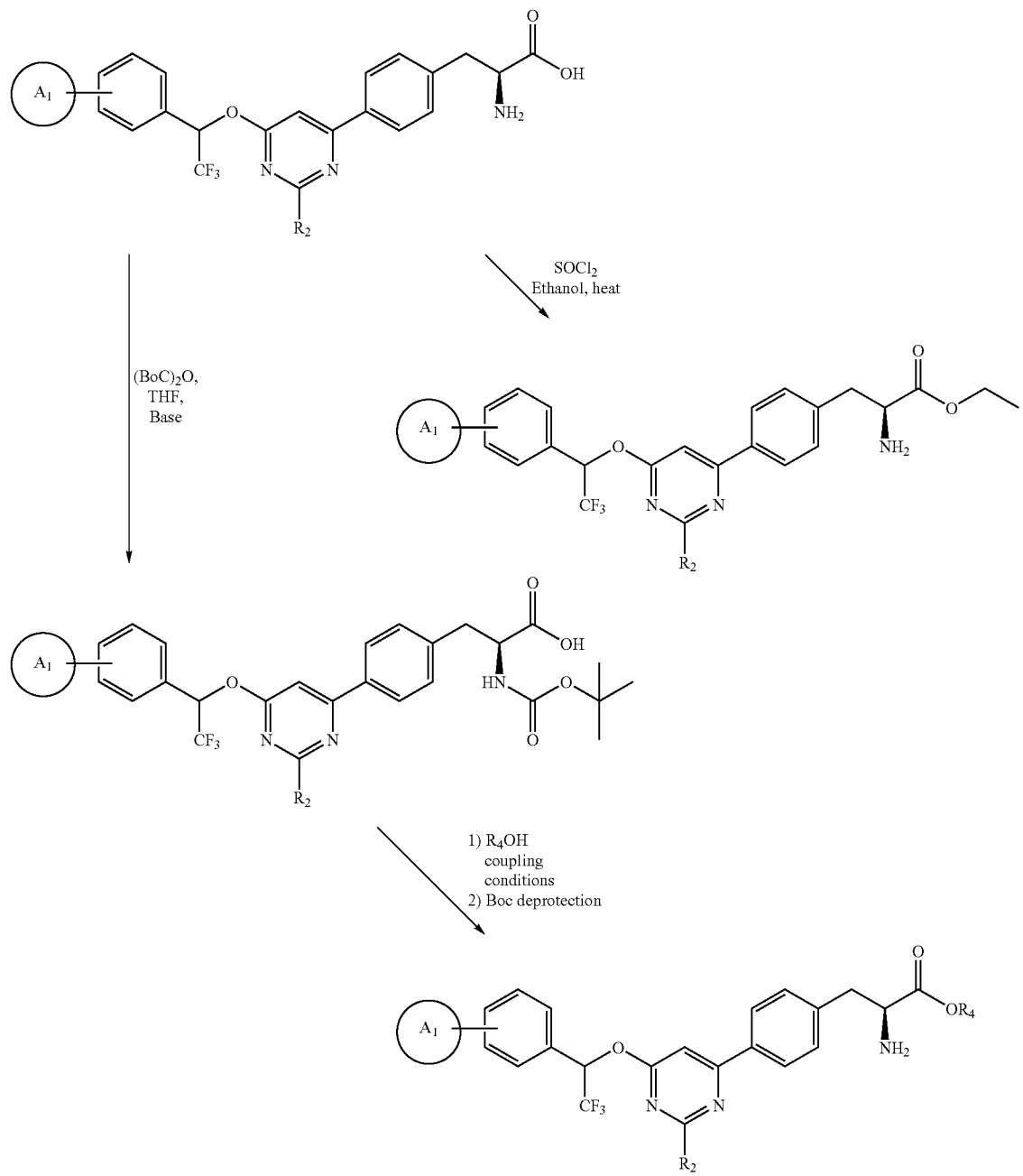

Scheme 3

Using methods known in the art, the synthetic approaches shown above are readily modified to obtain a wide range of compounds. For example, chiral chromatography and other techniques known in the art may be used to separate stereoisomers of the final product. See, e.g., Jacques, J., et al., *Enantiomers, Racemates and Resolutions* (Wiley Interscience, New York, 1981); Wilen, S. H., et al., *Tetrahedron* 33:2725 (1977); Eliel, E. L., *Stereochemistry of Carbon Compounds* (McGraw Hill, N.Y., 1962); and Wilen, S. H., *Tables of Resolving Agents and Optical Resolutions*, p. 268 (E. L. Eliel, Ed., Univ. of Notre Dame Press, Notre Dame, Ind., 1972). In addition, as shown in some of the schemes above, syntheses may utilize chiral starting materials to yield stereomerically enriched or pure products.

5.4. Methods of Use

This invention encompasses a method of inhibiting TPH, which comprises contacting TPH with a compound of the invention (i.e., a compound disclosed herein). In a particular method, the TPH is TPH1. In another, the TPH is TPH2. In a particular method, the inhibition is in vitro. In another, the inhibition is in vivo.

One embodiment encompasses a method of inhibiting TPH1 in a mammal (e.g., a human), which comprises administering to the mammal a compound of the invention. In a particular method, TPH2 is not significantly inhibited. In one method, the compound does not readily cross the blood/brain barrier. In another, the compound is a selective inhibitor of TPH1.

This invention encompasses methods of treating, preventing and managing various diseases and disorders mediated by peripheral serotonin, which comprise inhibiting TPH1 activity in a patient in need of such treatment, prevention or management. In a particular embodiment, the inhibition is accomplished by administering to the patient a therapeutically or prophylactically effective amount of a potent TPH1 inhibitor. Examples of potent TPH1 inhibitors are disclosed herein.

Particular diseases and disorders include carcinoid syndrome and gastrointestinal diseases and disorders. Examples of specific diseases and disorders include abdominal pain (e.g., associated with medullary carcinoma of the thyroid), anxiety, carcinoid syndrome, celiac disease, constipation (e.g., constipation having an iatrogenic cause, and idiopathic constipation), Crohn's disease, depression, diabetes, diarrhea (e.g., bile acid diarrhea, enterotoxin-induced secretory diarrhea, diarrhea having an iatrogenic cause, idiopathic diarrhea (e.g., idiopathic secretory diarrhea), and traveler's diarrhea), emesis, functional abdominal pain, functional anorectal disorders, functional bloating, functional dyspepsia, functional gallbladder disorders, irritable bowel syndrome (IBS; including IBD-d, IBS-c and IBS-a), lactose intolerance, MEN types I and II, nausea, Ogilvie's syndrome, Pancreatic Cholera Syndrome, pancreatic insufficiency, pheochromacytoma, scleroderma, somatization disorder, sphincter of Oddi disorders, ulcerative colitis, and Zollinger-Ellison Syndrome.

Additional diseases and disorders include cardiovascular and pulmonary diseases and disorders, such as acute and chronic hypertension, chronic obstructive pulmonary disease (COPD), pulmonary embolism (e.g., bronchoconstriction and pulmonary hypertension following pulmonary embolism), pulmonary hypertension (e.g., pulmonary hypertension associated with portal hypertension), and radiation pneumonitis (including that giving rise to or contributing to pulmonary hypertension). Others include abdominal migraine, adult respiratory distress syndrome (ARDS), carcinoid crisis, CREST syndrome (calcinosis, Raynaud's phenomenon, esophageal dysfunction, sclerodactyl), telangiectasia), serotonin syndrome, and subarachnoid hemorrhage.

In particular methods of the invention, the treatment, management and/or prevention of a disease or disorder is achieved while avoiding adverse effects associated with alteration of central nervous system (CNS) serotonin levels. Examples of such adverse effects include agitation, anxiety disorders, depression, and sleep disorders (e.g., insomnia and sleep disturbance). In particular methods of the invention, the treatment, management and/or prevention of a disease or disorder is achieved while avoiding adverse effects associated with alteration of central nervous system (CNS) serotonin levels. Examples of such adverse effects include agitation, anxiety disorders, depression, and sleep disorders (e.g., insomnia and sleep disturbance).

5.5. Pharmaceutical Compositions

This invention encompasses pharmaceutical compositions comprising one or more compounds of the invention. Certain pharmaceutical compositions are single unit dosage forms suitable for oral, mucosal (e.g., nasal, sublingual, vaginal, buccal, or rectal), parenteral (e.g., subcutaneous, intravenous, bolus injection, intramuscular, or intraarterial), or transdermal administration to a patient. Examples of dosage forms include, but are not limited to: tablets; caplets; capsules, such as soft elastic gelatin capsules; cachets; troches; lozenges; dispersions; suppositories; ointments; cataplasms (poultices); pastes; powders; dressings; creams; plasters; solutions; patches; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; and sterile solids (e.g., crystalline or amorphous solids) that can be reconstituted to provide liquid dosage forms suitable for parenteral administration to a patient.

The formulation should suit the mode of administration. For example, the oral administration of a compound susceptible to degradation in the stomach may be achieved using an enteric coating. Similarly, a formulation may contain ingredients that facilitate delivery of the active ingredient(s) to the site of action. For example, compounds may be administered in liposomal formulations in order to protect them from degradative enzymes, facilitate transport in circulatory system, and effect their delivery across cell membranes.

Similarly, poorly soluble compounds may be incorporated into liquid dosage forms (and dosage forms suitable for reconstitution) with the aid of solubilizing agents, emulsifiers and surfactants such as, but not limited to, cyclodextrins (e.g., α-cyclodextrin, β-cyclodextrin, Captisol®, and Encapsin™ (see, e.g., Davis and Brewster, *Nat. Rev. Drug Disc.* 3:1023-1034 (2004)), Labrasol®, Labrafil®, Labrafac®, cremafor, and non-aqueous solvents, such as, but not limited to, ethyl alcohol, isopropyl alcohol, ethyl carbonate, ethyl acetate, benzyl alcohol, benzyl benzoate, propylene glycol, 1,3-butylene glycol, dimethyl formamide, dimethyl sulfoxide (DMSO), biocompatible oils (e.g., cottonseed, groundnut, corn, germ, olive, castor, and sesame oils), glycerol, tetrahydrofurfuryl alcohol, polyethylene glycols, fatty acid esters of sorbitan, and mixtures thereof (e.g., DMSO:cornoil).

Poorly soluble compounds may also be incorporated into suspensions using other techniques known in the art. For example, nanoparticles of a compound may be suspended in a liquid to provide a nanosuspension (see, e.g., Rabinow, *Nature Rev. Drug Disc.* 3:785-796 (2004)). Nanoparticle forms of compounds described herein may be prepared by the methods described in U.S. Patent Publication Nos. 2004-0164194, 2004-0195413, 2004-0251332, 2005-0042177 A1, 2005-0031691 A1, and U.S. Pat. Nos. 5,145,684, 5,510,118, 5,518,187, 5,534,270, 5,543,133, 5,662,883, 5,665,331, 5,718,388, 5,718,919, 5,834,025, 5,862,999, 6,431,478, 6,742,734, 6,745,962, the entireties of each of which are incorporated herein by reference. In one embodiment, the nanoparticle form comprises particles having an average particle size of less than about 2000 nm, less than about 1000 nm, or less than about 500 nm.

The composition, shape, and type of a dosage form will typically vary depending with use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. How to account for such differences will be apparent to those skilled in the art. See, e.g., *Remington's Pharmaceutical Sciences*, 18th ed., Mack Publishing, Easton Pa. (1990).

5.5.1. Oral Dosage Forms

Pharmaceutical compositions of the invention suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences*, 18th ed., Mack Publishing, Easton Pa. (1990).

Typical oral dosage forms are prepared by combining the active ingredient(s) in an intimate admixture with at least one excipient according to conventional pharmaceutical compounding techniques. Excipients can take a wide variety of forms depending on the form of preparation desired for administration.

Because of their ease of administration, tablets and capsules represent the most advantageous oral dosage unit forms. If desired, tablets can be coated by standard aqueous or non-aqueous techniques. Such dosage forms can be prepared by conventional methods of pharmacy. In general, pharmaceutical compositions and dosage forms are prepared by uniformly and intimately admixing the active ingredients with liquid carriers, finely divided solid carriers, or both, and then shaping the product into the desired presentation if necessary. Disintegrants may be incorporated in solid dosage forms to facility rapid dissolution. Lubricants may also be incorporated to facilitate the manufacture of dosage forms (e.g., tablets).

5.5.2. Parenteral Dosage Forms

Parenteral dosage forms can be administered to patients by various routes including subcutaneous, intravenous (including bolus injection), intramuscular, and intraarterial. Because their administration typically bypasses patients' natural defenses against contaminants, parenteral dosage forms are specifically sterile or capable of being sterilized prior to administration to a patient. Examples of parenteral dosage forms include solutions ready for injection, dry products ready to be dissolved or suspended in a pharmaceutically acceptable vehicle for injection, suspensions ready for injection, and emulsions.

Suitable vehicles that can be used to provide parenteral dosage forms of the invention are well known to those skilled in the art. Examples include: Water for Injection USP; aqueous vehicles such as Sodium Chloride Injection, Ringer's Injection, Dextrose Injection, Dextrose and Sodium Chloride Injection, and Lactated Ringer's Injection; water-miscible vehicles such as ethyl alcohol, polyethylene glycol, and polypropylene glycol; and non-aqueous vehicles such as corn oil, cottonseed oil, peanut oil, sesame oil, ethyl oleate, isopropyl myristate, and benzyl benzoate.

6. EXAMPLES

6.1. Production of tph1 Gene Disrupted Mice

Exon 3 of the murine TPH1 gene was removed by gene targeting essentially as described by Wattler et al., *Biotechniques* 26(6): 1150-6 (1999). The resulting knockout animals displayed normal TPH activity in the brain but drastically reduced TPH expression in the gut.

6.2. Physiological Effects of tph1 Gene Disruption

Mice homozygous (−/−) for the disruption of tph1 were studied in conjunction with mice heterozygous (+/−) for the disruption of the gene, along with wild-type (+/+) litter mates. During this analysis, the mice were subject to a medical work-up using an integrated suite of medical diagnostic procedures designed to assess the function of the major organ systems in a mammalian subject. By studying the homozygous (−/−) knockout mice in the described numbers and in conjunction with heterozygous (+/−) and wild-type (+/+) litter mates, more reliable and repeatable data was obtained.

Disruption of tph1 gene primarily affected the GI tract isoform of TPH (TPH1), and had little or no effect on the brain isoform of TPH (TPH2). Disruption of the gene caused no measurable adverse effects on the central nervous system. This was confirmed by serotonin immunochemistry, which showed that serotonin was greatly reduced or absent in the stomach, duodenum, jejunum, ileum, cecum and colon, while serotonin levels were unaffected in raphe neurons.

Some mice homozygous (−/−) for the disruption of the tph1 gene exhibited a decrease in thrombosis without a significant increase in bleeding or other adverse indications.

6.3. HPLC Characterization

In some of the following synthetic examples, high performance liquid chromatography (HPLC) retention times are provided. The various conditions used to obtain those retention times are described below:

Method A: YMC-PACK ODS-A 3.0×50 mm; Solvent A=$H_2O$, 0.1% TFA; Solvent B=MeOH, 0.1% TFA; B % from 10 to 90% over 4 min.; flow rate=2 ml/min.; observation wavelength=220 and 254 nm.

Method B: YMC-PACK ODS-A 3.0×50 mm; Solvent A=90% water, 10% MeOH with 0.1% TFA; Solvent B=90% MeOH, 10% water with 0.1% TFA; B % from 0 to 100% over 4 min.; flow, rate=2 ml/min.; observation wavelength=220 and 254 nm.

Method C: ShimPack VP ODS 4.6×50 mm; Solvent A=90% $H_2O$, 10% MeOH, 1% TFA; Solvent B=10% $H_2O$, 90% MeOH, 1% TFA; B % from 0 to 100% over 2 min.; flow rate=3.5 ml/min.; observation wavelength=220 and 254 nm.

Method D: Shim VP ODS 4.6×50 mm; Solvent A=$H_2O$ with 0.1% TFA; Solvent B=MeOH with 0.1% TFA; B % from 0 to 100% over 4 min.; flow rate=3 ml/min.; observation wavelength=254 nm.

Method E: YMC Pack ODS-A 4.6×33 mm; Solvent A=$H_2O$, 0.1% TFA; Solvent B=MeOH with 0.1% TFA; B % from 10 to 90% over 3 min.; flow rate 2 ml/min.; observation wavelength 220 and 254 nm.

Method F: YMC-Pack ODS-A 3.0×50 mm; Solvent A=90% $H_2O$, 10% MeOH, 1% TFA; Solvent B=10% $H_2O$, 90% MeOH, 1% TFA; B % from 10 to 90% over 4 min.; flow rate=2 ml/min. observation wavelength=220 and 254 nm.

6.4. Synthesis of (S)-2-Amino-3-(4-{2-amino-6-[2,2,2-trifluoro-1-(4-pyridin-4-yl-phenyl)-ethoxy]-pyrimidin-4-yl}-phenyl)-propionic acid

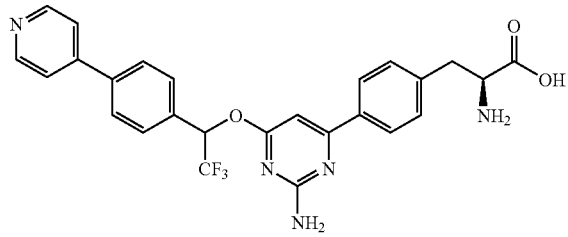

Tetrabutylammonium fluoride (0.027 ml; 1.0 M solution in tetrahydrofuran) was added to a solution of 4-pyridin-4-yl-benzaldehyde (500 mg, 2.73 mmol) and trifluoromethyltrimethylsilane (TMSCF₃) (485 µl, 3.28 mmol) in 5 ml THF at 0° C. The resulting mixture was warmed up to room temperature and stirred at room temperature for 4 hours. The reaction mixture was then treated with 5 ml of 1N HCl and stirred at room temperature overnight. The solvent was evaporated to dryness, 9 ml of 1M sodium carbonate aqueous solution was added, the aqueous phase was extracted with chloroform (3×10 ml), and the combined chloroform layer was washed with water, dried over MgSO₄. The organic solvent was removed in vacuo to give 360 mg of 2,2,2-trifluoro-1-(4-pyridin-4-yl-phenyl)ethanol, yield: 51%.

The mixture of 2,2,2-trifluoro-1-(4-pyridin-4-yl-phenyl)ethanol (100 mg, 0.40 mmol), 2-amino-4,6-dichloropyrimidine (60 mg, 0.38 mmol), and cesium carbonate (468 mg, 1.44 mmol) was dissolved in 2 ml of 1,4-dioxane in a 50 ml sealed tube. The mixture was heated at 110° C. overnight, then was cooled to room temperature; 10 ml of ethyl acetate was added and then filtered through Celite. The filtrate was concentrated to give 120 mg of 4-chloro-6-[2,2,2-trifluoro-1-(4-pyridin-4-yl-phenyl)-ethoxy]-pyrimidin-2-ylamine, yield: 80%.

In a microwave vial, 4-chloro-6-[2,2,2-trifluoro-1-(4-pyridin-4-yl-phenyl)-ethoxy]-pyrimidin-2-ylamine (30 mg, 0.080 mmol), 4-borono-L-phenylalanine (21 mg, 0.098 mmol) and 1 ml of actonitrile, and 0.7 ml of water were mixed together. Then, 0.3 ml of 1N aqueous sodium carbonate was added to mixture, followed by 5 mole percent of dichlorobis-(triphenylphosphine)-palladium(II). The reaction vessel was sealed and heated at 150° C. for 5 minutes with microwave irradiation. After cooling, the reaction mixture was evaporated to dryness. The residue was dissolved in 2.5 ml of methanol, and then was purified by Prep-LC to give 6.7 mg of (S)-2-Amino-3-(4-{2-amino-6-[2,2,2-trifluoro-1-(4-pyrimidin-4-yl-phenyl)-ethoxy]-pyrimidin-4-yl}-phenyl)-propionic acid. ¹H NMR (400 MHz, CD₃OD) δ (ppm) 8.82 (s, 2H), 8.26 (s, 2H), 8.02 (d, J=8 Hz, 2H), 7.97 (d, J=8.4 Hz, 2H), 7.86 (d, J=8.4 Hz, 2H), 7.45 (d, J=8 Hz 2H), 6.89 (q, J=6.8 Hz, 1H), 6.81 (d, J=2 Hz, 1H), 4.29 (t, J=1.6 Hz, 1H), 3.39 (m, 1H), 3.19 (m, 1H).

6.5. Synthesis of (S)-2-Amino-3-(4-{6-[2,2,2-trifluoro-1-(2-pyridin-4-yl-phenyl)-ethoxy]-pyrimidin-4-yl}-phenyl)-propionic acid

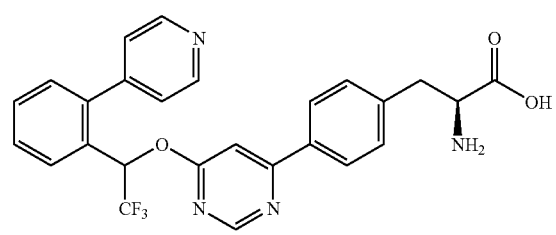

Tetrabutylammonium fluoride (0.027 ml; 1.0 M solution in tetrahydrofuran) was added to a solution of 2-pyridin-4-yl-benzaldehyde (500 mg, 2.73 mmol) and trifluoromethyltrimethylsilane (TMSCF₃) (485 µl, 3.28 mmol) in 5 ml of THF at 0° C. The formed mixture was warmed up to room temperature and stirred at room temperature for 4 hours. The reaction mixture was then treated with 5 ml of 1N HCl and stirred at room temperature overnight. The solvent was evaporated to dryness, 9 ml of 1M sodium carbonate aqueous solution was added, the aqueous phase was extracted with chloroform (3×10 ml), and the combined organic layer was washed with water, dried over MgSO₄. The organic solvent was evaporated to give 300 mg of 2,2,2-trifluoro-1-(2-pyridin-4-yl-phenyl)ethanol, yield: 43%.

The mixture of 2,2,2-trifluoro-1-(2-pyridin-4-yl-phenyl)ethanol (100 mg, 0.40 mmol), 4,6-dichloro-pyrimidine (54 mg, 0.38 mmol), cesium carbonate (468 mg, 1.44 mmol) and 1,4-dioxane (1 ml). The mixture was heated at 110° C. overnight. The reaction mixture was cooled to room temperature. 10 ml of ethyl acetate was added, and then the mixture was filtered through Celite. The filtrate was concentrated to give 110 mg of 4-chloro-6-[2,2,2-trifluoro-1-(2-pyridin-4-yl-phenyl)-ethoxy]-pyrimidine, yield: 76%.

In a microwave vial 4-chloro-6-[2,2,2-trifluoro-1-(4-pyridin-4-yl-phenyl)-ethoxy]-pyrimidine (30 mg, 0.082 mmol), 4-borono-L-phenylalanine (21 mg, 0.098 mmol), 1 ml of actonitrile and 0.7 ml of water were mixed together. Then, 0.3 ml of 1N aqueous sodium carbonate was added to the mixture, followed by 5 mole percent of dichlorobis-(triphenylphosphine)-palladium(II). The reaction vessel was sealed and heated at 150° C. for 5 minutes with microwave irradiation. After cooling, the reaction mixture was evaporated to dryness. The residue was dissolved in 2.5 ml of methanol, and then was purified by Prep-LC to give 19 mg of (S)-2-Amino-3-(4-{6-[2,2,2-trifluoro-1-(2-pyridin-4-yl-phenyl)-ethoxy]-pyrimidin-4-yl}-phenyl)-propionic acid. ¹H NMR (400 MHz, CD₃OD) δ (ppm) 8.94 (d, J=6 Hz, 2H), 8.79 (d, J=1.2 Hz, 1H), 8.15 (m, 4H), 7.84 (t, J=5.2 Hz, 1H), 7.62 (m, 3H), 7.46 (m, 3H). 6.66 (q, J=6.4 Hz, 1H), 4.31 (q, J=6 Hz, 1H), 3.41 (m, 1H), 3.26 (m, 1H).

6.6. Synthesis of (S)-2-Amino-3-(4-{2-amino-6-[2,2,2-trifluoro-1-(2-(4-methyl-thiophen-3-yl)-phenyl]-ethoxy}-pyrimidin-4-yl)-phenyl]-propionic acid

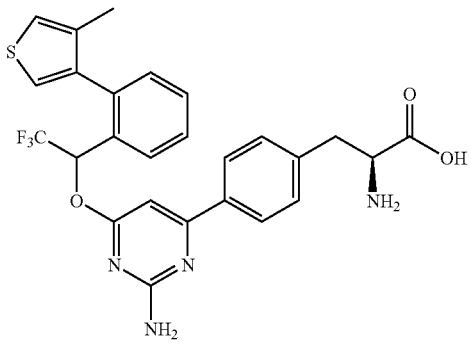

In a microwave vial, 3-bromo-4-methyl-thiophene (653 mg, 3.69 mmol), 2-formyl phenylboronic acid (500 mg, 3.36 mmol) and 7 ml of actonitrile were mixed together. 6.7 ml of 1N aqueous sodium carbonate was added to above solution, followed by 5 mole percent of dichlorobis(triphenylphosphine)-palladium(II). The reaction vessel was sealed and heated at 150° C. for 5 minutes with microwave irradiation. After cooling, 50 ml of ethyl acetate was added, the organic layer was separated, washed with water, dried with sodium sulfate. The organic solvent was evaporated to give crude product, which was purified by ISCO CombiFlash column to give 530 mg of 2-(4-methyl-thiophen-3-yl)benzaldehyde, yield: 78%.

Tetrabutylammonium fluoride (0.013 ml; 1.0 M solution in tetrahydrofuran) was added to a solution of 2-(4-methylthiophen-3-yl)-benzaldehyde (260 mg, 1.29 mmol) and trifluoromethyltrimethylsilane (TMSCF$_3$) (228 µl, 1.54 mmol) in 5 ml of THF at 0° C. The formed mixture was warmed up to room temperature and stirred at room temperature for 4 hours. The reaction mixture was then treated with 5 ml of 1N HCl and stirred at room temperature overnight. The product was extracted with ethyl acetate (3×50 ml). The organic layer was separated and dried over sodium sulfate. The organic solvent was evaporated to give 340 mg of 2,2,2-trifluoro-1-[2-(4-methyl-thiophen-3-yl)-phenyl]-ethanol, yield 97%.

A mixture of 2,2,2-trifluoro-1-[2-(4-methyl-thiophen-3-yl)-phenyl]-ethanol (100 mg, 0.37 mmol), 2-amino-4,6-dichloro-pyrimidine (54 mg, 0.33 mmol), cesium carbonate (481 mg, 1.48 mmol) and 1,4-dioxane (1 ml) was heated at 110° C. overnight. The reaction mixture was cooled to room temperature; 10 ml of ethyl acetate was added. The mixture was then filtered through Celite, the filtrate was concentrated to give 100 mg of 4-chloro-6-{2,2,2-trifluoro-1-[2-(4-methyl-thiophen-3-yl)-phenyl]-ethoxy}-pyrimidin-2-ylamine, yield: 76%.

In a microwave vial, 4-chloro-6-{2,2,2-trifluoro-1-[2-(4-methyl-thiophen-3-yl)-phenyl]-ethoxy}-pyrimidin-2-ylamine (30 mg, 0.075 mmol), 4-borono-L-phenylalanine (19 mg, 0.09 mmol), 1 ml of actonitrile and 0.7 ml of water were mixed. 0.3 ml of 1N aqueous sodium carbonate was added to mixture, followed by 5 mole percent of dichlorobis-(triphenylphosphine)-palladium(II). The reaction vessel was sealed and heated at 150° C. for 5 minutes with microwave irradiation. After cooling, the reaction mixture was evaporated to dryness. The residue was dissolved in 2.5 ml of methanol, and then was purified by Prep HPLC to give 15.1 mg of (S)-2-amino-3-(4-{2-amino-6-[2,2,2-trifluoro-1-(2-(4-methyl-thiophen-3-yl)-phenyl]-ethoxy}-pyrimidin-4-yl}-phenyl)-propionic acid. $^1$H NMR (400 MHz, CD$_3$OD) δ (ppm) 7.94 (d, J=8 Hz, 2H), 7.80 (s, 1H), 7.50 (m, 5H), 7.25 (m, 2H), 7.03 (s, 1H), 6.94 (s, 1H), 4.31 (t, J=5.6, 1H), 3.48 (m, 1H), 3.26 (m, 1H), 1.98 (s, 3H).

6.7. Synthesis of (S)-2-Amino-3-(4-{2-amino-6-[2,2,2-trifluoro-1-(2-(5-methyl-thiophen-3-yl)-phenyl]-ethoxy}-pyrimidin-4-yl)-phenyl]-propionic acid

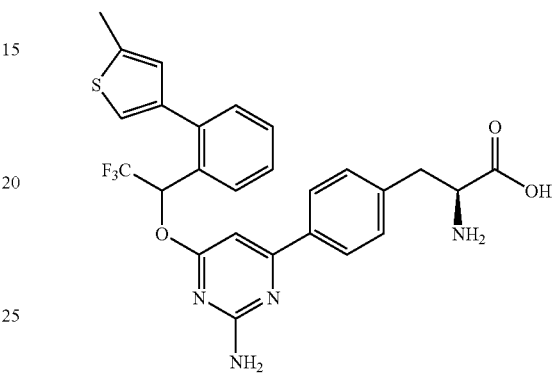

In a microwave vial, 4-bromo-2-methyl-thiophene (653 mg, 3.69 mmol), 2-formyl phenylboronic acid (500 mg, 3.36 mmol) and 7 ml of actonitrile were mixed. 6.7 ml of 1N aqueous sodium carbonate was added to above solution, followed by 5 mole percent of dichlorobis(triphenylphosphine)-palladium(II). The reaction vessel was sealed and heated at 150° C. for 5 minutes with microwave irradiation. After cooling, 50 ml of ethyl acetate was added, the organic layer was separated, washed with water, dried with sodium sulfate, the organic solvent was evaporated and the residue was purified by ISCO to give 550 mg of 2-(5-methyl-thiophen-3-yl)benzaldehyde, yield 81%.

Tetrabutylammonium fluoride (0.028 ml; 1.0 M solution in tetrahydrofuran) was added to a solution of 2-(5-methylthiophen-3-yl)-benzaldehyde (550 mg, 1.29 mmol) and trifluoromethyltrimethylsilane (TMSCF$_3$) (483 µl, 3.27 mmol) in 10 ml of THF at 0° C. The formed mixture was warmed up to room temperature and stirred at room temperature for 4 hours. The reaction mixture was then treated with 10 ml of 1N HCl and stirred at room temperature overnight. The product was extracted with ethyl acetate (3×50 ml). The organic layer was separated and dried over sodium sulfate. The organic solvent was evaporated to give 650 mg of 2,2,2-trifluoro-1-[2-(5-methyl-thiophen-3-yl)-phenyl]-ethanol, yield: 87%.

A mixture of 2,2,2-trifluoro-1-[2-(5-methyl-thiophen-3-yl)-phenyl]-ethanol (100 mg, 0.37 mmol), 2-amino-4,6-dichloro-pyrimidine (54 mg, 0.33 mmol), cesium carbonate (481 mg, 1.48 mmol) and 1,4-dioxane (2 ml) was heated at 110° C. overnight. The reaction mixture was cooled to room temperature; 10 ml of ethyl acetate was added. The mixture was then filtered through Celite, the filtrate was concentrated to give 90 mg of 4-chloro-6-{2,2,2-trifluoro-1-[2-(5-methyl-thiophen-3-yl)-phenyl]-ethoxy}-pyrimidin-2-ylamine, yield: 68%

In a microwave vial, 4-chloro-6-{2,2,2-trifluoro-1-[2-(5-methyl-thiophen-3-yl)-phenyl]-ethoxy}-pyrimidin-2-ylamine (30 mg, 0.075 mmol), 4-borono-L-phenylalanine (19 mg, 0.09 mmol), 1 ml of actonitrile and 0.7 ml of water were mixed. 0.3 ml of 1N aqueous sodium carbonate was added to the mixture, followed by 5 mole percent of dichlorobis-(triphenylphosphine)-palladium(II). The reaction vessel was sealed and heated at 150° C. for 5 minutes with microwave irradiation. After cooling, the reaction mixture was evaporated to dryness. The residue was dissolved in 2.5 ml of methanol, and then was purified by Prep-LC to give 10.1 mg of (S)-2-Amino-3-(4-{2-amino-6-[2,2,2-trifluoro-1-(2-(5-methyl-thiophen-3-yl)-phenyl]-ethoxy}-pyrimidin-4-yl}-phenyl)-propionic acid. $^1$H NMR (400 MHz, CD$_3$OD) δ (ppm) 7.83 (d, J=8.4 Hz, 2H), 7.63 (d, J=7.2 Hz, 1H), 7.34 (m, 4H), 7.26 (m, 1H), 7.12 (d, J=1.2 Hz, 1H), 6.92 (q, J=6.8, 1H), 6.82 (d, J=1.2 Hz, 1H), 6.64 (s, 1H), 4.21 (t, J=5.6 Hz, 1H), 3.29 (m, 1H), 3.20 (m, 1H), 2.47 (s, 3H).

6.8. Synthesis of (S)-2-Amino-3-(4-{2-amino-6-[2,2,2-trifluoro-1-(4-furan-3-yl-phenyl)-ethoxy]-pyrimidin-4-yl}-phenyl)-propionic acid

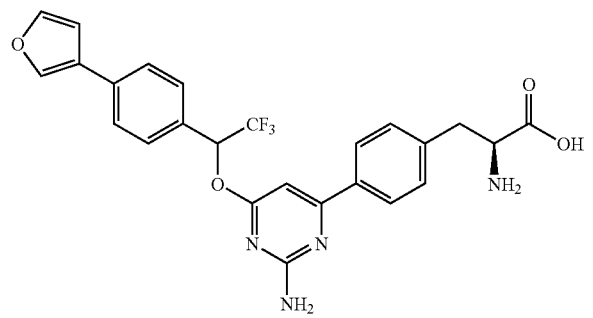

In a microwave vial, 3-bromo-furan (590 mg, 4.02 mmol), 4-formyl phenylboronic acid (600 mg, 4.02 mmol) and 7 ml of actonitrile were mixed. 8 ml of 1N aqueous sodium carbonate was then added to the mixture, followed by 5 mole percent of dichlorobis-(triphenylphosphine)-palladium(II). The reaction vessel was sealed and heated at 150° C. for 7 minutes with microwave irradiation. After cooling, 50 ml of ethyl acetate was added, the organic layer was separated, washed with water, dried over sodium sulfate. The organic solvent was evaporated to give crude product, which was purified by ISCO to give 410 mg of 4-furan-3-yl-benzaldehyde, yield: 60%.

Tetrabutylammonium fluoride (0.024 ml; 1.0 M solution in tetrahydrofuran) was added to a solution of 4-furan-3-yl-benzaldehyde (410 mg, 2.38 mmol) and trifluoromethyltrimethylsilane (TMSCF$_3$) (423 µl, 2.86 mmol) in 5 ml THF at 0° C. The formed mixture was warmed up to room temperature and stirred at room temperature for 4 hours. The reaction mixture was then treated with 5 ml of 1N HCl and stirred at room temperature overnight. The product was extracted with ethyl acetate (3×50 ml). The organic layer was separated and dried over sodium sulfate. The organic solvent was evaporated to give 480 mg of 2,2,2-trifluoro-1-(4-furan-3-yl-phenyl)-ethanol, yield: 83%.

The mixture of 2,2,2-trifluoro-1-(4-furan-3-yl-phenyl)-ethanol (100 mg, 0.4 mmol), 2-amino-4,6-dichloro-pyrimidine (60 mg, 0.36 mmol), cesium carbonate (468 mg, 1.44 mmol) and 1,4-dioxane (1 ml) was heated at 110° C. overnight. The reaction mixture was cooled to room temperature; 10 ml of ethyl acetate was added. The mixture was then filtered through Celite, the filtrate was concentrated to give 110 mg of 4-chloro-6-[2,2,2-trifluoro-1-(4-furan-3-yl-phenyl)-ethoxy]-pyrimidin-2-ylamine, yield: 72%.

In a microwave vial, 4-chloro-6-[2,2,2-trifluoro-1-(4-furan-3-yl-phenyl)-ethoxy]-pyrimidin-2-ylamine (30 mg, 0.081 mmol), 4-borono-L-phenylalanine (20 mg, 0.098 mmol), 1 ml of actonitrile and 0.7 ml of water were mixed. Then, 0.3 ml of 1N aqueous sodium carbonate was added to the mixture, followed by 5 mole percent of dichlorobis-(triphenylphosphine)-palladium(II). The reaction vessel was sealed and heated at 150° C. for 5 minutes with microwave irradiation. After cooling, the reaction mixture was evaporated to dryness. The residue was dissolved in 2.5 ml of methanol, and then was purified by Prep-LC to give 7.2 mg of (S)-2-amino-3-(4-{2-amino-6-[2,2,2-trifluoro-1-(4-furan-3-yl-phenyl)-ethoxy]-pyrimidin-4-yl}-phenyl)-propionic acid. $^1$H NMR (400 MHz, CD$_3$OD) δ (ppm) 7.96 (m, 3H), 7.61 (m, 5H), 6.81 (s, 1H), 6.77 (d, J=6.8 Hz, 1H), 6.74 (d, J=4.8 Hz, 1H), 4.27 (q, J=5.6 Hz, 1H), 3.36 (m, 1H), 3.21 (m, 1H).

6.9. Synthesis of (S)-2-Amino-3-[4-{2-amino-6-{1-[2-(5-dimethylaminomethyl-furan-2-yl)-phenyl]-2,2,2-trifluoro-ethoxy}-pyrimidin-4-yl)-phenyl]-propionic acid

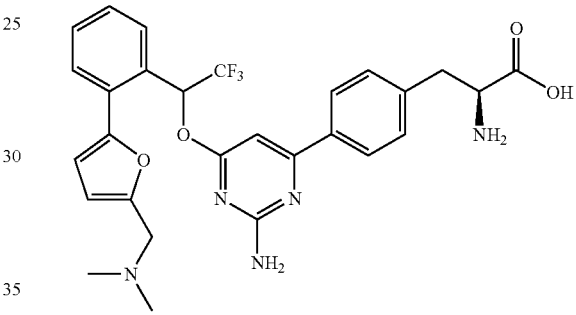

Sodium triacetoxyborohydride (844 mg, 4 mmol) was added to a solution of 5-bromo-furan-2-carbaldehyde (350 mg, 2 mmol) and dimethyl amine (2 ml, 2M solution in THF) in 10 ml of 1,2-dichloroethane (DCE). 0.2 ml of HOAc was then added. The mixture was stirred at room temperature overnight, followed by addition of 15 ml of DCE. The organic phase was washed with water, dried over sodium sulfate. The solvent was removed by rotovap to give 400 mg of (5-bromo-furan-2-ylmethyl)-dimethyl-amine, yield: 97%.

In a microwave vial, (5-bromo-furan-2-ylmethyl)-dimethyl-amine (385 mg, 1.88 mmol), 2-formyl phenylboronic acid (288 mg, 1.93 mmol) and 3.7 ml of actonitrile were mixed. Then, 3.7 ml of 1N aqueous sodium carbonate was added to the mixture, followed by 5 mole percent of dichlorobis(triphenylphosphine)-palladium(II). The reaction vessel was sealed and heated at 150° C. for 5 minutes with microwave irradiation. After cooling, 20 ml of 1N HCl was added. The mixture was extracted by ethyl acetate (3×10 ml) and the ethyl acetate layer was discarded. 1N NaOH solution was added to aqueous phase to adjust pH to 10, then extracted with ethyl acetate (3×20 ml). The combined organic layer was washed with water and dried over sodium sulfate. The solvent was evaporated to give 300 mg of 2-(4-dimethylaminomethyl-cyclopenta-1,3-dienyl)-benzaldehyde, yield: 69%.

Tetrabutylammonium fluoride (0.013 ml; 1.0 M solution in tetrahydrofuran) was added to a solution of 2-(4-dimethylaminomethyl-cyclopenta-1,3-dienyl)-benzaldehyde (287 mg, 1.25) and trifluoromethyltrimethylsilane (TMSCF$_3$) (222 µl, 1.5 mmol) in 5 ml THF at 0° C. The formed mixture was warmed up to room temperature and stirred at room temperature for 4 hours. The reaction mixture was then treated with 5 ml of 1N HCl and stirred at room temperature overnight. The product was extracted with ethyl acetate (3×50 ml). The organic layer was separated and dried over sodium sulfate. The organic solvent was evaporated to give 250 mg of 1-[2-(5-dimethylaminomethyl-furan-2-yl)-phenyl]-2,2,2-trifluoro-ethanol, yield 66%.

The mixture of 1-[2-(5-dimethylaminomethyl-furan-2-yl)-phenyl]-2,2,2-trifluoro-ethanol (225 mg, 0.75 mmol), 2-amino-4,6-dichloro-pyrimidine (111 mg, 0.67 mmol), cesium carbonate (978 mg, 3.01 mmol) and 1,4-dioxane (3 ml) was heated at 110° C. overnight. The reaction mixture was cooled to room temperature; 10 ml of ethyl acetate was added. The mixture was then filtered through Celite, the filtrate was concentrated to give 110 mg of 4-chloro-6-{1-[2-(5-dimethylaminomethyl-furan-2-yl)-phenyl]2,2,2-trifluoro-ethoxy}-pyrimidin-2-ylamine, yield 87%.

In a microwave vial, 4-chloro-6-{1-[2-(5-dimethylaminomethyl-furan-2-yl)-phenyl]2,2,2-trifluoro-ethoxy}-pyrimidin-2-ylamine (37 mg, 0.087 mmol), 4-borono-L-phenylalanine (22 mg, 0.10 mmol), 1 ml of actonitrile and 0.7 ml of water were mixed. Then, 0.3 ml of 1N aqueous sodium carbonate was added, followed by 5 mole percent of dichlorobis(triphenylphosphine)-palladium(II). The reaction vessel was sealed and heated at 150° C. for 5 minutes with microwave irradiation. After cooling, the reaction mixture was evaporated to dryness. The residue was dissolved in 2.5 ml of methanol, and then was purified by Prep-LC to give 16 mg of (S)-2-amino-3-[4-{2-amino-6-{1-[2-(5-dimethylaminomethyl-furan-2-yl)-phenyl]-2,2,2-trifluoro-ethoxy}-pyrimidin-4-yl]-phenyl]-propionic acid. $^1$H NMR (400 MHz, CD$_3$OD) δ (ppm) 7.88 (d, J=8.4 Hz, 2H), 7.71 (d, J=7.6 Hz, 1H), 7.62 (d, J=7.6 Hz, 1H), 7.42 (m, 2H), 7.40 (d, J=1.6 Hz, 2H), 7.34 (d, J=8.4 Hz, 1H), 6.89 (q, J=3.6 Hz, 2H), 6.66 (s, 1H), 4.54 (s, 2H), 4.20 (q, J=6 Hz, 1H), 3.3 (m, 1H), 3.14 (m, 1H), 2.84 (s, 6H).

6.10. Synthesis of (S)-2-Amino-3[4-(2-amino-6-{1-[2-(6-cyano-pyridin-3-yl)-phenyl]-2,2,2-trifluoro-ethoxy}-pyrimidin-4-yl)-phenyl]-propionic acid

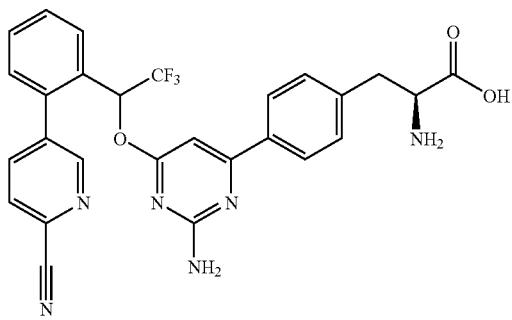

In a microwave vial, 5-(4,4,5,5-tetramethyl-[1,3,2]dioxaborolan-2-yl)-pyridine-2-carbonitrile (279 mg, 1.51 mmol), 2-bromo-benzaldehyde (230 mg, 1 mmol) and 2 ml of actonitrile were mixed. Then, 2 ml of 1N aqueous sodium carbonate was added, followed by 5 mole percent of dichlorobis(triphenylphosphine)-palladium(II). The reaction vessel was sealed and heated at 100° C. for 10 minutes with microwave irradiation. After cooling, 50 ml of ethyl acetate was added, the organic layer was separated, washed with water and dried over sodium sulfate. The organic solvent was evaporated to give crude product which was purified by ISCO to give 150 mg of 5-(2-formyl-phenyl)-pyridine-2-carbonitrile, yield 72%.

Tetrabutylammonium fluoride (5.3 μl, 1.0 M solution in tetrahydrofuran) was added to a solution of 5-(2-formyl-phenyl)-pyridine-2-carbonitrile (110 mg, 0.53 mmol) and trifluoromethyltrimethylsilane (120 μl, 0.81 mmol) in 5 ml THF at 0° C. The formed mixture was warmed up to room temperature and stirred at room temperature for 4 hours. The reaction mixture was then treated with 5 ml of 1N HCl and stirred at room temperature overnight. The product was extracted with ethyl acetate (3×50 ml). The organic layer was separated and dried over sodium sulfate. The organic solvent was evaporated to give 140 mg of 5-[2-(2,2,2-trifluoro-1-hydroxy-ethyl)-phenyl]-pyridine-2-carbonitrile, yield 95%.

A mixture of 5-[2-(2,2,2-trifluoro-1-hydroxy-ethyl)-phenyl]-pyridine-2-carbonitrile (46 mg, 0.165 mmol), (S)-3-[4-(2-amino-6-chloro-pyrimidin-4-yl)-phenyl]-2-tert-butoxycarbonylamino-propionic acid (59 mg, 0.15 mmol), cesium carbonate (195 mg, 0.6 mmol) and 1,4-dioxane (1 ml) was heated at 110° C. overnight. The reaction mixture was cooled to room temperature, then was poured into 5 ml of water. 1N HCl was added to adjust pH to 4.5, the aqueous phase was extracted with ethyl acetate (3×10 ml). The combined organic layer was washed with brine and dried over sodium sulfate. The solvent was evaporated to give 80 mg of crude (S)-3-[4-(2-amino-6-{1-[2-(6-cyanopyridin-3-yl)-phenyl]-2,2,2-trifluoro-ethoxy}-pyrimidin-4-yl)-phenyl]-2-tert-butoxycarbonylamino-propionic acid, yield 84%.

80 mg of (S)-3-[4-(2-amino-6-{1-[2-(6-cyanopyridin-3-yl)-phenyl]-2,2,2-trifluoro-ethoxy}-pyrimidin-4-yl)-phenyl]-2-tert-butoxycarbonylamino-propionic acid was dissolved in the solution of 30% trifluoro acetic acid in dichloromethane (5 ml). The mixture was stirred at room temperature for 1 hour. The solvent was evaporated and the residue was purified by preparative HPLC to give 12.6 mg of (S)-2-amino-3[4-(2-amino-6-{1-[2-(6-cyano-pyridin-3-yl)-phenyl]-2,2,2-trifluoro-ethoxy}-pyrimidin-4-yl)-phenyl]-propionic acid. $^1$H NMR (400 MHz, CD$_3$OD) δ (ppm) 8.86 (s, 1H), 8.17 (d, J=2 Hz, 1H), 8.15 (d, J=2 Hz, 1H), 7.96 (m, 2H), 7.59 (m, 1H), 7.36 (m, 3H), 6.7 (s, 1H), 6.65 (d, J=6.8 Hz, 1H), 4.25 (m, 1H), 3.47 (m, 1H), 3.23 (m, 1H).

6.11. Synthesis of (S)-2-Amino-3-(4-{2-amino-6-[2,2,2-trifluoro-1-(2-imidazol-1-yl-phenyl)-ethoxy]-pyrimidin-4-yl}-phenyl)-propionic acid

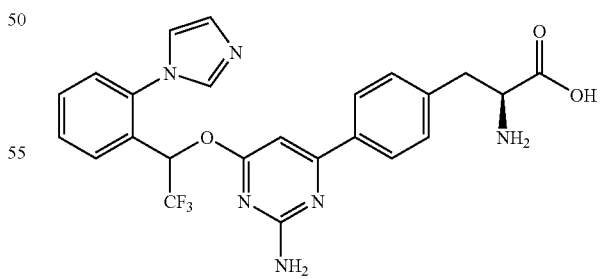

To 2-imidazol-1-yl-benzaldehyde (0.344 g, 2 mmol) in THF (8 ml) was added trifluoromethyltrimethyl silane (0.341 g, 2.4 mmol). The reaction mixture was cooled to 0-5° C. (ice water bath) and tetra-n-butyl ammonium fluoride (0.035 ml, 0.035 mmol, 1M in THF) was added. The ice bath was removed, and the mixture was stirred at room temperature for 6 hours. 2N HCl (5 ml) was added, and the reaction mixture was further stirred for 3 hours at room temperature. Solvent was removed on the rotavap under reduced pressure. Crude residue was dissolved in DCM (30 ml), washed with water (20 ml), brine (20 ml) and dried with sodium sulfate. The solvent was removed to give crude 2,2,2-trifluoro-1-(2-imidazol-1-yl-phenyl)-ethanol (0.45 g, 93%), which was directly used in the next step.

2-Amino-4,6-dichloro pyrimidine (0.107 g, 0.65 mmol), 2,2,2-trifluoro-1-(2-imidazol-1-yl-phenyl)-ethanol (0.157 g, 0.65 mmol), and NaH (0.03 g, 0.78 mmol) were added to anhydrous THF (10 ml) under nitrogen. The reaction was stirred at 40-45° C. for 6 h, and was then cooled to room temperature, and quenched with water (0.2 ml). The reaction mixture was concentrated to give crude 4-chloro-6-[2,2,2-trifluoro-1-(2-imidazol-1-yl-phenyl)-ethoxy]-pyrimidin-2-ylamine (0.24 g, >90% pure by LCMS), which was directly used in the following step.

The above crude intermediate (0.24 g), L-p-borono-phenylalanine (0.140 g, 0.67 mmol), sodium carbonate (0.14 g, 1.32 mmol), and dichlorobis(triphenylphosphine)-palladium (II) (15 mg, 0.021 mmol) were dissolved in a mixture of MeCN (2.0 ml) and H$_2$O (2.0 ml) in a microwave vial. The reaction mixture was sealed and stirred in the microwave reactor at 150° C. for 6 min. The mixture was filtered, and the filtrate was concentrated. The residue was dissolved in MeOH and H$_2$O (1:1), and purified by preparative HPLC using MeOH/H$_2$O/TFA as solvent system to give (S)-2-amino-3-(4-[2-amino-6-[2,2,2-trifluoro-1-(2-imidazol-1-yl-phenyl)-ethoxy]-pyrimidin-4-yl]-phenyl-propionic acid as a TFA salt. LCMS: M+1=499. $^1$H-NMR (400 MHz, CD$_3$OD): δ (ppm) 3.20-3.41 (m, 2H), 4.30 (t, 1H), 6.61 (m, 1H), 6.88 (s, 1H), 7.48 (d, 2H), 7.69 (d, 1H), 7.72-7.81 (m, 2H), 7.83 (m, 1H), 7.98 (m, 3H), 8.02 (m, 1H), 9.40 (m, 1H).

6.12. Synthesis of (S)-2-Amino-3-(4-{6-[2,2,2-trifluoro-1-(2-pyrazol-1-yl-phenyl)-ethoxy]-pyrimidin-4-yl}-phenyl)-propionic acid

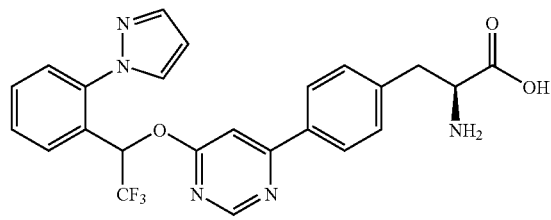

To 2-pyrazol-1-yl-benzaldehyde (0.344 g, 2 mmol) in THF (8 ml) was added trifluoromethyl trimethyl silane (0.341 g, 2.4 mmol). The mixture was cooled to 0-5° C. (ice water bath) and tetra-n-butyl ammonium fluoride (0.035 ml, 0.035 mmol, 1M in THF) was added. The ice bath was removed, and the mixture was stirred at room temperature for 6 h. 2N HCl (5 ml) was added and the reaction mixture was further stirred at room temperature for 3 h. Solvent was removed on the rotavap under reduced pressure. The residue was dissolved in DCM (30 ml), washed with water (20 ml), brine (20 ml) and dried over sodium sulfate. The solvent was removed in vacuo to give crude 2,2,2-trifluoro-1-(2-pyrazol-1-yl-phenyl)-ethanol (0.45 g, 93%) which was directly used in the following experiment.

4,6-Dichloro pyrimidine (0.082 g, 0.55 mmol), 2,2,2-trifluoro-1-(2-pyrazol-1-yl-phenyl)-ethanol (0.121 g, 0.50 mmol), NaH (0.03 g, 0.78 mmol) were added to anhydrous THF (10 ml) under nitrogen atmosphere. The reaction was stirred at 40-45° C. for 6 h, and then was cooled to room temperature, and quenched with water (0.2 ml). The reaction mixture was concentrated to give crude 4-chloro-6-[2,2,2-trifluoro-1-(2-pyrazol-1-yl-phenyl)-ethoxy]-pyrimidine (0.20 g, >90% pure by LCMS), which was directly used in the following step.

The crude intermediate (0.20 g), L-p-borono-phenylalanine (0.105 g, 0.50 mmol), sodium carbonate (0.105 g, 1 mmol), dichlorobis(triphenylphosphine)-palladium(II) (15 mg, 0.021 mmol) were dissolved in a mixture of MeCN (2.0 ml) and H$_2$O (2.0 ml) in a microwave vial. The vial was sealed, and the reaction mixture was heated in microwave reactor at 150° C. for 6 min. The mixture was filtered, and the filtrate was concentrated. The residue was dissolved in MeOH and H$_2$O (1:1), and then purified by preparative HPLC using MeOH/H$_2$O/TFA as solvent system to give (S)-2-amino-3-(4-[6-[2,2,2-trifluoro-1-(2-pyrazol-1-yl-phenyl)-ethoxy]-pyrimidin-4-yl]-phenyl-propionic acid as a TFA salt. LCMS: M+1=484. $^1$H-NMR (400 MHz, CD$_3$OD): δ (ppm) 3.20-3.40 (m, 2H), 4.30 (t, 1H), 6.63 (s, 1H), 7.10 (m, 1H), 7.50 (m, 3H), 7.60 (m, 3H), 7.84 (m, 2H), 8.16 (m, 3H), 8.68 (s, 1H).

6.13. Synthesis of (S)-2-amino-3-[4-(2-amino-6-{2,2,2-trifluoro-1-[2-(3-trifluoromethyl-pyrazol-1-yl)-phenyl]-ethoxy}-pyrimidin-4-yl)-phenyl]-propionic acid

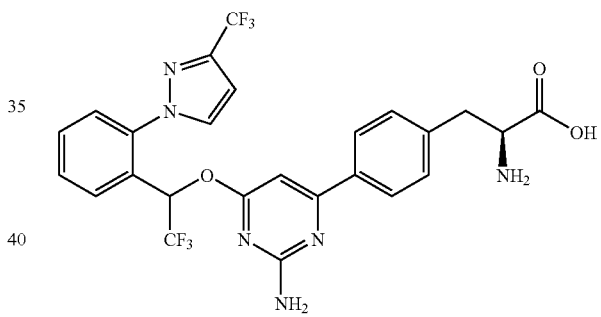

2,2,2-Trifluoro-1-(2-iodo-phenyl)-ethanol (0.331 g, 1.1 mmol), 3-trifluoromethyl pyrazole (0.136 g, 1.0 mmol), CuI (0.019 g, 0.1 mmol), K$_2$CO$_3$ (0.290 g, 2.1 mmol), (1R,2R)-N,N'-dimethyl-cyclohexane-1,2-diamine (0.028 g, 0.2 mmol) and toluene (10 ml) were combined in a 20 ml pressure tube. The mixture was heated at 130° C. (oil bath temperature) for 12 h. The reaction mixture was diluted with ethyl acetate, and washed with H$_2$O (2×20 ml), brine, and dried by sodium sulfate. Removal of solvent gave crude product which was purified by ISCO column chromatography using 5-10% ethyl acetate in hexane as solvent to give 140 mg of 2,2,2-trifluoro-1-[2-(3-trifluoro methyl-pyrazol-1-yl)-phenyl]-ethanol.

2-Amino-4,6-dichloro pyrimidine (0.074 g, 0.45 mmol), 2,2,2-trifluoro-1-[2-(3-trifluoro methyl-pyrazol-1-yl)-phenyl]-ethanol (0.140 g, 0.45 mmol), and NaH (0.022 g, 0.59 mmol) were added to anhydrous THF (10 ml) under nitrogen atmosphere. The reaction was stirred at 40-45° C. for 6 h, and then cooled to room temperature, and quenched with water (0.2 ml). The reaction mixture was concentrated to give crude 4-chloro-6-[2,2,2-trifluoro-1-[2-(3-trifluoromethyl-pyrazol-1-yl)phenyl]-ethoxy]-pyrimidine-2-ylamine (0.21 g, >90% pure by LCMS), which was directly used in the next step.

Crude intermediate (0.21 g), L-p-borono-phenylalanine (0.1 g, 0.48 mmol), sodium carbonate (0.1 g, 0.94 mmol), and dichlorobis(triphenylphosphine)-palladium(II) (15 mg, 0.021 mmol) were dissolved in a mixture of MeCN (2.0 ml) and H$_2$O (2.0 ml) in a microwave vial. The vial was sealed and reaction mixture was heated in the microwave reactor at 150° C. for 6 min. The reaction mixture was filtered and the filtrate was concentrated to give crude product, which was dissolved in MeOH and H$_2$O (1:1) and purified by preparative HPLC using MeOH/H$_2$O/TFA as solvent system to give (S)-2-amino-3-[4-(2-amino-6-[2,2,2-trifluoro-1-(2-(3-trifluoromethyl-pyrazol-1-yl-phenyl)-ethoxy]-pyrimidin-4-yl)-phenyl]-propionic acid as a TFA salt. LCMS: M+1=567. $^1$H-NMR (400 MHz, CD$_3$OD): δ (ppm) 3.2 (m, 1H), 3.35 (m, 1H), 4.30 (t, 1H), 6.80 (s, 1H), 6.85 (m, 1H), 6.98 (d, 1H), 7.45 (d, 2H), 7.59 (m, 1H), 7.68 (m, 2H), 7.88 (m, 1H), 7.95 (d, 2H), 8.20 (1H).

6.14. Synthesis of (S)-2-Amino-3-[4-(2-amino-6-{1-[2-(3,5-dimethyl-pyrazol-1-yl)-phenyl]-2,2,2-trifluoro-ethoxy}-pyrimidin-4-yl)-phenyl]-propionic acid

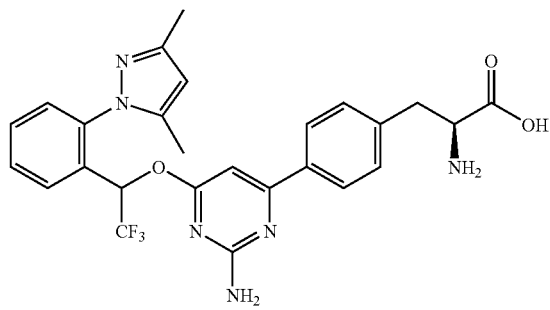

2,2,2-Trifluoro-1-(2-iodo-phenyl)-ethanol (0.331 g, 1.1 mmol), 3,5-dimethylpyrazole (0.096 g, 1.0 mmol), CuI (0.019 g, 0.1 mmol), K$_2$CO$_3$ (0.290 g, 2.1 mmol), (1R,2R)-N,N'-dimethyl-cyclohexane-1,2-diamine (0.028 g, 0.2 mmol) and toluene (10 ml) were combined in a 20 ml pressure tube and the mixture was heated at 130° C. (oil bath temperature) for 12 h. The mixture was diluted with ethyl acetate and washed with H$_2$O (2×20 ml), brine, and dried over sodium sulfate. Removal of solvent gave crude product, which was purified by ISCO column chromatography using 5-10% ethyl acetate in hexane as solvent to give 1-[2-(3,5-dimethyl-pyrazol-1-yl)-phenyl]-2,2,2-trifluoro-ethanol (120 mg).

2-Amino-4,6-dichloro pyrimidine (0.074 g, 0.45 mmol), 1-[2-(3,5-dimethyl-pyrazol-1-yl)-phenyl]-2,2,2-trifluoro-ethanol (0.120 g, 0.45 mmol), NaH (0.022 g, 0.59 mmol) were added to anhydrous THF (10 ml) under nitrogen atmosphere. The reaction was stirred at 40-45° C. for 6 h, and then cooled to room temperature, and quenched with water (0.2 ml). The reaction mixture was concentrated to give crude 4-chloro-6-{1-[2-(3,5-dimethyl-pyrazol-1-yl)-phenyl]-2,2,2-trifluoro-ethoxy]-pyrimidin-2-ylamine (0.195 g, >90% pure by LCMS) which was directly used in the following step.

The crude intermediate (0.195 g), L-p-borono-phenylalanine (0.10 g, 0.48 mmol), sodium carbonate (0.10 g, 0.95 mmol), and dichlorobis(triphenylphosphine)-palladium(II) (15 mg, 0.021 mmol) were dissolved in a mixture of MeCN (2.0 ml) and H$_2$O (2.0 ml) in a microwave vial. The vial was sealed, and reaction mixture was heated in the microwave reactor at 150° C. for 6 min. The mixture was filtered, and the filtrate was concentrated to give crude product, which was dissolved in MeOH and H$_2$O (1:1) and purified by preparative HPLC using MeOH/H$_2$O/TFA as solvent system to give (S)-2-amino-3-[4-(2-amino-6-[1-(2-(3,5-dimethyl-pyrazol-1-yl)-phenyl]-2,2,2-trifluoro-ethoxy}-pyrimidin-4-yl)-phenyl]-propionic acid as a TFA salt. LCMS: M+1=527. $^1$H-NMR (400 MHz, CD$_3$OD): δ (ppm) 4.32 (t, 1H), 3.39 (m, 1H), 3.25 (m, 1H), 2.30 (s, 3H), 2.10 (s, 3H), 7.92 (m, 3H), 7.68 (m, 2H), 7.50 (d, 2H), 7.42 (m, 1H), 6.92 (m, 1H), 6.89 (s, 1H), 6.17 (s, 1H).

6.15. Synthesis of (S)-2-Amino-3-[4-(2-amino-6-{2,2,2-trifluoro-1-[2-(3-phenyl-pyrazol-1-yl)-phenyl]-ethoxy}-pyrimidin-4-yl)-phenyl]-propionic acid

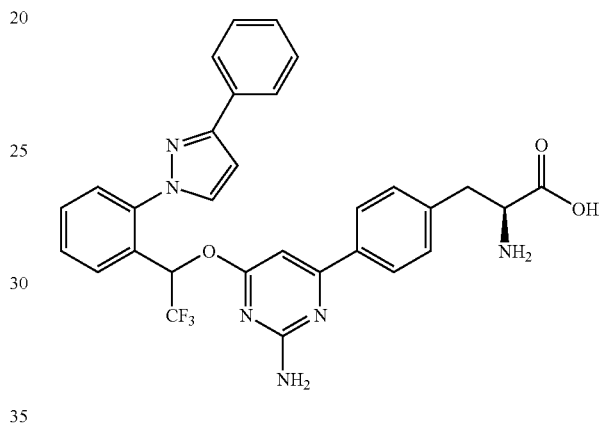

2,2,2-Trifluoro-1-(2-iodo-phenyl)-ethanol (0.331 g, 1.1 mmol), 3-phenyl pyrazole (0.144 g, 1.0 mmol), CuI (0.019 g, 0.1 mmol), K$_2$CO$_3$ (0.290 g, 2.1 mmol), (1R,2R)-N,N'-dimethyl-cyclohexane-1,2-diamine (0.028 g, 0.2 mmol) and toluene (10 ml) were taken in a 20 ml pressure tube and the mixture was heated at 130° C. (oil bath temperature) for 12 h. The mixture was diluted with ethyl acetate and washed with H$_2$O (2×20 ml), brine, and dried over sodium sulfate. Removal of solvent gave a crude product, which was purified by ISCO column chromatography using 5-10% ethyl acetate in hexane as solvent to afford 2,2,2-trifluoro-1-[2-(3-phenyl-pyrazol-1-yl)-phenyl]-ethanol (75 mg).

2-Amino-4,6-dichloro pyrimidine (0.041 g, 0.25 mmol), 2,2,2-trifluoro-1-[2-(3-phenyl-pyrazol-1-yl)-phenyl]-ethanol (0.070 g, 0.22 mmol), and NaH (0.012 g, 0.31 mmol) were added to anhydrous THF (7 ml) under nitrogen atmosphere. The reaction was stirred at 40-45° C. for 6 h, and then cooled to room temperature, and quenched with water (0.04 ml). The reaction mixture was concentrated to give crude 4-chloro-6-{2,2,2-trifluoro-1-[2-(3-phenyl-pyrazol-1-yl)-phenyl]-ethoxy}-pyrimidin-2-ylamine (0.110 g, >90% pure by LCMS), which was directly used in the following step.

The crude intermediate (0.110 g), L-p-borono-phenylalanine (0.050 g, 0.24 mmol), sodium carbonate (0.050 g, 0.48 mmol), and dichlorobis(triphenylphosphine)-palladium(II) (8 mg, 0.010 mmol) were dissolved in a mixture of MeCN (2.0 ml) and H$_2$O (2.0 ml) in a microwave vial. The vial was sealed, and reaction mixture was heated in the microwave reactor at 150° C. for 6 min. The mixture was filtered, and the filtrate was concentrated to give a crude product, which was dissolved in MeOH and H$_2$O (1:1) and purified by preparative HPLC using MeOH/H$_2$O/TFA as solvent system to give (S)-2-amino-3-[4-(2-amino-6-{2,2,2-trifluoro-1-[2-(3-phenyl-pyrazol-1-yl)-phenyl]-ethoxy}-pyrimidin-4-yl)-phenyl]-propionic acid as a TFA salt. LCMS: M+1=575. $^1$H-NMR (400 MHz, CD$_3$OD): δ (ppm) 3.20 (m, 1H), 3.38 (m, 1H), 4.30 (t, 1H), 6.80 (s, 1H), 7.00 (s, 1H), 7.30-7.48 (m, 7H), 7.62 (m, 3H), 7.90 (m, 4H), 8.10 (s, 1H).

6.16. Synthesis of (S)-2-Amino-3-[4-(2-amino-6-{2,2,2-trifluoro-1-[5-methoxy-2-(4-methyl-pyrazol-1-yl)-phenyl]-ethoxy}-pyrimidin-4-yl)-phenyl]-propionic acid

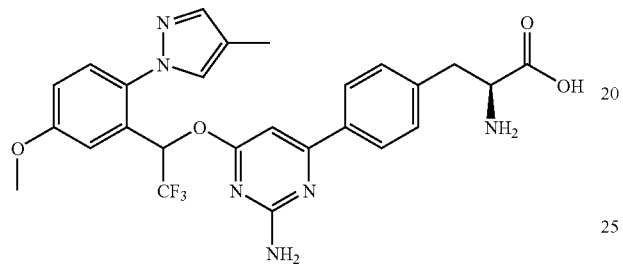

1-(2-Bromo-5-methoxy-phenyl)-2,2,2-trifluoro-ethanol (0.570 g, 2.0 mmol), 4-methyl pyrazole (0.164 g, 2.0 mmol), CuI (0.057 g, 0.3 mmol), K$_2$CO$_3$ (0.580 g, 4.2 mmol), (1R, 2R)-N,N'-dimethyl-cyclohexane-1,2-diamine (0.071 g, 0.5 mmol) and toluene (10 ml) were combined in a 20 ml pressure tube, and the mixture was heated at 130° C. (oil bath temperature) for 12 h. The mixture was diluted with ethyl acetate and washed with H$_2$O (2×20 ml), brine, and dried over sodium sulfate. Removal of solvent gave a crude product, which was purified by ISCO column chromatography using 5-10% ethyl acetate in hexane as solvent to afford 2,2,2-trifluoro-1-[5-methoxy-2-(4-methyl-pyrazol-1-yl)-phenyl]-ethanol (90 mg).

2,2,2-Trifluoro-1-[5-methoxy-2-(4-methyl-pyrazol-1-yl)-phenyl]-ethanol (0.090 g, 0.31 mmol), (S)-3-[4-(2-amino-6-chloro-pyrimidine-4-yl)-phenyl]-2-tert-butoxycarbonylamino-propionic acid (0.122 g, 0.31 mmol), 1,4-dioxane (2 ml), Cs$_2$CO$_3$ (0.503 g, 1.55 mmol) were combined in a microwave vial and heated to 180° C. for 45 min. The mixture was filtered and concentrated. To the residue, 5% methanol in DCM (50 ml) was added. The mixture was filtered. The filtrate was concentrated to give crude product which was taken in 20% TFA in DCM (30 ml) and stirred for 30 minutes at room temperature. LCMS indicated the completion of the reaction with desired product. The reaction mixture was concentrated to give crude product, which was dissolved in MeOH and H$_2$O (1:1), and purified by preparative HPLC using MeOH/H$_2$O/TFA as solvent system to give (S)-2-amino-3-[4-(2-amino-6-{2,2,2-trifluoro-1-[5-methoxy-2-(4-methyl-pyrazol-1-yl)-phenyl]-ethoxy}-pyrimidin-4-yl)-phenyl]-propionic acid.

LCMS: M+1=543. $^1$H-NMR (400 MHz, CD$_3$OD): δ (ppm) 2.20 (s, 3H), 3.22 (m, 1H), 3.40 (m, 1H), 3.84 (s, 3H), 4.35 (t, 1H), 6.84 (s, 1H), 6.98 (m, 1H), 7.18 (m, 1H), 7.26 (m, 1H), 7.40 (d, 1H), 7.48 (d, 2H), 7.66 (d, 2H), 7.96 (d, 2H).

6.17. Synthesis of (S)-2-amino-3-[4-(2-amino-6-{(R)-2,2,2-trifluoro-1-[2-(3-methyl-pyrazol-1-yl)-phenyl]-ethoxy}-pyrimidin-4-yl)-phenyl]-propionic acid

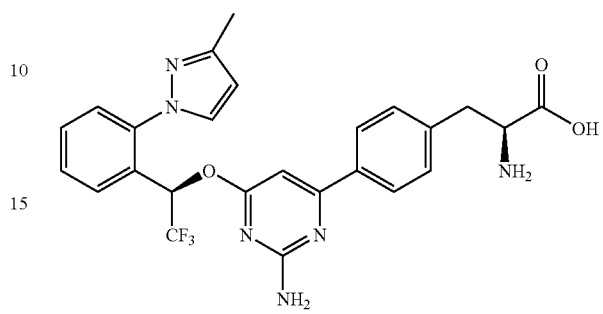

R-1-(2-bromo-phenyl)-2,2,2-trifluoro-ethanol (1.53 g, 6 mmol), 3-methylpyrazole (0.492 g, 6 mmol), CuI (0.456 g, 2.4 mmol), K$_2$CO$_3$ (2.07 g, 15 mmol), (1R,2R)-N,N'-dimethyl-cyclohexane-1,2-diamine (0.170 g, 1.2 mmol) and toluene (10 ml) were combined in a 20 ml pressure tube, and the mixture was heated at 130° C. (oil bath temperature) for 12 h. The reaction mixture was diluted with ethyl acetate and washed with H$_2$O (2×20 ml), brine, and dried over sodium sulfate. Removal of solvent gave a crude product, which was purified by ISCO column chromatography using 5-10% ethyl acetate in hexane as solvent to give R-2,2,2-trifluoro-1-[2-(3-methyl-pyrazol-1-yl)-phenyl]-ethanol (1.8 g).

2-Amino-4,6-dichloro pyrimidine (1.2 g, 7.4 mmol), R-2,2,2-trifluoro-1-[2-(3-methyl-pyrazol-1-yl)-phenyl]-ethanol (1.8 g, 7.03 mmol), and NaH (0.380 g, 10 mmol) were added to anhydrous THF (40 ml) under a nitrogen atmosphere. The reaction was stirred at 40-45° C. for 6 h, and then cooled to room temperature, and quenched with water (0.1 ml). The reaction mixture was concentrated to give afford 4-chloro-6-{R-2,2,2-trifluoro-1-[2-(3-methyl-pyrazol-1-yl)-phenyl]-ethoxy]-pyrimidin-2-ylamine (3.0 g, >90% pure by LCMS), which was directly used in the following step.

The crude intermediate (0.750 g), L-p-borono-phenylalanine (0.420 g, 2.0 mmol), sodium carbonate (0.430 g, 4.0 mmol), and dichlorobis(triphenylphosphine)-palladium(II) (30 mg, 0.043 mmol) were dissolved in a mixture of MeCN (7.0 ml) and H$_2$O (7.0 ml) in a microwave vial. The vial was sealed, and reaction mixture was heated in the microwave reactor at 150° C. for 7 min. The mixture was filtered, and the filtrate was concentrated to give a crude product, which was dissolved in MeOH and H$_2$O (1:1) and purified by preparative HPLC using MeOH/H$_2$O/TFA as solvent system to give (S)-2-amino-3-[4-(2-amino-6-{R-2,2,2-trifluoro-1-[2-(3-methyl-pyrazol-1-yl)-phenyl]-ethoxy}-pyrimidin-4-yl)-phenyl]-propionic acid as a TFA salt. LCMS: M+1=514. $^1$H-NMR (400 MHz, CD$_3$OD): δ (ppm) 2.40 (s, 3H), 3.30 (m, 1H), 3.42 (m, 1H), 4.38 (t, 1H), 6.21 (s, 1H), 7.02 (s, 1H), 7.18 (m, 1H), 7.54 (d, 1H), 7.61 (m, 4H), 7.82 (m, 2H), 7.97 (d, 2H).

6.18. Synthesis of (S)-2-amino-3-[4-(2-amino-6-{1-[4-chloro-2-(3-methyl-pyrazol-1-yl)-phenyl]-2,2,2-trifluoro-ethoxy}-pyrimidin-4-yl)-phenyl]-propionic acid

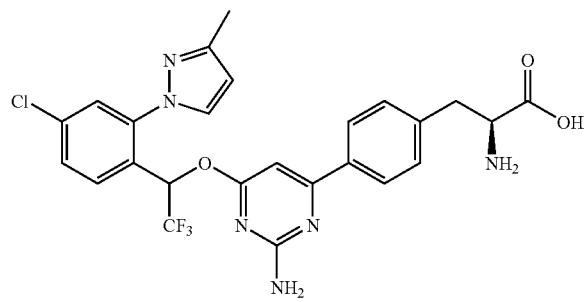

1-(4-Chloro-2-iodo-phenyl)-2,2,2-trifluoro-ethanol (0.840 g, 2.5 mmol), 3-methyl pyrazole (0.230 g, 2.8 mmol), CuI (0.190 g, 1.0 mmol), $K_2CO_3$ (0.863 g, 6.25 mmol), (1R,2R)-N,N'-dimethyl-cyclohexane-1,2-diamine (0.071 g, 0.5 mmol) and toluene (10 ml) were combined in a 20 ml pressure tube, and the mixture was heated at 130° C. (oil bath temperature) for 12 h. The mixture was diluted with ethyl acetate and washed with $H_2O$ (2×20 ml), brine, and dried over sodium sulfate. Removal of solvent gave a crude product, which was purified by ISCO column chromatography using 5-10% ethyl acetate in hexane as solvent to afford 1-[4-chloro-2-(3-methyl-pyrazol-1-yl)-phenyl]-2,2,2-trifluoro-ethanol (240 mg).

1-[4-Chloro-2-(3-methyl-pyrazol-1-yl)-phenyl]-2,2,2-trifluoro-ethanol (0.120 g, 0.41 mmol), (S)-3-[4-(2-amino-6-chloro-pyrimidine-4-yl)-phenyl]-2-tert-butoxycarbonylamino-propionic acid (0.176 g, 0.45 mmol), 1,4-dioxane (4 ml), and $Cs_2CO_3$ (0.533 g, 1.64 mmol) were combined in a 20 ml sealed tube, and the mixture was heated at 100° C. for 12 h. The mixture was concentrated. To the residue, 10% methanol in DCM (50 ml) was added and the mixture was filtered. The filtrate was concentrated to give a crude product, which was taken in THF/3N HCl (30 ml/15 ml) and the resulting mixture was stirred at 40-45° C. for 12 h. LCMS indicated the completion of reaction with desired product. The mixture was concentrated to give a crude product, which was dissolved in MeOH and $H_2O$ (1:1) and purified by preparative HPLC using MeOH/$H_2O$/TFA as solvent system to give (S)-2-amino-3-[4-(2-amino-6-{1-[4-chloro-2-(3-methyl-pyrazol-1-yl)-phenyl]-2,2,2-trifluoro-ethoxy}-pyrimidine-4-yl)-phenyl]-propionic acid as a TFA salt. LCMS: M+1=547. $^1$H-NMR (400 MHz, $CD_3OD$): δ (ppm) 2.30 (s, 3H), 3.10-3.30 (m, 2H), 4.20 (t, 1H), 6.32 (d, 1H), 6.74 (s, 1H), 7.0 (q, 1H), 7.38 (d, 2H), 7.50 (m, 2H), 7.72 (m, 1H), 7.90 (m, 3H).

6.19. Synthesis of (S)-2-Amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl]-propionic acid ethyl ester

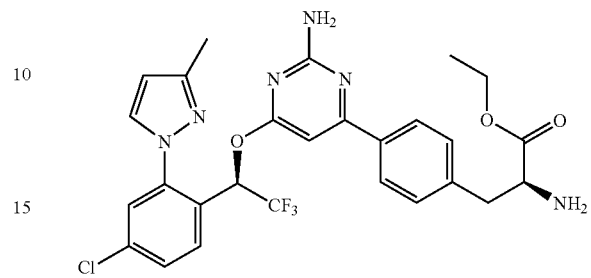

The title compound was prepared stepwise, as described below:

Step 1: Synthesis of 1-(2-bromo-4-chloro-phenyl)-2,2,2-trifluoro-ethanone. To a 500 ml 2 necked $R_B$ flask containing anhydrous methanol (300 ml) was added thionyl chloride (29.2 ml, 400 mmol) dropwise at 0-5° C. (ice water bath) over 10 min. The ice water bath was removed, and 2-bromo-4-chloro-benzoic acid (25 g, 106 mmol) was added. The mixture was heated to mild reflux for 12 h. Progress of the reaction was monitored by TLC and LCMS. After completion of the reaction, the reaction mixture was concentrated. Crude product was dissolved in dichloromethane (DCM, 250 ml), washed with water (50 ml), sat. aq. $NaHCO_3$ (50 ml), brine (50 ml), dried over sodium sulfate, and concentrated to give the 2-bromo-4-chloro-benzoic acid methyl ester (26 g, 99%), which was directly used in the following step.

2-Bromo-4-chloro-benzoic acid methyl ester (12.4 g, 50 mmol) in toluene (200 ml) was cooled to −70° C., and trifluoromethyl trimethyl silane (13 ml, 70 mmol) was added. Tetrabutylamonium fluoride (1M, 2.5 ml) was added dropwise, and the mixture was allowed to warm to room temperature over 4 h, after which it was stirred for 10 h at room temperature. The reaction mixture was concentrated to give the crude [1-(2-bromo-4-chloro-phenyl)-2,2,2-trifluoro-1-methoxy-ethoxy]-trimethyl-silane. The crude intermediate was dissolved in methanol (100 ml) and 6N HCl (100 ml) was added. The mixture was kept at 45-50° C. for 12 h. Methanol was removed, and the crude was extracted with dichloromethane (200 ml). The combined DCM layer was washed with water (50 ml), $NaHCO_3$ (50 ml), brine (50 ml), and dried over sodium sulfate. Removal of solvent gave a crude product, which was purified by ISCO column chromatography, using 1-2% ethyl acetate in hexane as solvent, to afford 1-(2-bromo-4-chloro-phenyl)-2,2,2-trifluoro-ethanone (10 g, 70%). $^1$H-NMR (300 MHz, $CDCl_3$): δ (ppm) 7.50 (d, 1H), 7.65 (d, 1H), 7.80 (s, 1H).

Step 2: Synthesis of R-1-(2-bromo-4-chloro-phenyl)-2,2,2-trifluoro-ethanol. To catechol borane (1M in THF 280 ml, 280 mmol) in a 2 L 3-necked $R_B$ flask was added S-2-methyl-CBS oxazaborolidine (7.76 g, 28 mmol) under nitrogen, and the resulting mixture was stirred at room temperature for 20 min. The reaction mixture was cooled to −78° C. (dry ice/acetone bath), and 1-(2-bromo-4-chloro-phenyl)-2,2,2-trifluoro-ethanone (40 g, 139 mmol) in THF (400 ml) was added dropwise over 2 h. The reaction mixture was allowed to warm to −36° C., and was stirred at that temperature for 24 h, and further stirred at −32° C. for another 24 h. 3N NaOH (250 ml) was added, and the cooling bath was replaced by ice-water bath. Then 30% hydrogen peroxide in water (250 ml) was added dropwise over 30 minutes. The ice water bath was removed, and the mixture was stirred at room temperature for 4 h. The organic layer was separated, concentrated and re-dissolved in ether (200 ml). The aqueous layer was extracted with ether (2×200 ml). The combined organic layers were washed with 1N aq. NaOH (4×100 ml), brine, and dried over sodium sulfate. Removal of solvent gave crude product which was purified by column chromatography using 2 to 5% ethyl acetate in hexane as solvent to give desired alcohol 36.2 g (90%, e.e. >95%). The alcohol (36.2 g) was crystallized from hexane (80 ml) to obtain R-1-(2-bromo-4-chloro-phenyl)-2,2,2-trifluoro-ethanol 28.2 g (70%; 99-100% e.e.). $^1$H-NMR (400 MHz, CDCl$_3$) δ (ppm) 5.48 (m, 1H), 7.40 (d, 1H), 7.61 (d, 2H).

Step 3: Synthesis of R-1-[4-chloro-2-(3-methyl-pyrazol-1-yl)-phenyl]-2,2,2-trifluoro-ethanol. R-1-(2-bromo-4-chloro-phenyl)-2,2,2-trifluoro-ethanol (15.65 g, 54.06 mmol), 3-methylpyrazole (5.33 g, 65 mmol), CuI (2.06 g, 10.8 mmol), K$_2$CO$_3$ (15.7 g, 113.5 mmol), (1R,2R)-N,N'-dimethyl-cyclohexane-1,2-diamine (1.54 g, 10.8 mmol) and toluene (80 ml) were combined in a 250 ml pressure tube and heated to 130° C. (oil bath temperature) for 12 h. The reaction mixture was diluted with ethyl acetate and washed with H$_2$O (4×100 ml), brine, and dried over sodium sulfate. Removal of solvent gave a crude product, which was purified by ISCO column chromatography using 5-10% ethyl acetate in hexane as solvent to get R-1-[4-chloro-2-(3-methyl-pyrazol-1-yl)-phenyl]-2,2,2-trifluoro-ethanol (13.5 g; 86%). $^1$H-NMR (400 MHz, CDCl$_3$): δ (ppm) 2.30 (s, 3H), 4.90 (m, 1H), 6.20 (s, 1H), 6.84 (d, 1H), 7.20 (s, 1H), 7.30 (d, 1H), 7.50 (d, 1H).

Step 4: Synthesis of (S)-2-Amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl]-propionic acid ethyl ester. R-1-[4-chloro-2-(3-methyl-pyrazol-1-yl)-phenyl]-2,2,2-trifluoro-ethanol (17.78 g, 61.17 mmol), (S)-3-[4-(2-amino-6-chloro-pyrimidine-4-yl)-phenyl]-2-tert-butoxycarbonylamino-propionic acid (20.03 g, 51 mmol), 1,4-dioxane (250 ml), and Cs$_2$CO$_3$ (79.5 g, 244 mmol) were combined in a 3-necked 500 ml R$_B$ flask and heated to 100° C. (oil bath temperature) for 12-24 h. The progress of reaction was monitored by LCMS. After the completion of the reaction, the mixture was cooled to 60° C., and water (250 ml) and THF (400 ml) were added. The organic layer was separated and washed with brine (150 ml). The solvent was removed to give crude BOC protected product, which was taken in THF (400 ml), 3N HCl (200 ml). The mixture was heated at 35-40° C. for 12 h. THF was removed in vacuo. The remaining aqueous layer was extracted with isopropyl acetate (2×100 ml) and concentrated separately to recover the unreacted alcohol (3.5 g). Traces of remaining organic solvent were removed from the aqueous fraction under vacuum.

To a 1 L beaker equipped with a temperature controller and pH meter, was added H$_3$PO$_4$ (40 ml, 85% in water) and water (300 ml) then 50% NaOH in water to adjust pH to 6.15. The temperature was raised to 58° C. and the above acidic aqueous solution was added dropwise into the buffer with simultaneous addition of 50% NaOH solution in water so that the pH was maintained between 6.1 to 6.3. Upon completion of addition, precipitated solid was filtered and washed with hot water (50-60° C.) (2×200 ml) and dried to give crude (S)-2-amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl}-propionic acid (26.8 g; 95%). LCMS and HPLC analysis indicated the compound purity was about 96-97%.

To anhydrous ethanol (400 ml) was added SOCl$_2$ (22 ml, 306 mmol) dropwise at 0-5° C. Crude acid (26.8 g) from the above reaction was added. The ice water bath was removed, and the reaction mixture was heated at 40-45° C. for 6-12 h. After the reaction was completed, ethanol was removed in vacuo. To the residue was added ice water (300 ml), and extracted with isopropyl acetate (2×100 ml). The aqueous solution was neutralized with saturated Na$_2$CO$_3$ to adjust the pH to 6.5. The solution was extracted with ethyl acetate (2×300 ml). The combined ethyl acetate layer was washed with brine and concentrated to give 24 g of crude ester (HPLC purity of 96-97%). The crude ester was then purified by ISCO column chromatography using 5% ethanol in DCM as solvent to give (S)-2-amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl}-propionic acid ethyl ester (20.5 g; 70%; HPLC purity of 98%). LCMS M+1=575. $^1$H-NMR (400 MHz, CD$_3$OD): δ (ppm) 1.10 (t, 3H), 2.25 (s, 3H), 2.85 (m, 2H), 3.65 (m, 1H), 4.00 (q, 2H), 6.35 (s, 1H), 6.60 (s, 1H), 6.90 (m, 1H), 7.18 (d, 2H), 7.45 (m, 2H), 7.70 (d, 1H), 7.85 (m, 3H).

6.20. Synthesis of (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl) propanoic acid

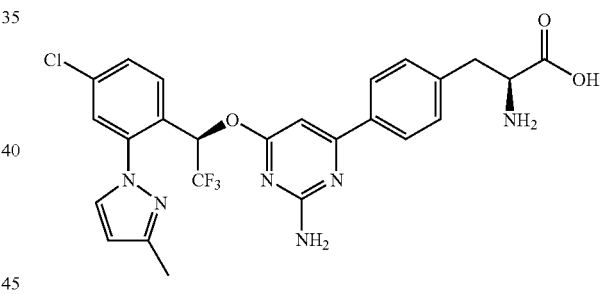

(S)-2-Amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl}-propionic acid ethyl ester (22.2 g, 38.6 mmol) was dissolved in THF (220 ml) and water (50 ml). Lithium hydroxide monohydrate (5.56 g, 132 mmol) was added. The reaction mixture was stirred at room temperature for 12 h. THF was removed, and water (100 ml) was added to the residue to get the clear solution.

To a 1 L beaker equipped with a temperature controller and pH meter was added H$_3$PO$_4$ (40 ml, 85% in water), water (300 ml) and 50% NaOH in water to adjust the pH to 6.15. The temperature was raised to 58° C., and the aqueous Li-salt of the compound was added dropwise into the buffer with simultaneous addition of 3N HCl so that the pH was maintained at 6.1 to 6.2. Upon completion of addition, precipitated solid was filtered and washed with hot water (50-60° C.) (2×200 ml) and dried to give (S)-2-amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl}-propionic acid (19.39 g; 92%). LCMS and the HPLC analysis indicated the compound purity was about 98-99%. LCMS M+1=547. $^1$H-NMR (400

MHz, CD$_3$OD): δ (ppm) 2.40 (s, 3H), 3.22-3.42 (m, 2H), 4.38 (t, 1H), 6.42 (s, 1H), 7.10 (s, 1H), 7.21 (m, 1H), 7.60 (m, 4H), 7.81 (d, 1H), 7.92 (m, 3H).

6.21. Synthesis of (S)-2-Amino-3-(4-{2-amino-6-[2,2,2-trifluoro-1-(2-thiazol-2-yl-phenyl)-ethoxy]-pyrimidin-4-yl}-phenyl)-propionic acid

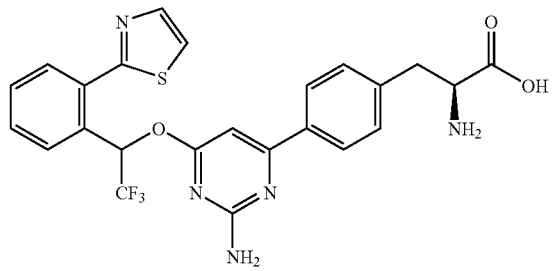

To a 40 ml microwave reactor, was added 1.04 g of 2-formyl phenylboronic acid (6.9 mmoles), 1.14 g of 2-bromo thiazole (6.9 mmoles), 240 mg of palladium bis-triphenyl-phosphine dichloride (Pd(PPh$_3$)$_2$Cl$_2$, 0.34 mmoles). Then, 13.8 ml of 1M Na$_2$CO$_3$ (13.8 mmoles) and 10 ml of CH$_3$CN were added to the mixture. The reactor was sealed, and the reaction was run under microwave at 160° C. for 5 minutes. LCMS shows completion of the reaction with desired product. The reaction mixture was then poured into a separation funnel. Then 200 ml of methylene chloride and 100 ml of water were added for extraction. The methylene chloride layer was dried over MgSO$_4$. Removal of solvent gave a crude product, which was purified by silica gel column chromatography eluting with hexanes/ethyl acetate mixture (5/1 to 2/1) to give pure 2-thiazol-2-yl-benzaldehyde (0.5 g, yield: 38%).

To a 50 ml round bottom flask, 184 mg of 2-thiazol-2-yl-benzaldehyde (0.97 mmole) and 10 ml of anhydrous tetrahydrofuran (THF) were added. Then, 145.4 mg of trifluoromethyltrimethylsilane (1.02 mmoles) and 20 μl of 1M tert-butylammonium fluoride in THF (0.02 mmole) were added to solution. The mixture was stirred at room temperature overnight, after which 10 ml of 1 N HCl was added and the reaction mixture was stirred at r.t. for 15 minutes. THF was removed in vacuo, and the mixture was extracted with methylene chloride (3×50 ml). The combined CH$_2$Cl$_2$ layer was dried over MgSO$_4$. Removal of solvent gave 262 mg of crude product, which was about 95% pure, and was used in next step without further purification.

2,2,2-Trifluoro-1-(2-thiazol-2-yl-phenyl)-ethanol (260 mg, 1 mmole), (S)-3-[4-(2-amino-6-chloro-pyrimidin-4-yl)-phenyl]-2-tert-butoxycarbonylamino-propionic acid (390 mg, 1 mmole), cesium carbonate (1.3 g, 4 mmoles) and 10 ml of 1,4-dioxane were mixed together in a 50 ml sealed tube. The reaction mixture was heated at 100° C. for 3 days. Water (20 ml) was added, and then 1N HCl aq. was added slowly to adjust the pH to 4, then the 1,4-dioxane was removed in vacuo and the resulting mixture was extracted with methylene chloride (3×50 ml). The combine methylene chloride layer was dried over MgSO$_4$. Removal of solvent gave a crude product, which was taken to next step reaction without further purification.

The above crude product was dissolved in 5 ml of methylene chloride, and 0.4 ml of trifluoroacetic acid was added. The mixture was stirred at room temperature overnight. The trifluoroacetic acid was then removed in vacuo to give a crude product, which was purified by prep HPLC to give 63 mg of pure product. HPLC; YMC Pack ODS-A 3×50 mm, 7 um; Solvent A=water with 0.1% TFA; Solvent B=methanol with 0.1% TFA. Solvent B from 10 to 90% over 4 minutes; Flow rate=2 ml/min; RT=3 min. HPLC purity=100%. LCMS: M+1=515.9. $^1$H NMR (400 MHz, CD$_3$OD) δ 8.06 ppm (2H, m); 7.92 (2H, d, J=8 Hz); 7.84 (1H, m); 7.81 (1H, m); 7.77 (1H, d, J=4 Hz); 7.57 (2H, m); 7.45 (2H, d, J=8 Hz); 6.84 (1H, s); 4.30 (2H, dd, J=8 Hz); 3.38 (2H, dd, J=12, 2 Hz); 3.23 (2H, dd, J=12, 8 Hz).

6.22. Synthesis of (S)-2-Amino-3-[4-(2-amino-6-{2,2,2-trifluoro-1-[2-(Pyridin-3-yloxy)-phenyl]-ethoxy}-pyrimidin-4-yl)-phenyl]-propionic acid; (S)-2-Amino-3-[4-(2-amino-6-{2,2,2-trifluoro-1-[4-(Pyridin-3-yloxy)-phenyl]-ethoxy}-pyrimidin-4-yl)-phenyl]-propionic acid; (S)-2-Amino-3-[4-(6-{2,2,2-trifluoro-1-[4-(Pyridin-3-yloxy)-phenyl]-ethoxy}-pyrimidin-4-yl)-phenyl]-propionic acid; (S)-2-Amino-3-(4-{2-amino-6-[2,2,2-trifluoro-1-(4-thiophen-2-yl-phenyl)-ethoxy]-pyrimidin-4-yl}-phenyl)-propionic acid; (S)-2-Amino-3-(4-{6-[2,2,2-trifluoro-1-(4-imidazol-1-yl-phenyl)-ethoxy]-pyrimidin-4-yl}-phenyl)-propionic acid; and (S)-2-Amino-3-(4-{2-amino-6-[2,2,2-trifluoro-1-(4-[1,2,4]triazol-1-yl-phenyl)-ethoxy]-pyrimidin-4-yl}-phenyl)-propionic acid

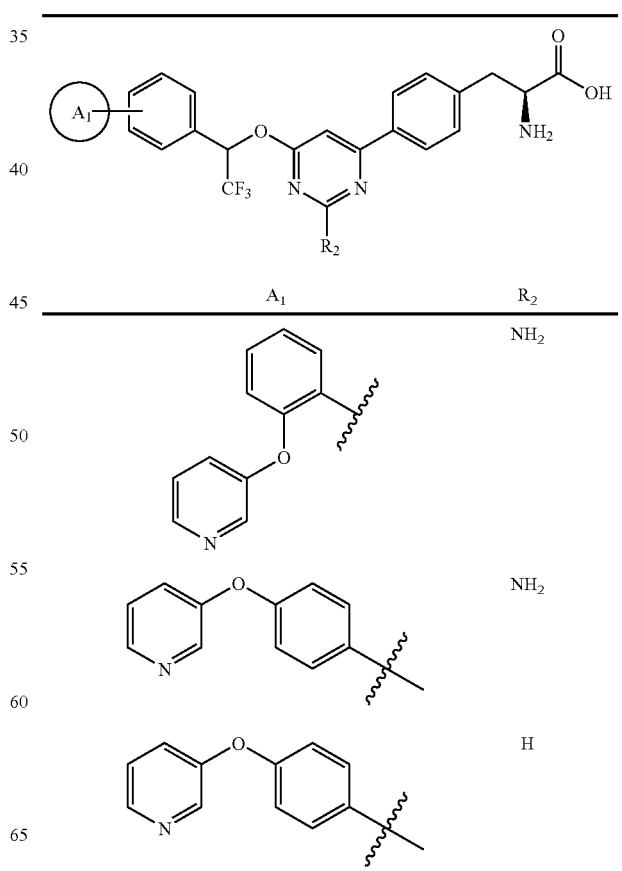

-continued

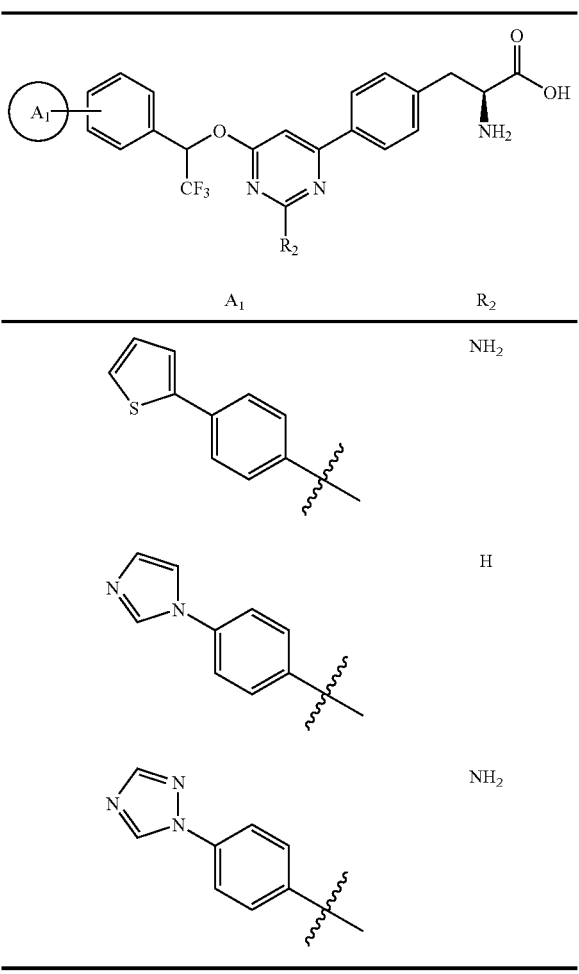

| A₁ | R₂ |
|---|---|
| (thiophene-phenyl) | NH₂ |
| (imidazole-phenyl) | H |
| (triazole-phenyl) | NH₂ |

The title compounds were prepared using the general approach shown below:

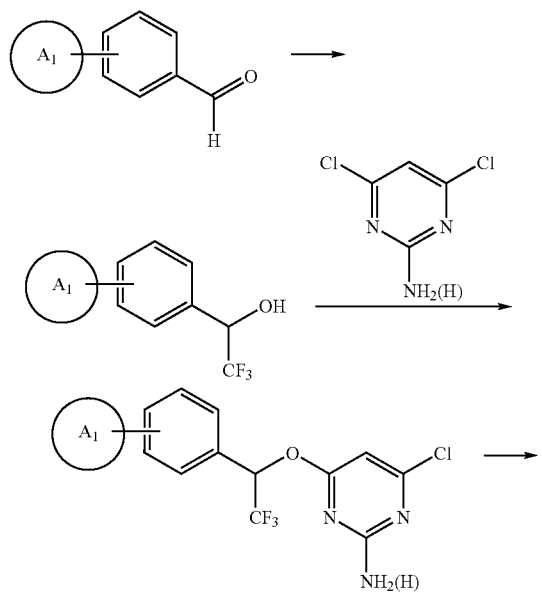

In this approach, tetra-n-butyl ammonium fluoride (0.05 eq.) was added to a mixture of substituted benzaldehyde (1 eq.) and trifluoromethyl trimethylsilane (1.2 eq.) in THF at 0° C. The temperature was then allowed to warm to room temperature. The mixture was stirred at room temperature for 5 h, then diluted with ethyl acetate, washed with water, brine and dried by $MgSO_4$. The solvent was removed under reduced pressure to give the trifluoro-alcohol as crude product, which was used in next step without further purification.

The above-made alcohol (1 eq.) was dissolved in anhydrous 1,4-dioxane. Sodium hydride (60% in mineral oil, 1.2 eq.) was added all at once, and the mixture was stirred at room temperature for 30 minutes. 2-Amino-4,6-dichloropyrimidine (1 eq.) was added, and the resulting mixture was stirred at 80° C. for 2 h. The solvent was removed, and the residue was suspended in ethyl acetate, which was washed with water, dried over $MgSO_4$ and then concentrated to give the desired monochloride product, which was used in next step without further purification.

The above crude product (1 eq.) was added to a 5 ml microwave vial containing 4-borono-L-phenylalanine (1 eq.), $Na_2CO_3$ (2 eq.), acetonitrile (2 ml), water (2 ml) and dichlorobis(triphenylphosphine)-palladium (0.05 eq.). The vial was capped, and the mixture was heated at 150° C. for 5 min under microwave radiation. The mixture was cooled, filtered through a syringe filter, and then separated by a reverse phase preparative-HPLC using YMC-Pack ODS 100×30 mm ID column (MeOH/$H_2$O/TFA solvent system). The pure fractions were combined and concentrated in vacuum. The product was then suspended in 5 ml of water, frozen and lyophilized to give the product as a trifluoro acetic acid (TFA) salt.

(S)-2-Amino-3-[4-(2-amino-6-{2,2,2-trifluoro-1-[2-(pyridin-3-yloxy)-phenyl]-ethoxy}-pyrimidin-4-yl)-phenyl}-propionic acid. $^1$H-NMR (400 MHz, $CD_3OD$) δ: 3.05-3.40 (m, 2H), 3.81 (m, 1H), 6.64 (s, 1H), 7.01 (d, 1H), 7.15-7.54 (m, 7H), 7.74 (d, 1H), 7.94 (d, 2H), 8.35 (m, 2H).

(S)-2-Amino-3-[4-(2-amino-6-{2,2,2-trifluoro-1-[4-(pyridin-3-yloxy)-phenyl]-ethoxy}-pyrimidin-4-yl)-phenyl}-propionic acid. $^1$H-NMR (400 MHz, $CD_3OD$) δ: 3.20-3.41 (m, 2H), 4.30 (m, 1H), 6.81 (m, 2H), 7.17 (m, 2H), 7.46-7.69 (m, 6H), 7.93 (d, 2H), 8.41 (s, 2H).

(S)-2-Amino-3-[4-(6-{2,2,2-trifluoro-1-[4-(pyridin-3-yloxy)-phenyl]-ethoxy}-pyrimidin-4-yl)-phenyl}-propionic acid. $^1$H-NMR (300 MHz, $CD_3OD$) δ: 3.15-3.35 (m, 2H), 4.25 (t, 1H), 6.90 (q, 1H), 7.25 (d, 2H), 7.45 (d, 2H), 7.71 (m, 3H), 7.99 (m, 3H), 8.14-8.18 (m, 1H), 8.55 (d, 1H), 8.63 (d, 1H), 8.84 (d, 1H).

(S)-2-Amino-3-[4-(2-amino-6-{2,2,2-trifluoro-1-(4-thiophen-2-yl-phenyl)-ethoxy}-pyrimidin-4-yl)-phenyl}-propionic acid. $^1$H-NMR (400 MHz, $CD_3OD$) δ: 3.03-3.31 (m, 2H), 4.19 (m, 1H), 6.68 (m, 2H), 7.00 (m, 1H), 7.31-7.36 (m, 4H), 7.52 (m, 2H), 7.62 (d, 2H), 7.85 (d, 2H).

(S)-2-Amino-3-(4-{6-[2,2,2-trifluoro-1-(4-imidazol-1-yl-phenyl)-ethoxy]-pyrimidin-4-yl}-phenyl)-propionic acid. ¹H-NMR (400 MHz, CD₃OD) δ: 3.03-3.31 (m, 2H), 4.19 (m, 1H), 6.88 (m, 1H), 7.32-8.63 (m, 11H), 8.64 (s, 1H), 9.25 (s, 1H).

(S)-2-Amino-3-(4-{2-amino-6-[2,2,2-trifluoro-1-(4-[1,2,4]triazol-1-yl-phenyl)-ethoxy]-pyrimidin-4-yl}-phenyl)-propionic acid. ¹H-NMR (400 MHz, CD₃OD) δ: 3.07-3.36 (m, 2H), 4.16 (m, 1H), 6.65 (s, 1H), 6.75 (m, 1H), 7.31 (d, 2H), 7.69 (d, 2H), 7.85 (m, 4H), 8.08 (s, 1H), 9.03 (s, 1H).

6.23. Synthesis of (S)-2-Amino-3-(4-{2-amino-6-[2,2,2-trifluoro-1-(4-fluoro-2-thiophen-3-yl-phenyl)ethoxy]-pyrimidin-4-yl}-phenyl)-propionic acid; (S)-2-Amino-3-[4-(2-amino-6-{2,2,2-trifluoro-1-[4-fluoro-2-(4-methyl-thiophen-2-yl)-phenyl]-ethoxy}-pyrimidin-4-yl)-phenyl]-propionic acid; and (S)-2-Amino-3-[4-(2-amino-6-{1-[2-(3,5-dimethyl-isoxazol-4-yl]-4-fluoro-phenyl]-2,2,2-trifluoro-ethoxy}-pyrimidin-4-yl)-phenyl]-propionic acid

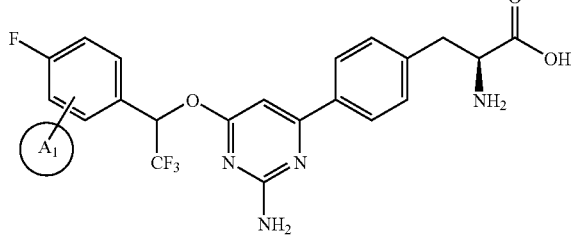

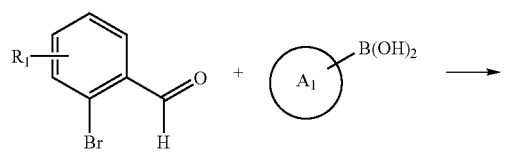

The title compounds were prepared using the general approach shown below:

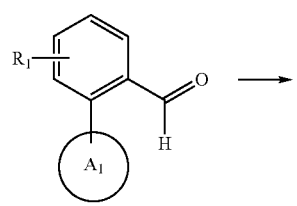

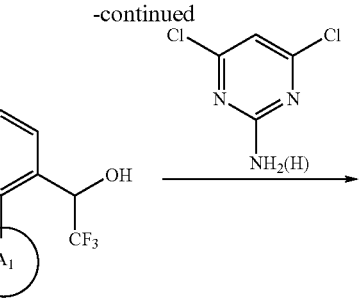

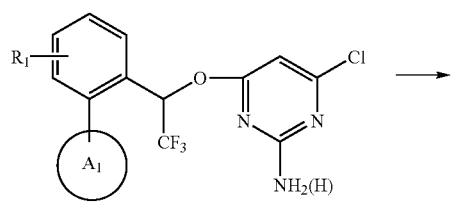

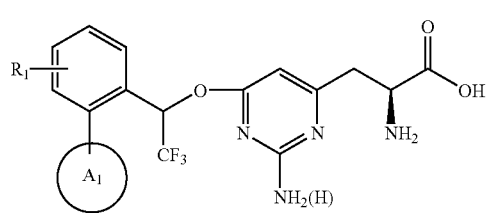

In this approach, the bromo substituted benzyl aldehyde (1 eq) was added to a 20 ml microwave vial, which contained aromatic heterocyclic boronic acid (1 eq), Na₂CO₃ (2 eq), acetonitrile (8 ml)/water (8 ml) and dichlorobis(triphenylphosphine)-palladium (0.05 eq). The vial was capped and stirred at 150° C. for 6 min under microwave radiation. The reaction mixture was cooled, filtered through a syringe filter and then diluted with ethyl acetate. It was washed with water. Silica gel was then added to make a plug, and it was purified by chromatography eluted with hexane and ethyl acetate.

Above made aldehydes then underwent the same reactions described above in Example 22.

(S)-2-Amino-3-(4-{2-amino-6-[2,2,2-trifluoro-1-(4-fluoro-2-thiophen-3-yl-phenyl)-ethoxy]-pyrimidin-4-yl}-phenyl)-propionic acid. ¹H-NMR (400 MHz, CD₃OD) δ: 3.08-3.30 (m, 2H), 4.19 (m, 1H), 6.61 (s, 1H), 6.84 (m, 1H), 7.02-7013 (m, 2H), 7.22 (dd, 1H), 7.32 (d, 2H), 7.47 (m, 1H), 7.77 (m, 1H), 7.84 (d, 2H).

(S)-2-Amino-3-(4-{2-amino-6-{2,2,2-trifluoro-1-(4-fluoro-2-(4-methyl-thiophen-2-yl)-phenyl]-ethoxy}-pyrimidin-4-yl}-phenyl)-propionic acid. ¹H-NMR (400 MHz, CD₃OD) δ: 2.26 (s, 3H), 3.09-3.30 (m, 2H), 4.20 (m, 1H), 6.64 (s, 1H), 6.95 (m, 2H), 7.13 (m, 3H), 7.34 (d, 2H), 7.69 (m, 1H), 7.83 (d, 2H).

(S)-2-amino-3-[4-(2-amino-6-{1-[2-(3,5-dimethyl-isoxazol-4-yl]-4-fluoro-phenyl]-2,2,2-trifluoro-ethoxy}-pyrimidin-4-yl)-phenyl]-propionic acid. ¹H-NMR (400 MHz, CD₃OD) δ: 1.89-2.19 (m, 6H), 2.97-3.30 (m, 2H), 3.83 (m, 1H), 6.55 (d, 1H), 6.74-6.87 (m, 1H), 7.00 (m, 1H), 7.7.24-7.33 (m, 3H), 7.88 (m, 3H).

6.24. Synthesis of (S)-2-amino-3-[4-(2-amino-6-{2,2,2-trifluoro-1-[5-fluoro-2-(3-methyl-pyrazol-1-yl)-phenyl]-ethoxy}-pyrimidin-4-yl)-phenyl]-propionic acid

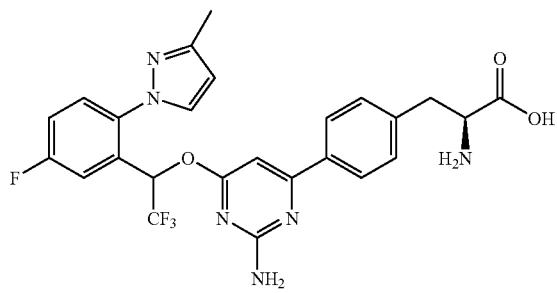

The mixture of 2-bromo-5-fluoro-benzoic acid methyl ester (1 g, 4.292 mmol), NaBH₄ (0.423 g, 11.159 mmol) and LiCl (0.474 g, 11.159 mmol) in THF/EtOH (20 ml/10 ml) was stirred at room temperature overnight. Aqueous HCl (10 ml, 2N) was added and stirred for about 10 min. Then the organic solvent was removed under low vacuum. The residue was diluted with water and extracted by ethyl acetate. The organic layer was washed with aqueous NaHCO₃ (10%), water and brine, and then dried (MgSO₄) and concentrated to afford 852 mg (96.8% crude yield) crude product, (2-bromo-5-fluoro-phenyl)methanol, as a white solid, which was used without further purification.

To the solution of (2-bromo-5-fluoro-phenyl)methanol (0.852 g, 4.156 mmol) in DCM (15 ml) was added MnO₂ (4.254 g, 85%, 41.56 mmol). The mixture was stirred at room temperature for two days, and then filtered and washed with DCM. The filtrate was concentrated to afford 777 mg 2-bromo-5-fluoro-benzaldehyde (92% yield). The newly made aldehyde (0.777 g, 3.828 mmol) was then dissolved in anhydrous THF (10 ml) and cooled to 0° C. Trifluoromethyl trimethylsilane (1.13 ml, 7.656 mmol) was added, and followed by tetrabutyl ammonium fluoride (0.020 g, 0.076 mmol). The temperature was then allowed to warm to room temperature. The mixture was stirred for 5 h at room temperature, then diluted with ethyl acetate, washed with water, brine and dried by MgSO₄. The solvent was removed under reduced pressure to give 2-bromo-5-fluoro-phenyl)2,2,2-trifluoro-ethanol, 1.1 g (90% purity) as a crude product, which was used for the next step without further purification.

2-Bromo-5-fluoro-phenyl)2,2,2-trifluoro-ethanol (0.990 g, 3.263 mmol, 90%), 3-methylpyrazole (0.476 g, 4.895 mmol), CuI (0.367 g, 1.632 mmol), K₂CO₃ (1.334 g, 8.158 mmol), (1R,2R)-N,N'-dimethyl-cyclohexane-1,2-diamine (0.110 g, 0.653 mmol) and toluene (10 ml) were combined in a 20 ml microwave vial, which was then sealed and heated at 180° C. for 40 min. The mixture was filtered and washed with ethyl acetate. The filtrate was washed with water for 3 times and then silica gel was added to make a plug. The compound was purified by ISCO column chromatography using 5-10% ethyl acetate in hexane as solvent to get 1-(5-fluoro-2-(3-methyl-pyrazol-1-yl)-phenyl]-2,2,2-trifluoro-ethanol 75 mg. ¹H-NMR (400 MHz, CDCl₃) δ: 2.29 (s, 3H), 4.90 (m, 1H), 6.21 (d, 1H), 7.07-7.11 (m, 1H), 7.19-7.22 (m, 1H), 7.29-7.32 (m, 1H), 7.51 (d, 1H).

The above-made alcohol (0.075 g, 0.273 mmol) was dissolved in anhydrous 1,4-dioxane (3 ml). Sodium hydride (0.013 g, 0.328 mmol, 60% in mineral oil) was added all at once, and the mixture was stirred at room temperature for 30 minutes. 2-Amino-4,6-dichloro-pyrimidine (0.045 g, 0.273 mmol) was added. The mixture was stirred at 80° C. for about 2 hours. The solvent was removed, and the residue was suspended in ethyl acetate, which was washed with water, dried over MgSO₄ and then concentrated to give the desired monochloride product 100 mg (0.249 mmol), which was added to a 5 ml microwave vial containing 4-borono-L-phenylalanine (0.052 g, 0.249 mmol), Na₂CO₃ (0.053 g, 0.498 mmol), acetonitrile (2 ml)/water (2 ml) and dichlorobis(triphenylphosphine)-palladium (5 mg, 0.007 mmol). The vial was capped and stirred at 150° C. for 5 min under microwave radiation. The reaction mixture was cooled, filtered through a syringe filter, and then separated by reverse phase preparative-HPLC using YMC-Pack ODS 100×30 mm ID column (MeOH/H₂O/TFA solvent system). The pure fractions were concentrated in vacuum. The product was then suspended in 5 ml of water, frozen and lyophilized to give (S)-2-amino-3-[4-(2-amino-6-{(R)-1-[5-fluoro-2-(3-methyl-pyrazol-1-yl)-phenyl]-2,2,2-trifluoro-ethoxy}-pyrimidin-4-yl)-phenyl]-propionic acid, 37 mg as a trifluoro salt. ¹H-NMR (400 MHz, CD₃OD): δ 2.29 (s, 3H), 3.08-3.30 (m, 2H), 4.19 (q, 1H), 6.32 (d, 1H), 6.82 (s, 1H), 6.85 (m, 1H), 7.26 (m, 1H), 7.33 (d, 2H), 7.42 (m, 2H), 7.75 (d, 1H), 7.87 (d, 2H).

6.25. Synthesis of (S)-2-amino-3-[4-(2-amino-6{2,2,2-trifluoro-1-[5-chloro-2-(3-methyl-pyrazol-1-yl)-phenyl]-ethoxy}-pyrimidin-4-yl)-phenyl]-propionic acid

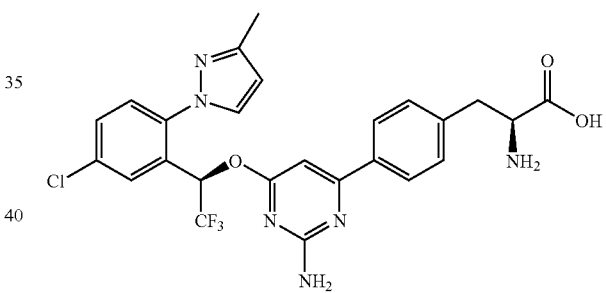

The title compounds was prepared from R-1-[5-chloro-2-(3-methyl-pyrazol-1-yl)-phenyl]-2,2,2-trifluoro-ethanol, which was prepared using the same approach as described above for R-1-[4-chloro-2-(3-methyl-pyrazol-1-yl)-phenyl]-2,2,2-trifluoro-ethanol. In particular, R-1-[5-chloro-2-(3-methyl-pyrazol-1-yl)-phenyl]-2,2,2-trifluoro-ethanol (0.959 g, 3.318 mmol) was dissolved in anhydrous 1,4-dioxane (8 ml). Sodium hydride (0.159 g, 3.982 mmol, 60% in mineral oil) was added all at once, and the mixture was stirred at room temperature for 30 minutes. 2-Amino-4,6-dichloro-pyrimidine (0.544 g, 3.318 mmol) was added. The mixture was stirred at 80° C. for about 2 hours. The solvent was removed, and the residue was suspended in ethyl acetate, which was washed with water, dried over MgSO₄ and then concentrated to give the desired monochloride product 1.38 g, which was used directly without further purification.

The monochloride (0.460 g, 1.104 mmol) made above was added to a 20 ml microwave vial, which contained 4-borono-L-phenylalanine (0.277 g, 1.325 mmol), Na₂CO₃ (0.234 g, 2.208 mmol), acetonitrile (8 ml)/water (8 ml) and dichlorobis (triphenylphosphine)-palladium (0.039 g, 0.055 mmol). The vial was capped and the mixture stirred at 150° C. for 10 minutes under microwave radiation. The mixture was cooled, filtered through a syringe filter and then separated by a reverse phase preparative-HPLC using YMC-Pack ODS 100×30 mm ID column (MeOH/H₂O/TFA solvent system). The pure fractions were concentrated in vacuum. The product was then suspended in 5 ml of water, frozen and lyophilized to give 580 mg of (S)-2-amino-3-[4-(2-amino-6-{R-1-[5-chloro-2-(3-methyl-pyrazol-1-yl)-phenyl]-2,2,2-trifluoro-ethoxy}-pyrimidin-4-yl)-phenyl}-propionic acid. ¹H-NMR (400 MHz, CD₃OD): δ 2.40 (s, 3H), 3.29-3.46 (m, 2H), 4.38 (q, 1H), 6.45 (d, 1H), 7.09 (s, 1H), 7.24 (m, 1H), 7.53-7.70 (m, 4H), 7.82 (s, 1H), 7.90 (d, 1H), 7.97 (d, 2H).

6.26. Synthesis of (S)-2-amino-3-[4-(2-amino-6-{2,2,2-trifluoro-1-[4-(2-oxo-pyrrolidin-1-yl)-phenyl]-ethoxy}-pyrimidin-4-yl)-phenyl]-propionic acid

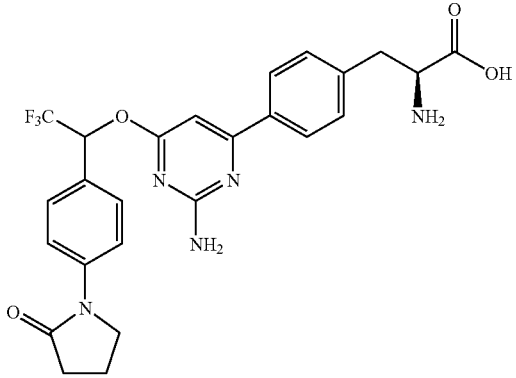

4-(2-Oxo-pyrrolidine-1-yl)-benzaldehyde (500 mg, 2.64 mmol) in THF (20 ml) was cooled to 0° C. and trifluoromethyl trimethyl silane (375 mg, 2.64 mmol) was added. Tetrabutylammonium fluoride (1M, 0.1 ml) was added dropwise, and the mixture was allowed to warm to room temperature over 1 h and stirred further for over-night at room temperature. After completion of the reaction, 3N HCl (5 ml) was added, and the reaction mixture was stirred for 2 hr. The mixture was concentrated. Water (20 ml) was added and the mixture was extracted by EtOAc (2×20 ml) and washed with NaHCO₃ (20 ml), brine (20 ml), and dried over sodium sulfate and concentrated to give 590 mg of desired product, which was used in next step without further purification (yield of 86%).

A solution of 4,6-dichloro-pyrimidin-2-ylamine (700 mg, 2.69 mmol), NaH (194 mg, 8.07 mmol, 60%) and 1-(4-(2,2,2-trifluoro-1-hydroxy-ethyl)-phenyl)-pyrrolidine-2-one (441 mg, 2.69 mmol) in dry THF (10 ml) was stirred at room temperature for overnight. After completion of the reaction, THF was removed under reduced pressure. Water (10 ml) was added while the mixture was cooled down to 0° C. The mixture was then extracted with dichloromethane (2×40 ml). The combined organic solution was dried over Na₂SO₄. Removal of solvent gave 498 mg of desired product with 92% purity, which was used in next step without further purification (yield of 498 mg, 48%).

An Emrys process vial (20 ml) for microwave was charged with 1-(4-(2-amino-6-chloro-pyrimidin-4-yloxy)-2,2,2-trifluoro-ethyl)-phenyl)-pyrrolidine-2-one (200 mg, 0.51 mmol), 4-borono-L-phenylalanine (108 mg, 0.51 mmol) and 5 ml of acetonitrile. 5 ml of aqueous sodium carbonate (1M) was added to above solution followed by 5 mol % of dichlorobis(triphenylphosphine)-palladium (II). The reaction vessel was sealed and heated to 160° C. for 7 min with microwave irradiation. After cooling, the reaction mixture was evaporated to dryness. The residue was dissolved in 4 ml of methanol and purified with Prep-LC to give 153 mg of product (yield 58%). ¹H-NMR (400 MHz, CD₃OD): δ (ppm) 2.1 (m, 2H), 2.5 (t, 2H), 3.05-3.4 (m, 2H), 3.85 (t, 2H), 4.2 (m, 1H), 6.6 (m, 1H), 6.75 (s, 1H), 7.3 (d, 2H), 7.5 (d, 2H), 7.6 (d, 2H), 7.9 (d, 2H).

6.27. Synthesis of (S)-2-Amino-3-[4-(2-amino-6-{(R)-2,2,2-trifluoro-1-[5-fluoro-2-(3-methyl-pyrazol-1-yl)-phenyl]-ethoxy}-pyrimidin-4-yl)-phenyl]-propionic acid

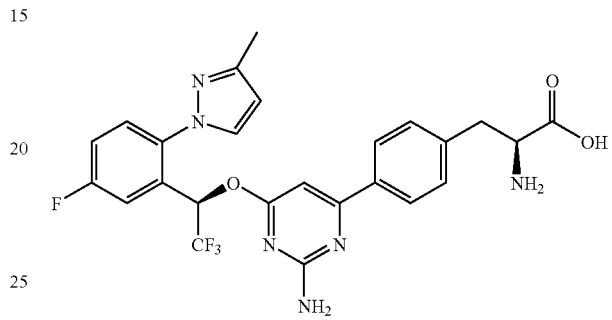

R-1-(2-Bromo-5-fluoro-phenyl)-2,2,2-trifluoro-ethanol (4.0 g, 14.65 mmol), 3-methyl pyrazole (1.56 g, 19.04 mmol), CuI (0.557 g, 2.93 mmol), K₂CO₃ (4.25 g, 30.76 mmol), (1R,2R)-N,N'-dimethyl-cyclohexane-1,2-diamine (0.416 g, 2.93 mmol) and toluene (15 ml) were taken in 50 ml of sealed tube and the resulting mixture was heated at 130° C. (oil bath temperature) for 2 days. Mixture was diluted with ethyl acetate and washed with H₂O (4×30 ml), brine, and dried over sodium sulfate. Removal of solvent gave a crude product, which was purified by ISCO column chromatography using 5-10% ethyl acetate in hexane as solvent to give 1.75 g of R-2,2,2-trifluoro-1-[5-fluoro-2-(3-methyl-pyrazol-1-yl)-phenyl]-ethanol (Yield: 44%). ¹H-NMR (400 MHz, CDCl₃): δ (ppm) 2.35 (s, 3H), 5.0 (m, 1H), 6.3 (s, 1H), 7.1 (m, 1H), 7.20 (s, 1H), 7.35 (d, 1H), 7.50 (s, 1H).

A solution of 4,6-dichloro-pyrimidin-2-ylamine (938 mg, 5.72 mmol), NaH (188 mg, 1.5 eq. 8.17 mmol, 60%) and R-2,2,2-trifluoro-1-[5-fluoro-2-(3-methyl-pyrazol-1-yl)-phenyl]-ethanol (1.5 g, 1 eq. 5.45 mmol) in dry THF (10 ml) was stirred at room temperature at 50° C. overnight. After completion of the reaction, THF was removed under reduced pressure. Water (10 ml) was added to quench the reaction. The mixture was then extracted with dichloromethane (2×40 ml). The combined organic solution was dried over Na₂SO₄. Removal of solvent gave desired product with 92% purity, which was used in next step without purification (yield: 85%).

An Emrys process vial (20 ml) for microwave was charged with chloro-6-R-2,2,2-trifluoro-1-(5-fluoro-2-(3-methyl-pyrazol-1-yl)-phenyl)-ethoxy)-pyrimidin-2-ylamine (2.18 g, 5.45 mmol), 4-borono-L-phenylalanine (1.13 g, 5.45 mmol), sodium carbonate (1 M 10.90 ml, 2 eq.) was added to above solution followed by 5 mol % of dichlorobis (triphenylphosphine)-palladium(II) (191 mg, 0.27 mmol) and 5 ml of acetonitrile, and 5 ml H₂O. The reaction vessel was sealed, and the mixture was heated at 160° C. for 10 minutes with microwave irradiation. After cooling, the reaction mixture was evaporated to dryness. The residue was dissolved in H₂O (10 ml) and extracted with ether. The ethereal layer was discarded. Then most of the water in the aqueous phase was removed in vacuo followed by addition of 10 ml of methanol. The crude product was purified with Prep-HPLC to give 1.163 g (yield 75%) of product. ¹H-NMR (400 MHz, CD₃OD): δ (ppm) 2.4 (s, 3H), 3.35 (m, 1H), 3.5 (m, 1H), 4.36 (m, 1H), 6.4 (s, 1H), 7.0 (s, 1H), 7.1 (m, 1H), 7.4 (m, 1H), 7.55 (m, 4H), 7.85 (s, 1H), 8.0 (d, 2H).

6.28. Synthesis of (S)-2-Amino-3-[4-(2-amino-6-{2,2,2-trifluoro-1-[4-(6-methoxy-pyridin-2-yl)-phenyl]-ethoxy}-pyrimidin-4-yl)-phenyl]-propionic acid

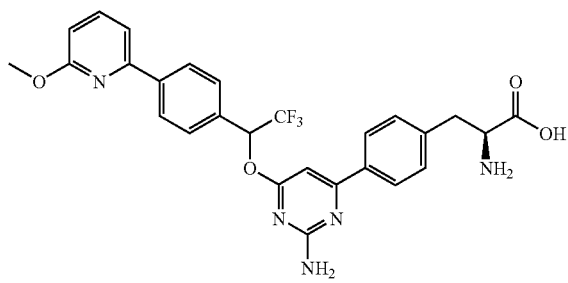

Tetrabutylammonium fluoride (TBAF) (0.1 ml of 1M in THF) was added to a solution of 4-(6-methoxy-pyridine-2-yl)-benzaldehyde (213 mg, 1 mmol) and trifluoromethyl trimethylsilane (0.2 ml, 1.2 mmol) in 10 ml THF at 0° C. The mixture was warmed up to room temperature and stirred for 4 hours. The reaction mixture was then treated with 12 ml of 1M HCl and stirred overnight. The product was extracted with ethyl acetate (3×20 ml). The organic layer was separated and dried over sodium sulfate. The organic solvent was evaporated to give 0.25 g of 1-[4-(6-methoxy-pyridine-2-yl)-phenyl]-2,2,2-trifluoro-ethanol which was directly used in next step without purification. yield: 90%.

Cs₂CO₃ (375 mg, 1 mmol) was added to a solution of 1-[4-(6-methoxy-pyridine-2-yl)-phenyl]-2,2,2-trifluoro-ethanol (67 mg, 0.2 mmol) in 10 ml of anhydrous 1,4-dioxane. The mixture was stirred for 5 min, then was added (S)-3-[4-(2-amino-6-chloro-pyrimidin-4-yl)-phenyl]-2-tert-butoxycarbonylamino-propionic acid (78 mg, 0.2 mmol), and the mixture was heated at 110° C. overnight. After cooling, 5 ml water was added and ethyl acetate (20 ml) was used to extract the product. The organic layer was dried over sodium sulfate. The solvent was removed by rotovap to give 112 mg (S)-3-[4-(2-Amino-6-{2,2,2-trifluoro-1-[4-(6-methoxy-pyridin-2-yl)-phenyl]-ethoxy}-pyrimidin-4-yl)-phenyl]-2-tert-butoxycarbonylamino-propionic acid (yield: 88%).

The above product (112 mg) was added into 5 ml of 30% TFA/DCM solution. Upon completion of the reaction, the solvent was evaporated to give a crude product, which was purified by preparative HPLC to give 5 mg of (S)-2-amino-3-[4-(2-amino-6-{2,2,2-trifluoro-1-[4-(6-methoxy-pyridin-2-yl)-phenyl]-ethoxy}-pyrimidin-4-yl)-phenyl]propionic acid. ¹H NMR (300 MHz, CD₃OD) δ (ppm) 8.18 (d, J=8.4 Hz, 2H), 7.94 (d, J=8.4 Hz, 2H), 7.74 (m, 3H), 7.60 (d, J=8.4 Hz, 2H), 7.52 (d, J=7.2 Hz, 1H), 7.08 (s, 1H), 6.86 (m, 1H), 6.82 (d, J=8.1 Hz 1H), 4.37 (t, 1H), 4.03 (s, 3H), 3.5 (m, 2H).

6.29. Synthesis of (S)-2-Amino-3-[4-(2-amino-6-{2,2,2-trifluoro-1-[2-fluoro-4-(5-methoxy-pyridin-3-yl)-phenyl]-ethoxy}-pyrimidin-4-yl)-phenyl]-propionic acid

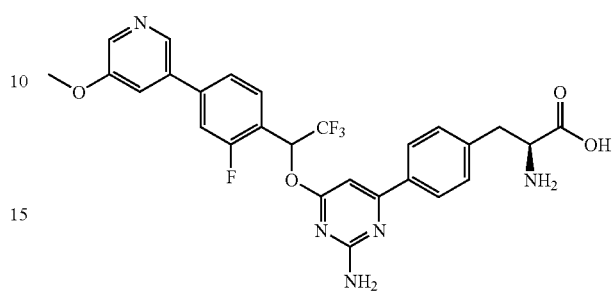

TBAF (0.1 ml) was added to a solution of 4-bromo-2-fluoro-benzaldehyde (2.03 g, 10 mmol) and TMSCF₃ (20 ml, 12 mmol) in 10 ml THF at 0° C. The formed mixture was warmed up to room temperature and stirred for 4 hours. The reaction mixture was then treated with 12 ml of 3M HCl and stirred overnight. The product was extracted with ethyl acetate (3×20 ml). The organic layer was separated and dried over sodium sulfate. The organic solvent was evaporated to give 2.4 g of 1-(4-bromo-2-fluoro-phenyl)-2,2,2-trifluoro-ethanol (yield: 90%).

Cs₂CO₃ (8.45 g, 26 mmol) was added to the solution of 1-(4-bromo-2-fluoro-phenyl)-2,2,2-trifluoro-ethanol (1.4 g, 5.2 mmol) in 10 ml of anhydrous 1,4-dioxane, the mixture was stirred for 5 minutes, then (S)-3-[4-(2-amino-6-chloro-pyrimidin-4-yl)-phenyl]-2-tert-butoxycarbonylamino-propionic acid (2.0 g, 5 mmol) was added, and the resulting mixture was heated at 110° C. overnight. After cooling, 5 ml of water was added and ethyl acetate (20 ml) was used to extract the product. The organic layer was dried over sodium sulfate. The solvent was removed by rotovap to give 2.6 g of (S)-3-(4-{2-amino-6-[1-(4-bromo-2-fluoro-phenyl)-2,2,2-trifluoro-ethoxy]-pyrimidin-4-yl} phenyl)2tertbutoxycarbonylamino-propionic acid (yield: 82%).

A microwave vial (2 ml) was charged with (S)-3-(4-{2-amino-6-[1-(4-bromo-2-fluoro-phenyl)-2,2,2-trifluoro-ethoxy]-pyrimidin-4-yl}-phenyl)-2-tert-butoxycarbonylamino-propionic acid (130 mg, 0.2 mmol), 3-methoxy-5-(4,4,5,5-tetramethyl-[1,3,2]dioxaborolan-2-yl)-pyridine (70 mg, 0.3 mmol) 1 ml of acetonitrile, and 0.7 ml of water. To this mixture was added 0.4 ml of aqueous sodium carbonate (1M), followed by 14 mg (5 mol %) of dichlorobis(triphenylphosphine) palladium(II). The reaction vessel was sealed and heated to 150° C. for 5 minutes with microwave irradiation. After cooling, the reaction mixture was evaporated to dryness, the residue was dissolved in 2.5 ml of methanol and purified with Prep HPLC to give 51 mg of (S)-3-[4-(2-amino-6-{2,2,2-trifluoro-1-[2-fluoro-4-(5-methoxy-pyridin-3-yl)-phenyl]-ethoxy}-pyrimidin-4-yl)-phenyl]-2-tert-butoxycarbonylamino-propionic acid.

The above-product (51 mg) was dissolved in 5 ml of 30% TFA/DCM solution. The mixture was stirred at room temperature overnight. Removal of solvent gave a crude product, which was purified by Prep HPLC to give 17 mg of (S)-2-amino-3-[4-(2-amino-6-{2,2,2-trifluoro-1-[2-fluoro-4-(5-methoxy-pyridin-3-yl)-phenyl]-ethoxy}-pyrimidin-4-yl)- phenyl]-propionic acid. $^1$H NMR (300 MHz, CD$_3$OD) δ (ppm): 8.73 (s, 1H), 8.56 (s, 1H), 8.25 (s, 1H), 7.94 (d, J=8.2 Hz, 2H), 7.77 (m, 3H), 7.55 (d, J=8.4 Hz, 2H), 7.16 (m, 1H), 7.00 (s, 1H), 4.35 (t, 1H), 4.09 (s, 3H), 3.4 (m, 2H).

6.30. Synthesis of (S)-2-Amino-3-[4-(2-amino-6-{(S)-2,2,2-trifluoro-1-[4-(2-fluoro-pyridin-4-yl)-phenyl]-ethoxy}-pyrimidin-4-yl)-phenyl]-propionic acid

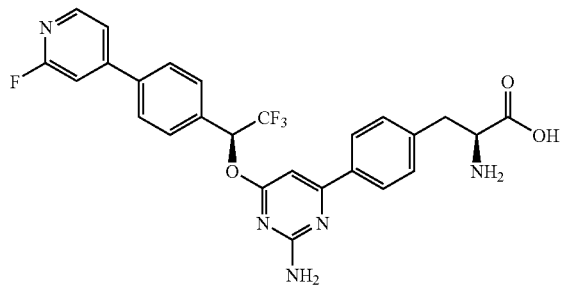

Cs$_2$CO$_3$ (16.25 g, 50 mmol) was added to the solution of (S)-1-(4-bromo-phenyl)-2,2,2-trifluoro-ethanol (2.55 g, 11.0 mmol) in 10 ml of anhydrous 1,4-dioxane, and the mixture was stirred for 5 minutes, after which (S)-3-[4-(2-amino-6-chloro-pyrimidin-4-yl)-phenyl]-2-tert-butoxycarbonylamino-propionic acid (3.92 g, 10 mmol) was added. The resulting mixture was heated at 110° C. overnight. After cooling, 5 ml of water was added and ethyl acetate (20 ml) was used to extract the product. The organic layer was dried over sodium sulfate. The solvent was removed by rotovap to give 5.2 g of (S)-3-(4-{2-amino-6-[(S)-1-(4-bromo-phenyl)-2,2,2-trifluoro-ethoxy]-pyrimidin-4-yl}phenyl)-2-tert-butoxy-carbonylamino-propionic acid (yield: 82%).

A microwave vial (2 ml) was charged with (S)-3-(4-{2-amino-6-[(S)-1-(4-bromo-phenyl)-2,2,2-trifluoro-ethoxy]-pyrimidin-4-yl}-phenyl)-2-tert-butoxycarbonylamino-propionic acid (139 mg, 0.23 mmol), 2-fluoropyridine-4-boronic acid (40 mg, 0.27 mmol) 1 ml of acetonitrile, and 0.7 ml of water. To this mixture, 0.4 ml of aqueous sodium carbonate (1M) was added, followed by 14 mg (5 mol %) of dichlorobis(triphenylphosphine)-palladium(II). The reaction vessel was sealed and heated to 150° C. for 5 minutes with microwave irradiation. After cooling, the reaction mixture was evaporated to dryness, and the residue was dissolved in 2.5 ml of methanol. The product was purified with Preparative HPLC to give 70 mg of (S)-3-[4-(2-amino-6-{(S)-2,2,2-trifluoro-1-[4-(2-fluoro-pyridin-4-yl)-phenyl]-ethoxy}-pyrimidin-4-yl)-phenyl]-2-tert-butoxycarbonylamino-propionic acid.

The above product (70 mg) was dissolved in 5 ml 30% TFA in DCM. The reaction mixture was stirred at r.t. overnight. Removal of solvent gave crude product which was purified by preparative HPLC to give 52 mg of (S)-2-amino-3-[4-(2-amino-6-{(S)-2,2,2-trifluoro-1-[4-(2-fluoro-pyridin-4-yl)-phenyl]-ethoxy}-pyrimidin-4-yl)-phenyl]-propionic acid. $^1$H NMR (300 MHz, CD$_3$OD) δ (ppm) 8.17 (d, J=5.7 Hz, 1H), 7.85 (d, J=8.4 Hz, 2H), 7.77 (d, J=6.9 Hz, 2H), 7.67 (d, J=8.2 Hz, 2H), 7.53 (m, 1H), 7.38 (d, J=8.4 Hz, 2H), 7.30 (s, 1H), 6.76 (m, 2H), 4.21 (t, 1H), 3.2 (m, 2H).

6.31. Synthesis of (S)-2-Amino-3-[4-(2-amino-6-{(S)-2,2,2-trifluoro-1-[4-(5-methoxy-pyridin-3-yl)-phenyl]-ethoxy}-pyrimidin-4-yl)-phenyl]-propionic acid

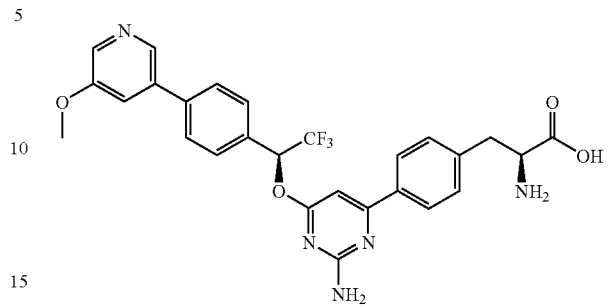

A microwave vial (2 ml) was charged with (S)-3-(4-{2-amino-6-[(S)-1-(4-bromo-phenyl)-2,2,2-trifluoro-ethoxy]-pyrimidin-4-yl}-phenyl)-2-tert-butoxycarbonylamino-propionic acid (139 mg, 0.23 mmol), 3-methoxy-5-(4,4,5,5-tetramethyl-[1,3,2]-dioxaborolan-2-yl)-pyridine (69 mg, 0.27 mmol), 1 ml of acetonitrile, and 0.7 ml of water. To this mixture was added 0.4 ml of aqueous sodium carbonate (1M), followed by 14 mg of dichlorobis-(triphenylphosphine)-palladium(II). The reaction vessel was sealed and heated to 150° C. for 5 minutes with microwave irradiation. After cooling, the reaction mixture was evaporated to dryness, the residue was dissolved in 2.5 ml of methanol and purified by preparative HPLC to give 60 mg of (S)-3-[4-(2-amino-6-{(S)-2,2,2-trifluoro-1-[4-(5-methoxy-pyridin-3-yl)-phenyl]-ethoxy}-pyrimidin-4-yl)-phenyl]-2-tert butoxycarbonylamino-propionic acid.

The above product (60 mg) was dissolved in 5 ml of 30% TFA in DCM. The reaction mixture was stirred at room temperature overnight. Removal of solvent gave a crude product which was purified by preparative HPLC to give 48 mg of (S)-2-amino-3-[4-(2-amino-6-{(S)-2,2,2-trifluoro-1-[4-(5-methoxy-pyridin-3-yl)-phenyl]-ethoxy}-pyrimidin-4-yl)-phenyl]-propionic acid. $^1$H NMR (300 MHz, CD$_3$OD) δ (ppm): 8.54 (d, J=1.5 Hz, 1H), 8.37 (d, J=2.7 Hz, 1H), 8.03 (dd, J=2.7 Hz, 1.5 Hz, 1H), 7.84 (d, J=8.2 Hz, 2H), 7.78 (d, J=8.4 Hz, 2H), 7.70 (d, J=8.4 Hz, 2H), 7.41 (d, J=8.4 Hz, 2H), 6.81 (s, 1H), 6.75 (m, 1H), 4.22 (t, 1H), 3.95 (t, 3H), 3.25 (m, 2H).

6.32. Synthesis of (S)-2-Amino-3-[4-(2-amino-6-{(S)-2,2,2-trifluoro-1-[4-(4-trifluoromethyl-pyridin-3-yl)-phenyl]-ethoxy}-pyrimidin-4-yl)-phenyl]-propionic acid

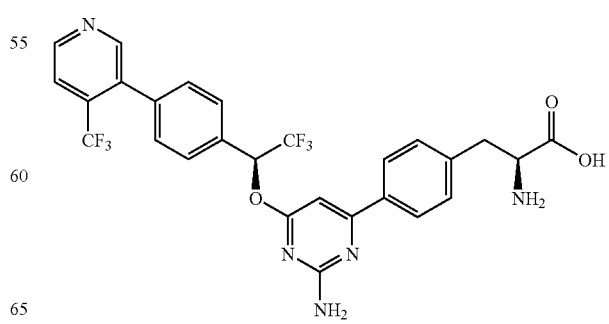

A microwave vial (2 ml) was charged with (S)-3-(4-{2-amino-6-[(S)-1-(4-bromo-phenyl)-2,2,2-trifluoro-ethoxy]-pyrimidin-4-yl}-phenyl)-2-tert-butoxycarbonylamino-propionic acid (139 mg, 0.23 mmol), 4-trifluoromethylpyridine-3-boronic acid (61 mg, 0.3 mmol), 1 ml of acetonitrile, and 0.7 ml of water. To this mixture was added 0.4 ml of aqueous sodium carbonate (1M), followed by 14 mg of dichlorobis(triphenylphosphine)-palladium(II). The reaction vessel was sealed and heated to 150° C. for 5 minutes with microwave irradiation. After cooling, the reaction mixture was evaporated to dryness, the residue was dissolved in 2.5 ml of methanol and was purified by preparative HPLC to give 20 mg of (S)-3-[4-(2-amino-6-{(S)-2,2,2-trifluoro-1-[4-(4-trifluoromethyl-pyridin-3-yl)-phenyl]-ethoxy}-pyrimidin-4-yl)-phenyl]-2-tert butoxycarbonylamino-propionic acid The above product (20 mg) was dissolved in 5 ml of 30% TFA in DCM. The reaction mixture was stirred at r.t. overnight. Removal of solvent gave crude product which purified by preparative HPLC to give 10 mg of (S)-2-amino-3-[4-(2-amino-6-{(S)-2,2,2-trifluoro-1-[4-(4-trifluoromethyl-pyridin-3-yl)-phenyl]-ethoxy}-pyrimidin-4-yl)-phenyl]-propionic acid. $^1$H NMR (300 MHz, CD$_3$OD) δ (ppm): 8.72 (d, J=5.1 Hz, 1H), 8.55 (s, 1H), 7.87 (d, J=8.2, 2H), 7.72 (d, J=5.0 Hz, 1H), 7.63 (d, J=8.2 Hz, 2H), 7.36 (m, 4H), 6.81 (m, 1H), 6.70 (s, 1H), 4.20 (t, 1H), 3.22 (m, 2H).

6.33. Synthesis of (S)-2-Amino-3-(4-{2-amino-6-[(S)-2,2,2-trifluoro-1-(4-isoxazol-4-yl-phenyl)-ethoxy]-pyrimidin-4-yl}-phenyl)-propionic acid

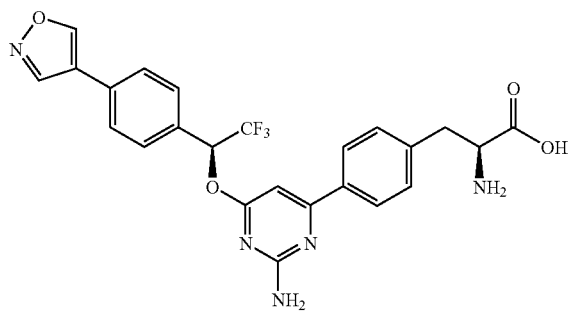

A microwave vial (2 ml) was charged with (S)-3-(4-{2-amino-6-[(S)-1-(4-bromo-phenyl)-2,2,2-trifluoro-ethoxy]-pyrimidin-4-yl}-phenyl)-2-tert-butoxycarbonylamino-propionic acid (139 mg, 0.23 mmol), 4-(4,4,5,5-tetramethyl-[1,3,2]dioxaborolan-2-yl)-isoxazole (57.5 mg, 0.3 mmol), 1 ml of acetonitrile, and 0.7 ml of water. To this mixture was added 0.4 ml of aqueous sodium carbonate (1M), followed by 14 mg of dichlorobis-(triphenylphosphine)-palladium(II). The reaction vessel was sealed and heated to 150° C. for 5 minutes with microwave irradiation. After cooling, the reaction mixture was evaporated to dryness, the residue was dissolved in 2.5 ml of methanol and was purified by preparative HPLC to give 20 mg of (S)-3-(4-{2-amino-6-[(S)-2,2,2-trifluoro-1-(4-isoxazol-4-yl-phenyl)-ethoxy]-pyrimidin-4-yl}-phenyl)-2-tert-butoxycarbonylamino propionic acid.

The above product (20 mg) was dissolved in 5 ml of 30% TFA in DCM. The mixture was stirred at r.t. overnight. Removal of solvent gave a crude product, which was purified by preparative HPLC to give 10 mg of (S)-2-amino-3-(4-{2-amino-6-[(S)-2,2,2-trifluoro-1-(4-isoxazol-4-yl-phenyl)-ethoxy]-pyrimidin-4-yl}-phenyl)-propionic acid. $^1$H NMR (300 MHz, CD$_3$OD) δ (ppm) 9.03 (s, 1H), 8.77 (s, 1H), 7.84 (m, 2H), 7.63 (d, J=8.2, 1H), 7.56 (d, J=8.4 Hz, 1H), 7.50 (m, 1H), 7.37 (m, 3H), 6.70 (m, 2H), 4.20 (t, 1H), 3.22 (m, 2H).

6.34. Synthesis of (S)-2-Amino-3-(4-{2-amino-6-[2,2,2-trifluoro-1-(2-pyrimidin-5-yl-phenyl)-ethoxy]-pyrimidin-4-yl}-phenyl)-propionic acid

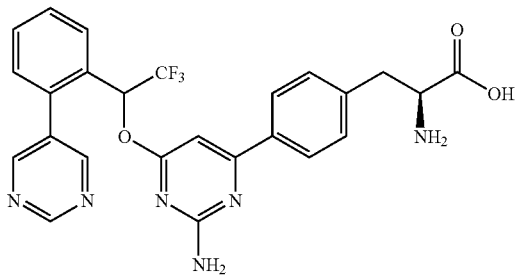

A microwave vial (20 ml) was charged with 2-formylphenylboronic acid (290 mg, 2.0 mmol), 5-bromo-pyrimidine (316 mg, 2.0 mmol) and 8 ml of acetonitrile. To this mixture was added 4 ml of aqueous sodium carbonate (1M), followed by 100 mg of dichlorobis-(triphenylphosphine)-palladium(II). The reaction vessel was sealed and heated at 150° C. for 5 minutes with microwave irradiation. After cooling, the reaction mixture was extracted with ethylacetate. The organic layer was evaporated to provide a crude material, which was purified by ISCO to give 220 mg of 2-pyrimidin-5-yl-benzaldehyde.

Tetrabutylammonium fluoride (TBAF, 0.1 ml of 1M in THF) was added to a solution of 2-pyrimidin-5-yl-benzaldehyde (184 mg, 1 mmol) and trifluoromethyl trimethylsilane (TMSCF$_3$, 0.2 ml, 1.2 mmol) in 10 ml THF at 0° C. The mixture was warmed up to room temperature and stirred for 4 hours. The mixture was then treated with 3 ml of 1M HCl and stirred overnight. The product was extracted with ethyl acetate (3×20 ml). The organic layer was separated and dried over sodium sulfate. The organic solvent was evaporated to give 0.21 g of 2,2,2-trifluoro-1-(2-pyrimidin-5-yl-phenyl)-ethanol (yield: 84%), which was directly used in next step without purification.

Cs$_2$CO$_3$ (325 mg, 1.0 mmol) was added to a solution of 2,2,2-trifluoro-1-(2-pyrimidin-5-yl-phenyl)-ethanol (72 mg, 0.28 mmol) in 10 ml of anhydrous THF. The mixture was stirred for 20 min, 2-amino-4,6-dichloro-pyrimidine (36.7 mg, 0.22 mmol) was added and then the reaction mixture was heated at 110° C. until the reaction was completed. After cooling to room temperature, 5 ml of water was added and ethyl acetate (20 ml) was used to extract the product. The organic layer was dried over sodium sulfate. The solvent was removed by rotovap to give 76 mg of crude 4-chloro-6-[2,2,2-trifluoro-1-(2-pyrimidin-5-yl-phenyl)-ethoxy]-pyrimidin-2-ylamine (yield: 92%).

A microwave vial (2 ml) was charged with above crude intermediate (38 mg, 0.1 mmol), 4-borono-L-phenylalanine (31 mg, 0.15 mmol), 1 ml of acetonitrile, and 0.7 ml of water. To this mixture was added 0.3 ml of aqueous sodium carbonate (1M), followed by 4 mg, 5 mol % of dichlorobis(triphenylphosphine)-palladium(II). The reaction vessel was sealed and heated to 150° C. for 5 minutes with microwave irradiation. After cooling, the reaction mixture was evaporated to dryness, the residue was dissolved in 2.5 ml of methanol and then purified with preparative HPLC to give 10 mg of (S)-2-amino-3-(4-{2-amino-6-[2,2,2-trifluoro-1-(2-pyrimidin-5-yl-phenyl)-ethoxy]-pyrimidin-4-yl}-phenyl)-propionic acid. ¹H NMR (300 MHz, CD₃OD) δ (ppm) 9.21 (s, 1H), 8.87 (s, 2H), 7.86 (d, J=8.4, 2H), 7.75 (m, 1H), 7.53 (m, 2H), 7.37 (d, J=8.2, 1H), 7.33 (m, 1H), 6.72 (s, 1H), 6.58 (m, 1H), 4.20 (t, 1H), 3.22 (m, 2H).

6.35. Synthesis of (S)-2-amino-3-(4-{2-amino-6-[2,2,2-trifluoro-1-(2-thiophen-3-yl-phenyl)-ethoxy]-pyrimidin-4-yl}-phenyl)-propionic acid

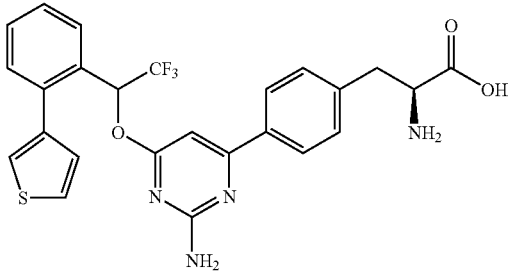

A microwave vial (20 ml) was charged with 2-formylphenylboronic acid (290 mg, 2.0 mmol), 3-bromo-thiophene (326 mg, 2.0 mmol), and 8 ml of acetonitrile. To this mixture was added 4 ml of aqueous sodium carbonate (1M), followed by 50 mg of dichlorobis-(triphenylphosphine)-palladium(II). The reaction vessel was sealed and heated at 150° C. for 5 minutes with microwave irradiation. After cooling, the reaction mixture was extracted with ethylacetate. The organic layer was evaporated to provide a crude material, which was purified by ISCO to give 211 mg of 2-thiophen-3-yl-benzaldehyde.

Tetrabutylammonium fluoride (TBAF, 0.1 ml of 1M in THF) was added to a solution of 2-thiophen-3-yl-benzaldehyde (100 mg, 0.53 mmol) and trifluoromethyl trimethylsilane (0.1 ml, 0.64 mmol) in 10 ml THF at 0° C. The mixture was warmed up to room temperature and stirred for 4 hours. The mixture was then treated with 3 ml of 1M HCl and stirred overnight. The product was extracted with ethyl acetate (3×20 ml). The organic layer was separated and dried over sodium sulfate. The organic solvent was evaporated to give 0.12 g of 2,2,2-trifluoro-1-(2-pyrimidin-5-yl-phenyl)-ethanol, which was directly used in next step without purification (yield: 89%).

Cs₂CO₃ (325 mg, 1.0 mmol) was added to a solution of 2,2,2-trifluoro-1-(2-thiophen-3-yl-phenyl)-ethanol (72 mg, 0.28 mmol) in 10 ml of anhydrous THF, and the mixture was stirred for 20 minutes. 2-Amino-4,6-dichloro-pyrimidine (36.7 mg, 0.22 mmol) was then added, and the mixture was heated 110° C. until the reaction was complete. After cooling, 5 ml of water was added, and ethyl acetate (20 ml) was used to extract the product. The organic layer was dried over sodium sulfate. The solvent was removed by rotovap to give 67 mg of 4-chloro-6-[2,2,2-trifluoro-1-(2-pyrimidin-5-yl-phenyl)-ethoxy]-pyrimidin-2-ylamine (yield: 78%).

A microwave vial (2 ml) was charged with above crude material (40 mg, 0.1 mmol), 4-borono-L-phenylalanine (31 mg, 0.15 mmol), 1 ml of acetonitrile, and 0.7 ml of water. To this mixture was added 0.3 ml of aqueous sodium carbonate (1M), followed by 5 mol % dichlorobis(triphenylphosphine)-palladium(II). The reaction vessel was sealed and heated at 150° C. for 5 minutes with microwave iiradiation. After cooling, the reaction mixture was evaporated to dryness. The residue was dissolved in 2.5 ml of methanol and then purified with preparative HPLC to afford 11.8 mg of (S)-2-amino-3-(4-{2-amino-6-[2,2,2-trifluoro-1-(2-thiophen-3-yl-phenyl)-ethoxy]-pyrimidin-4-yl}-phenyl)-propionic acid. ¹H NMR (300 MHz, CD₃OD) δ (ppm): 7.84 (d, J=8.0 Hz, 2H), 7.66 (d, J=7.6 Hz, 1H), 7.53 (m, 1H), 7.40 (m, 5H), 7.30 (m, 1H), 7.17 (m, 1H), 6.91 (m, 1H), 6.82 (s, 1H), 4.23 (t, 1H), 3.25 (m, 2H).

6.36. Synthesis of (S)-2-Amino-3-[4-(2-amino-6-{2,2,2-trifluoro-1-[2-(1-methyl-1H-pyrazol-4-yl)-phenyl]-ethoxy}-pyrimidin-4-yl)-phenyl]-propionic acid

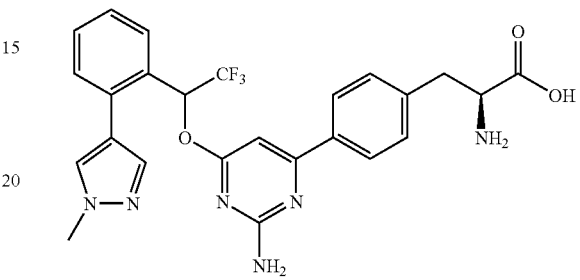

A microwave vial (20 ml) was charged with 2-bromo-benzaldehyde (208 mg, 1.0 mmol), 1-methyl-4-(4,4,5,5-tetramethyl-[1,3,2]dioxaborolan-2-yl)-1H-pyrazole (222 mg, 1.2 mmol) and 8 ml of acetonitrile. To this mixture was added 2.4 ml of aqueous sodium carbonate (1M), followed by 50 mg of dichlorobis(triphenylphosphine)-palladium(II). The reaction vessel was sealed and heated at 150° C. for 5 minutes with microwave irradiation. After cooling, the reaction mixture was extracted with ethylacetate. The organic layer was evaporated to provide crude material which was purified by ISCO to give 181 mg of 2-(1-methyl-1H-pyrazol-4-yl)-benzaldehyde (96% yield).

Tetrabutylammonium fluoride (0.1 ml of 1M in THF) was added to a solution of 2-(1-methyl-1H-pyrazol-4-yl)-benzaldehyde (100 mg, 0.53 mmol) and trifluoromethyl trimethylsilane (0.12 ml, 0.6 mmol) in 10 ml THF at 0° C. The mixture was warmed up to room temperature and stirred for 4 hours. The mixture was then treated with 3 ml of 1M HCl and stirred overnight. The product was extracted with ethyl acetate (3×20 ml). The organic layer was separated and dried over sodium sulfate. The organic solvent was evaporated to give 0.12 g of 2,2,2-trifluoro-1-[2-(1-methyl-1H-pyrazol-4-yl-phenyl)-ethanol, which was directly used in next step without purification (yield: 89%).

Cs₂CO₃ (325 mg, 1.0 mmol) was added to a solution of 2,2,2-trifluoro-1-[2-(1-methyl-1H-pyrazol-4-yl)-phenyl]-ethanol (60 mg, 0.2 mmol) in 10 ml of anhydrous THF, and the mixture was stirred for 20 minutes. 2-Amino-4,6-dichloro-pyrimidine (32 mg, 0.2 mmol) was added, and then the reaction mixture was heated at 110° C. until the reaction was complete. After cooling, 5 ml of water was added, and ethyl acetate (20 ml) was used to extract the product. The organic layer was dried over sodium sulfate. The solvent was removed by rotovap to afford 70 mg of 4-chloro-6-{2,2,2-trifluoro-1-[2-(1-methyl-1H-pyrazol-4-yl)-phenyl]-ethoxy}-pyrimidin-2-ylamine (yield: 92%).

A microwave vial (2 ml) was charged with above crude material (38 mg, 0.1 mmol), 4-borono-L-phenylalanine (31 mg, 0.15 mmol), 1 ml of acetonitrile, and 0.7 ml of water. To this mixture was added 0.3 ml of aqueous sodium carbonate (1M), followed by 5 mol % of dichlorobis(triphenylphosphine)-palladium(II). The reaction vessel was sealed and heated to 150° C. for 5 minutes with microwave irradiation. After cooling, the mixture was evaporated to dryness, the residue was dissolved in 2.5 ml of methanol and then purified by preparative HPLC to give 5.6 mg of (S)-2-amino-3-[4-(2-amino-6-{2,2,2-trifluoro-1-[2-(1-methyl-1H-pyrazol-4-yl)-phenyl]-ethoxy}-pyrimidin-4-yl)-phenyl]-propionic acid.

6.37. Synthesis of (S)-2-amino-3-(4-{6-[2,2,2-trifluoro-1-(2-furan-3-yl-phenyl)-ethoxy]-pyrimidin-4-yl}-phenyl)-propionic acid

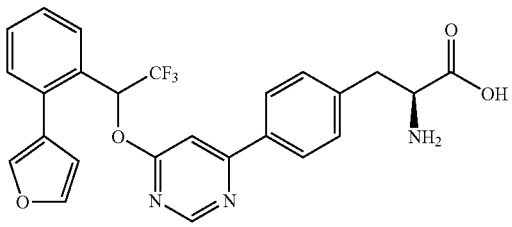

A microwave vial (20 ml) was charged with 2-formylphenylboronic acid (298 mg, 2.0 mmol), 3-bromo-furan (350 mg, 2.4 mmol) and 8 ml of acetonitrile. To this mixture was added 4 ml of aqueous sodium carbonate (1M), followed by 100 mg of dichlorobis-(triphenylphosphine)-palladium(II). The reaction vessel was sealed and heated at 150° C. for 5 minutes with microwave irradiation. After cooling, the reaction mixture was extracted with ethylacetate. The organic layer was evaporated to provide crude material which was purified by ISCO to give 110 mg of 2-furan-3-yl-benzaldehyde (30% yield).

Tetrabutylammonium fluoride (0.1 ml of 1M in THF) was added to a solution of 2-furan-3-yl-benzaldehyde (110 mg, 0.64 mmol) and trifluoromethyl trimethylsilane (109 mg, 0.78 mmol) in 10 ml THF at 0° C. The mixture was warmed up to room temperature and stirred for 4 hours. The mixture was then treated with 3 ml of 1M HCl and stirred overnight. The product was extracted with ethyl acetate (3×20 ml). The organic layer was separated and dried over sodium sulfate. The organic solvent was evaporated to give 0.130 g of 2,2,2-trifluoro-1-(2-furan-3-yl-phenyl)-ethanol, which was directly used in next step without purification (yield: 90%).

Sixty percent NaH (12 mg, 0.3 mmol) was added to a solution of 2,2,2-trifluoro-1-(2-furan-3-yl-phenyl)-ethanol (54 mg, 0.2 mmol) in 10 ml of anhydrous THF. The mixture was stirred for 20 minutes, after which 4,6-dichloro-pyrimidine (30 mg, 0.2 mmol) was added. The mixture was then heated at 70° C. until the reaction was complete. After cooling, 5 ml of water was added to quench the reaction, and ethyl acetate (20 ml) was used to extract the product. The organic layer was dried over sodium sulfate. The solvent was removed by rotovap to give of 67 mg 4-chloro-6-[2,2,2-trifluoro-1-(2-furan-3-yl-phenyl)-ethoxy]-pyrimidine (yield: 94%).

A microwave vial (2 ml) was charged with above crude material (38 mg, 0.1 mmol), 4-borono-L-phenylalanine (31 mg, 0.15 mmol), 1 ml of acetonitrile, and 0.7 ml of water. To this mixture was added 0.3 ml of aqueous sodium carbonate (1M), followed by 5 mol % of dichlorobis(triphenylphosphine)-palladium(II). The reaction vessel was sealed and heated to 150° C. for 5 minutes with microwave irradiation. After cooling, the reaction mixture was evaporated to dryness, the residue was dissolved in 2.5 ml of methanol and then purified by preparative HPLC to afford 6 mg of (S)-2-amino-3-(4-{6-[2,2,2-trifluoro-1-(2-furan-3-yl-phenyl)-ethoxy]-pyrimidin-4-yl}-phenyl)-propionic acid. $^1$H NMR (300 MHz, CD$_3$OD) δ (ppm): 8.82 (s, 1H), 8.13 (d, J=8.4 Hz, 2H), 7.73 (m, 2H), 7.46 (m, 6H), 6.82 (m, 1H), 6.54 (s, 1H), 4.20 (t, 1H), 3.22 (m, 2H).

6.38. Synthesis of (S)-2-amino-3-(4-{6-[2,2,2-trifluoro-1-(2-furan-2-yl-phenyl)-ethoxy]-pyrimidin-4-yl}-phenyl)-propionic acid

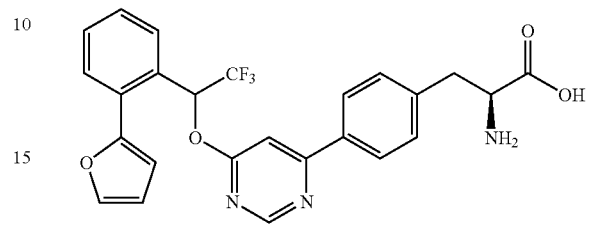

A microwave vial (20 ml) was charged with 2-formylphenylboronic acid (298 mg, 2.0 mmol), 2-bromo-furan (350 mg, 2.4 mmol) and 8 ml of acetonitrile. To this mixture was added 4 ml of aqueous sodium carbonate (1M), followed by 100 mg of dichlorobis-(triphenylphosphine)-palladium(II). The reaction vessel was sealed and heated at 150° C. for 5 minutes with microwave irradiation. After cooling, the reaction mixture was extracted with ethylacetate. The organic layer was evaporated to provide a crude material, which was purified by ISCO to give 123 mg of 2-furan-2-yl-benzaldehyde (34% yield).

Tetrabutylammonium fluoride (0.1 ml of 1M in THF) was added to a solution of 2-furan-2-yl-benzaldehyde (123 mg, 0.71 mmol) and trifluoromethyl trimethylsilane (120 mg, 0.86 mmol) in 10 ml THF at 0° C. The mixture was warmed up to room temperature and stirred for 4 hours. The reaction mixture was then treated with 3 ml of 1M HCl and stirred overnight. The product was extracted with ethyl acetate (3×20 ml). The organic layer was separated and dried over sodium sulfate. The organic solvent was evaporated to give 0.150 g of 2,2,2-trifluoro-1-(2-furan-3-yl-phenyl)-ethanol, which was directly used in next step without purification (yield: 90%).

Sixty percent NaH (12 mg, 0.3 mmol) was added to a solution of 2,2,2-trifluoro-1-(2-furan-2-yl-phenyl)-ethanol (55 mg, 0.2 mmol) in 10 ml of anhydrous THF. The mixture was stirred for 20 minutes, after which 4,6-dichloro-pyrimidine (29 mg, 0.2 mmol) was added. The mixture was then heated at 110° C. until the reaction was complete. After cooling, 5 ml of water was added, and ethyl acetate (20 ml) was used to extract the product. The organic layer was dried over sodium sulfate. The solvent was removed by rotovap to give 60 mg of 4-chloro-6-[2,2,2-trifluoro-1-(2-furan-2-yl-phenyl)-ethoxy]-pyrimidine (yield 80%).

A microwave vial (2 ml) was charged with the above crude material (60 mg, 0.2 mmol), 4-borono-L-phenylalanine (62 mg, 0.3 mmol), 1 ml of acetonitrile, and 0.6 ml of water. To this mixture was added 0.4 ml of aqueous sodium carbonate (1M), followed by 5 mol % of dichlorobis(triphenylphosphine)-palladium(II). The reaction vessel was sealed and heated to 150° C. for 5 minutes with microwave irradiation. After cooling, the reaction mixture was evaporated to dryness, the residue was dissolved in 2.5 ml of methanol and purified by preparative HPLC to give 6 mg of (S)-2-amino-3-(4-{6-[2,2,2-trifluoro-1-(2-furan-2-yl-phenyl)-ethoxy]-pyrimidin-4-yl}-phenyl)-propionic acid. $^1$H NMR (300 MHz, CD$_3$OD) δ (ppm): 8.66 (s, 1H), 8.11 (d, J=8.4 Hz, 2H), 7.77 (m, 2H), 7.54 (m, 6H), 6.86 (d, J=3.3 Hz, 1H), 6.66 (m, 1H), 4.20 (t, 1H), 3.22 (m, 2H).

6.39. Additional Compounds

Additional compounds prepared using methods known in the art and/or described herein are listed below:

| Compound | LCMS (M + 1) | HPLC Method (Time (min)) |
|---|---|---|
| (2S)-2-amino-3-(4-(2-amino-6-(2,2,2-trifluoro-1-(4-(pyridin-3-yl)phenyl)ethoxy)pyrimidin-4-yl)phenyl)propanoic acid | 510 | A — |
| (2S)-2-amino-3-(4-(2-amino-6-(2,2,2-trifluoro-1-(2-(2-methylpyridin-4-yl)phenyl)ethoxy)pyrimidin-4-yl)phenyl)propanoic acid | 524 | A — |
| (2S)-2-amino-3-(4-(2-amino-6-(2,2,2-trifluoro-1-(2-(4-methylthiophen-3-yl)phenyl)ethoxy)pyrimidin-4-yl)phenyl)propanoic acid | 529 | A — |
| (2S)-3-(4-(6-(1-(2-(1H-pyrazol-1-yl)phenyl)-2,2,2-trifluoroethoxy)-2-aminopyrimidin-4-yl)phenyl)-2-aminopropanoic acid | 499 | A (2.86) |
| (2S)-2-amino-3-(4-(2-amino-6-(2,2,2-trifluoro-1-(4-(furan-2-yl)phenyl)ethoxy)pyrimidin-4-yl)phenyl)propanoic acid | 499 | A — |
| (2S)-2-amino-3-(4-(6-(2,2,2-trifluoro-1-(2-(pyridin-3-yloxy)phenyl)ethoxy)pyrimidin-4-yl)phenyl)propanoic acid | 512 | A (1.36) |
| (2S)-3-(4-(6-(1-(2-(1H-1,2,4-triazol-1-yl)phenyl)-2,2,2-trifluoroethoxy)-2-aminopyrimidin-4-yl)phenyl)-2-aminopropanoic acid | 500 | A (2.17) |
| (2S)-2-amino-3-(4-(2-amino-6-(2,2,2-trifluoro-1-(2-(furan-3-yl)phenyl)ethoxy)pyrimidin-4-yl)phenyl)propanoic acid | 499 | A — |
| (2S)-2-amino-3-(4-(2-amino-6-(2,2,2-trifluoro-1-(4-(furan-2-yl)-3-methoxyphenyl)ethoxy)pyrimidin-4-yl)phenyl)propanoic acid | 529 | A (3.32) |
| (2S)-2-amino-3-(4-(5-(2,2,2-trifluoro-1-(2-(furan-2-yl)phenyl)ethoxy)pyrazin-2-yl)phenyl)propanoic acid | 484 | E — |
| (2S)-3-(4-(5-(1-(2-(1H-pyrazol-1-yl)phenyl)-2,2,2-trifluoroethoxy)pyrazin-2-yl)phenyl)-2-aminopropanoic acid | 484 | E — |
| (2S)-2-amino-3-(4-(2-amino-6-(1-(4,5-dimethoxy-2-(1H-pyrazol-1-yl)phenyl)-2,2,2-trifluoroethoxy)pyrimidin-4-yl)phenyl)propanoic acid | 559 | A (2.86) |
| (2S)-2-amino-3-(4-(2-amino-6-(2,2,2-trifluoro-1-(2-(2-methyl-1H-imidazol-1-yl)phenyl)ethoxy)pyrimidin-4-yl)phenyl)propanoic acid | 513 | A (2.30) |
| (2S)-2-amino-3-(4-(2-amino-6-(2,2,2-trifluoro-1-(2-(5-methylthiophen-2-yl)phenyl)ethoxy)pyrimidin-4-yl)phenyl)propanoic acid | 529 | A — |
| (2S)-2-amino-3-(4-(2-amino-6-(1-(2-(5-(dimethylcarbamoyl)furan-2-yl)phenyl)-2,2,2-trifluoroethoxy)pyrimidin-4-yl)phenyl)propanoic acid | 570 | A — |
| (2S)-2-amino-3-(4-(2-amino-6-(2,2,2-trifluoro-1-(4-fluoro-2-(thiophen-2-yl)phenyl)ethoxy)pyrimidin-4-yl)phenyl)propanoic acid | 533 | A (1.61) |
| (2S)-2-amino-3-(4-(6-(2,2,2-trifluoro-1-(4-fluoro-2-(thiophen-2-yl)phenyl)ethoxy)pyrimidin-4-yl)phenyl)propanoic acid | 518 | A (1.65) |
| (2S)-2-amino-3-(4-(6-(2,2,2-trifluoro-1-(4-fluoro-2-(thiophen-3-yl)phenyl)ethoxy)pyrimidin-4-yl)phenyl)propanoic acid | 518 | A (3.76) |
| (2S)-2-amino-3-(4-(6-(2,2,2-trifluoro-1-(4-fluoro-2-(4-methylthiophen-2-yl)phenyl)ethoxy)pyrimidin-4-yl)phenyl)propanoic acid | 532 | A (3.88) |
| (S)-2-amino-3-(4-(2-amino-6-((R)-2,2,2-trifluoro-1-(4-(6-fluoropyridin-3-yl)phenyl)ethoxy)pyrimidin-4-yl)phenyl)propanoic acid | 528 | A (2.96) |
| (2S)-3-(4-(6-(1-(4-(1H-imidazol-1-yl)phenyl)-2,2,2-trifluoroethoxy)-2-aminopyrimidin-4-yl)phenyl)-2-aminopropanoic acid | 499 | A (2.07) |
| (2S)-2-amino-3-(4-(6-(2,2,2-trifluoro-1-(4-(thiophen-2-yl)phenyl)ethoxy)pyrimidin-4-yl)phenyl)propanoic acid | 500 | A (3.74) |
| (S)-2-amino-3-(4-(2-amino-6-((R)-2,2,2-trifluoro-1-(4-(pyrimidin-5-yl)phenyl)ethoxy)pyrimidin-4-yl)phenyl)propanoic acid | 511 | A (2.67) |
| (2S)-2-amino-3-(4-(6-(1-(2-(3,5-dimethylisoxazol-4-yl)-4-fluorophenyl)-2,2,2-trifluoroethoxy)pyrimidin-4-yl)phenyl)propanoic acid | 531 | A (1.55) |
| (S)-2-amino-3-(4-(2-amino-6-((R)-2,2,2-trifluoro-1-(4-(2-methylpyridin-4-yl)phenyl)ethoxy)pyrimidin-4-yl)phenyl)propanoic acid | 524 | A (2.28) |
| (2S)-3-(4-(6-(1-(4-(1H-1,2,4-triazol-1-yl)phenyl)-2,2,2-trifluoroethoxy)pyrimidin-4-yl)phenyl)-2-aminopropanoic acid | 485 | A (1.24) |
| (2S)-2-amino-3-(4-(2-amino-6-(2,2,2-trifluoro-1-(4-(piperidin-1-ylmethyl)phenyl)ethoxy)pyrimidin-4-yl)phenyl)propanoic acid | 530 | B (3.00) |

-continued

| Compound | LCMS (M + 1) | HPLC Method (Time (min)) |
| --- | --- | --- |
| (2S)-2-amino-3-(4-(2-amino-6-(2,2,2-trifluoro-1-(2-fluoro-4-(2-methylpyridin-4-yl)phenyl)ethoxy)pyrimidin-4-yl)phenyl)propanoic acid | 542 | A (2.42) |
| (2S)-2-amino-3-(4-(2-amino-6-(1-(4-(6-chloropyridazin-3-yl)phenyl)-2,2,2-trifluoroethoxy)pyrimidin-4-yl)phenyl)propanoic acid | 545 | A (3.33) |
| (2S)-2-amino-3-(4-(2-amino-6-(1-(4-(4-tert-butylthiazol-2-yl)phenyl)-2,2,2-trifluoroethoxy)pyrimidin-4-yl)phenyl)propanoic acid | 572 | A (1.82) |
| (2S)-2-amino-3-(4-(2-amino-6-(2,2,2-trifluoro-1-(3'-methoxy-3-(3-methyl-1H-pyrazol-1-yl)biphenyl-4-yl)ethoxy)pyrimidin-4-yl)phenyl)propanoic acid | 619 | A (3.54) |
| (2S)-2-amino-3-(4-(2-amino-6-(1-(5-chloro-2-(3-methyl-1H-pyrazol-1-yl)phenyl)-2,2,2-trifluoroethoxy)pyrimidin-4-yl)phenyl)propanoic acid | 547 | A (3.20) |

6.40. In Vitro Inhibition Assays

Human TPH1, TPH2, tyrosine hydroxylase (TH) and phenylalanine hydroxylase (PH) were all generated using genes having the following accession numbers, respectively: X52836, AY098914, X05290, and U49897.

The full-length coding sequence of human TPH1 was cloned into the bacterial expression vector pET24 (Novagen, Madison, Wis., USA). A single colony of BL21(DE3) cells harboring the expression vector was inoculated into 50 ml of L broth (LB)-kanamycin media and grown up at 37° C. overnight with shaking. Half of the culture (25 ml) was then transferred into 3 L of media containing 1.5% yeast extract, 2% Bacto Peptone, 0.1 mM tryptophan, 0.1 mM ferrous ammonium sulfate, and 50 mM phosphate buffer (pH 7.0), and grown to $OD_{600}$=6 at 37° C. with oxygen supplemented at 40%, pH maintained at 7.0, and glucose added. Expression of TPH1 was induced with 15% D-lactose over a period of 10 hours at 25° C. The cells were spun down and washed once with phosphate buffered saline (PBS).

TPH1 was purified by affinity chromatography based on its binding to pterin. The cell pellet was resuspended in a lysis buffer (100 ml/20 g) containing 50 mM Tris-Cl, pH 7.6, 0.5 M NaCl, 0.1% Tween-20, 2 mM EDTA, 5 mM DTT, protease inhibitor mixture (Roche Applied Science, Indianapolis, Ind., USA) and 1 mM phenylmethanesulfonyl fluoride (PMSF), and the cells were lyzed with a microfluidizer. The lysate was centrifuged and the supernatant was loaded onto a pterin-coupled sepharose 4B column that was equilibrated with a buffer containing 50 mM Tris, pH 8.0, 2 M NaCl, 0.1% Tween-20, 0.5 mM EDTA, and 2 mM DTT. The column was washed with 50 ml of this buffer and TPH1 was eluted with a buffer containing 30 mM $NaHCO_3$, pH 10.5, 0.5 M NaCl, 0.1% Tween-20, 0.5 mM EDTA, 2 mM DTT, and 10% glycerol. Eluted enzyme was immediately neutralized with 200 mM $KH_2PO_4$, pH 7.0, 0.5 M NaCl, 20 mM DTT, 0.5 mM EDTA, and 10% glycerol, and stored at −80° C.

Human tryptophan hydroxylase type II (TPH2), tyrosine hydroxylase (TH) and phenylalanine hydroxylase (PAH) were expressed and purified essentially in the same way, except the cells were supplemented with tyrosine for TH and phenylalanine for PAH during growth.

TPH1 and TPH2 activities were measured in a reaction mixture containing 50 mM 4-morpholinepropanesulfonic acid (MOPS), pH 7.0, 60 µM tryptophan, 100 mM ammonium sulfate, 100 µM ferrous ammonium sulfate, 0.5 mM tris(2-carboxyethyl)phosphine (TCEP), 0.3 mM 6-methyl tetrahydropterin, 0.05 mg/ml catalase, and 0.9 mM DTT. The reactions were initiated by adding TPH1 to a final concentration of 7.5 nM. Initial velocity of the reactions was determined by following the change of fluorescence at 360 nm (excitation wavelength=300 nm). TPH1 and TPH2 inhibition was determined by measuring their activities at various compound concentrations, and the potency of a given compound was calculated using the equation:

$$v = b + \frac{v_0 - b}{1 + \left(\frac{[C]}{[I_{c50}]}\right)^D}$$

where v is the initial velocity at a given compound concentration C, $v_0$ is the v when C=0, b is the background signal, D is the Hill slope which is approximately equal to 1, and $I_{c50}$ is the concentration of the compound that inhibits half of the maximum enzyme activity.

Human TH and PAH activities were determined by measuring the amount of $^3H_2O$ generated using L-[3,4-$^3$H]-tyrosine and L-[4-$^3$H]-phenylalanine, respectively. The enzyme (100 nM) was first incubated with its substrate at 0.1 mM for about 10 minutes, and added to a reaction mixture containing 50 mM MOPS, pH 7.2, 100 mM ammonium sulfate, 0.05% Tween-20, 1.5 mM TCEP, 100 µM ferrous ammonium sulfate, 0.1 mM tyrosine or phenylalanine, 0.2 mM 6-methyl tetrahydropterin, 0.05 mg/ml of catalase, and 2 mM DTT. The reactions were allowed to proceed for 10-15 minutes and stopped by the addition of 2 M HCl. The mixtures were then filtered through activated charcoal and the radioactivity in the filtrate was determined by scintillation counting. Activities of compounds on TH and PAH were determined using this assay and calculated in the same way as on TPH1 and TPH2.

6.41. Cell-Based Inhibition Assays

Two types of cell lines were used for screening: RBL2H3 is a rat mastocytoma cell line, which contains TPH1 and makes 5-hydroxytryotamine (5HT) spontaneously; BON is a human carcinoid cell line, which contains TPH1 and makes 5-hydroxytryptophan (5HTP). The CBAs were performed in 96-well plate format. The mobile phase used in HPLC contained 97% of 100 mM sodium acetate, pH 3.5 and 3% acetonitrile. A Waters C18 column (4.6×50 mm) was used with Waters HPLC (model 2795). A multi-channel fluorometer (model 2475) was used to monitor the flow through by setting at 280 nm as the excitation wavelength and 360 nm as the emission wavelength.

RBL CBA: Cells were grown in complete media (containing 5% bovine serum) for 3-4 hours to allow cells to attach to plate wells (7K cell/well). Compounds were then added to each well in the concentration range of 0.016 μM to 11.36 μM. The controls were cells in complete media without any compound present. Cells were harvested after 3 days of incubation at 37° C. Cells were >95% confluent without compound present. Media were removed from plate and cells were lysed with equal volume of 0.1 N NaOH. A large portion of the cell lysate was treated by mixing with equal volume of 1M TCA and then filtered through glass fiber. The filtrates were loaded on reverse phase HPLC for analyzing 5HT concentrations. A small portion of the cell lysate was also taken to measure protein concentration of the cells that reflects the cytotoxicity of the compounds at the concentration used. The protein concentration was measured by using BCA method.

The average of 5HT level in cells without compound treated was used as the maximum value in the $IC_{50}$ derivation according to the equation provided above. The minimum value of 5HT is either set at 0 or from cells that treated with the highest concentration of compound If a compound is not cytotoxic at that concentration.

BON CBA: Cells were grown in equal volume of DMEM and F12K with 5% bovine serum for 3-4 hours (20K cell/well) and compound was added at a concentration range of 0.07 μM to 50 μM. The cells were incubated at 37° C. overnight. Fifty μM of the culture supernatant was then taken for 5HTP measurement. The supernatant was mixed with equal volume of 1M TCA, then filtered through glass fiber. The filtrate was loaded on reverse phase HPLC for 5HTP concentration measurement. The cell viability was measured by treating the remaining cells with Promega Celltiter-Glo Luminescent Cell Viability Assay. The compound potency was then calculated in the same way as in the RBL CBA.

6.42. In Vivo Effects

The in vivo effects of compound were determined by formulating them to provide solutions, which were then orally dosed. In general, 14-week-old male C57 albino mice were dosed once daily by oral gavage at 5-10 ml/kg for four consecutive days. Five hours after the last dose, the animals were quickly sacrificed. Each animal was anesthetized using isoflurane, blood was drawn by cardiac stick method using 1 ml syringes and 25⅝ needle, 250 μl blood was placed in capiject EDTA containing tubes which were kept on gentle rotating. The animal was then decapitated, whole brain was taken and snap frozen, jejunum, ileum and colon were cleaned from fat and lumen content, snap frozen. 5-HT was extracted from the blood or tissues and measured by high performance liquid chromatography (HPLC) equipped with an in-line fluorescence detector. Blood samples were taken for exposure analysis. All animal studies were carried out with protocols approved by The Institutional Animal Care and Use Committee.

FIG. 1 shows the dose-dependent effect of a compound of the invention on 5-HT levels in mice.

All of the publications (e.g., patents and patent applications) disclosed above are incorporated herein by reference in their entireties.

What is claimed is:
1. A compound of the formula:

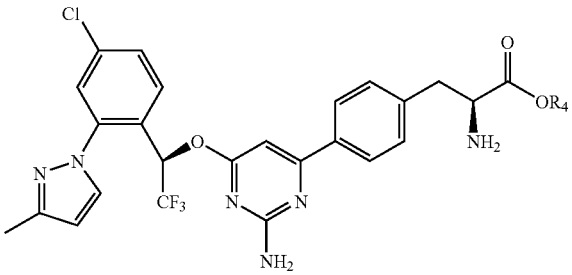

or a pharmaceutically acceptable salt thereof, wherein $R_4$ is hydrogen or lower alkyl.

2. The compound of claim 1, wherein $R_4$ is hydrogen.
3. The compound of claim 1, wherein $R_4$ is lower alkyl.
4. The compound of claim 3, wherein $R_4$ is ethyl.
5. A composition comprising the compound of claim 1 and a pharmaceutically acceptable excipient or diluent.
6. A dosage form suitable for administration to a patient comprising the composition of claim 5.
7. The dosage form of claim 6, which is suitable for oral administration.
8. The dosage form of claim 7, which is a tablet.
9. The dosage form of claim 7, which is a capsule.
10. A compound, which is (S)-2-amino-3-[4-(2-amino-6-{R-1-[4-chloro-2-(3-methyl-pyrazol-1-yl)-phenyl]-2,2,2-trifluoro-ethoxy}-pyrimidin-4-yl)-phenyl]-propionic acid ethyl ester or a pharmaceutically acceptable salt thereof.
11. A tablet comprising the compound of claim 10 and a pharmaceutically acceptable excipient.
12. A capsule comprising the compound of claim 10 and a pharmaceutically acceptable excipient.
13. A compound, which is (S)-2-amino-3-(4-(2-amino-6-((R)-1-(4-chloro-2-(3-methyl-1H-pyrazol-1-yl)phenyl)-2,2,2-trifluoroethoxy)pyrimidin-4-yl)phenyl)propanoic acid or a pharmaceutically acceptable salt thereof.
14. A tablet comprising the compound of claim 13 and a pharmaceutically acceptable excipient.
15. A capsule comprising the compound of claim 13 and a pharmaceutically acceptable excipient.
16. A method of treating or managing carcinoid syndrome, which comprises administering to a patient in need thereof a therapeutically effective amount of a compound of the formula:

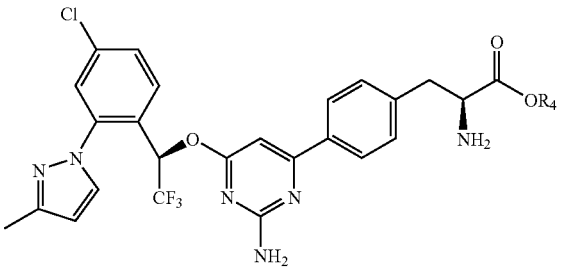

or a pharmaceutically acceptable salt thereof, wherein $R_4$ is hydrogen or lower alkyl.

17. The method of claim 16, wherein $R_4$ is hydrogen.
18. The method of claim 16, wherein $R_4$ is lower alkyl.
19. The method of claim 18, wherein $R_4$ is ethyl.
20. The method of claim 16, wherein the administration is oral.

* * * * *